(12) United States Patent
Suo

(10) Patent No.: US 9,447,137 B2
(45) Date of Patent: Sep. 20, 2016

(54) SUBSTITUTED GEMCITABINE ARYL AMIDE ANALOGS

(71) Applicant: Nucorion Pharmaceuticals, Inc., Wilmington, DE (US)

(72) Inventor: Zucai Suo, Dublin, OH (US)

(73) Assignee: NUCORION PHARMACEUTICALS, INC., Wilmington, DE (US)

( * ) Notice: Subject to any disclaimer, the term of this patent is extended or adjusted under 35 U.S.C. 154(b) by 0 days.

(21) Appl. No.: 14/440,811

(22) PCT Filed: Nov. 7, 2013

(86) PCT No.: PCT/US2013/068965
§ 371 (c)(1),
(2) Date: May 5, 2015

(87) PCT Pub. No.: WO2014/074725
PCT Pub. Date: May 15, 2014

(65) Prior Publication Data
US 2015/0259375 A1     Sep. 17, 2015

Related U.S. Application Data

(60) Provisional application No. 61/723,708, filed on Nov. 7, 2012.

(51) Int. Cl.
| | | |
|---|---|---|
| A61K 31/7068 | (2006.01) |
| C07H 19/06 | (2006.01) |
| A61K 45/06 | (2006.01) |
| A61K 31/555 | (2006.01) |
| A61K 33/24 | (2006.01) |
| A61K 31/282 | (2006.01) |
| C07H 19/067 | (2006.01) |

(52) U.S. Cl.
CPC ............ *C07H 19/06* (2013.01); *A61K 31/282* (2013.01); *A61K 31/555* (2013.01); *A61K 31/7068* (2013.01); *A61K 33/24* (2013.01); *A61K 45/06* (2013.01); *C07H 19/067* (2013.01)

(58) Field of Classification Search
CPC .. C07H 19/073; C07H 19/06; C07H 19/067; A61K 31/7068
See application file for complete search history.

(56) References Cited

U.S. PATENT DOCUMENTS

| | | | | |
|---|---|---|---|---|
| 4,966,891 | A | 10/1990 | Fujiu | |
| 7,456,155 | B2 * | 11/2008 | Sommadossi | C07H 19/06 514/43 |
| 8,603,999 | B2 * | 12/2013 | Drummond | A61K 9/107 514/43 |
| 8,653,048 | B2 * | 2/2014 | Xue | A61K 31/7068 514/49 |
| 2009/0069557 | A1 * | 3/2009 | Palle | C07H 19/067 536/28.51 |
| 2009/0221524 | A1 * | 9/2009 | Kotra | C07H 19/073 514/51 |
| 2010/0075917 | A1 * | 3/2010 | Decout | C07D 405/04 514/50 |
| 2010/0286084 | A1 * | 11/2010 | Ren | C07H 17/02 514/52 |
| 2011/0183933 | A1 * | 7/2011 | Guzi | C07H 19/073 514/50 |
| 2012/0070411 | A1 * | 3/2012 | Beigelman | A61K 31/7068 424/85.4 |
| 2012/0088908 | A1 * | 4/2012 | Xue | C07H 19/06 536/28.5 |
| 2015/0224208 | A1 * | 8/2015 | Ueki | A61K 47/48023 514/1.3 |

FOREIGN PATENT DOCUMENTS

| | | |
|---|---|---|
| CN | 101921303 | 12/2010 |
| WO | WO 2006/065525 A1 | 6/2006 |
| WO | WO 2012/040126 A1 | 3/2012 |
| WO | WO 2013/142525 A1 | 9/2013 |
| WO | WO 2014/074725 A1 | 5/2014 |
| WO | WO 2014/145207 | 9/2014 |
| WO | WO 2015/134334 | 9/2015 |

OTHER PUBLICATIONS

Written Opinion of the International Searching Authority, PCT/US2013/068965 (Feb. 5, 2014).*
CAS Abstract of CN 101921303 (Dec. 22, 2010).*
PubChem SureCN285547, CID 53839260, 11 pages, Create Date: Dec. 4, 2011.

* cited by examiner

*Primary Examiner* — Alexander R Pagano
(74) *Attorney, Agent, or Firm* — Knobbe, Martens, Olson & Bear LLP

(57) ABSTRACT

In one aspect, the invention relates to substituted gemcitabine aryl amide analogs, derivatives thereof, and related compounds; synthesis methods for making the compounds; pharmaceutical compositions comprising the compounds; and methods of treating viral disorders and disorders of uncontrolled cellular proliferation using the compounds and compositions. This abstract is intended as a scanning tool for purposes of searching in the particular art and is not intended to be limiting of the present invention.

42 Claims, 16 Drawing Sheets

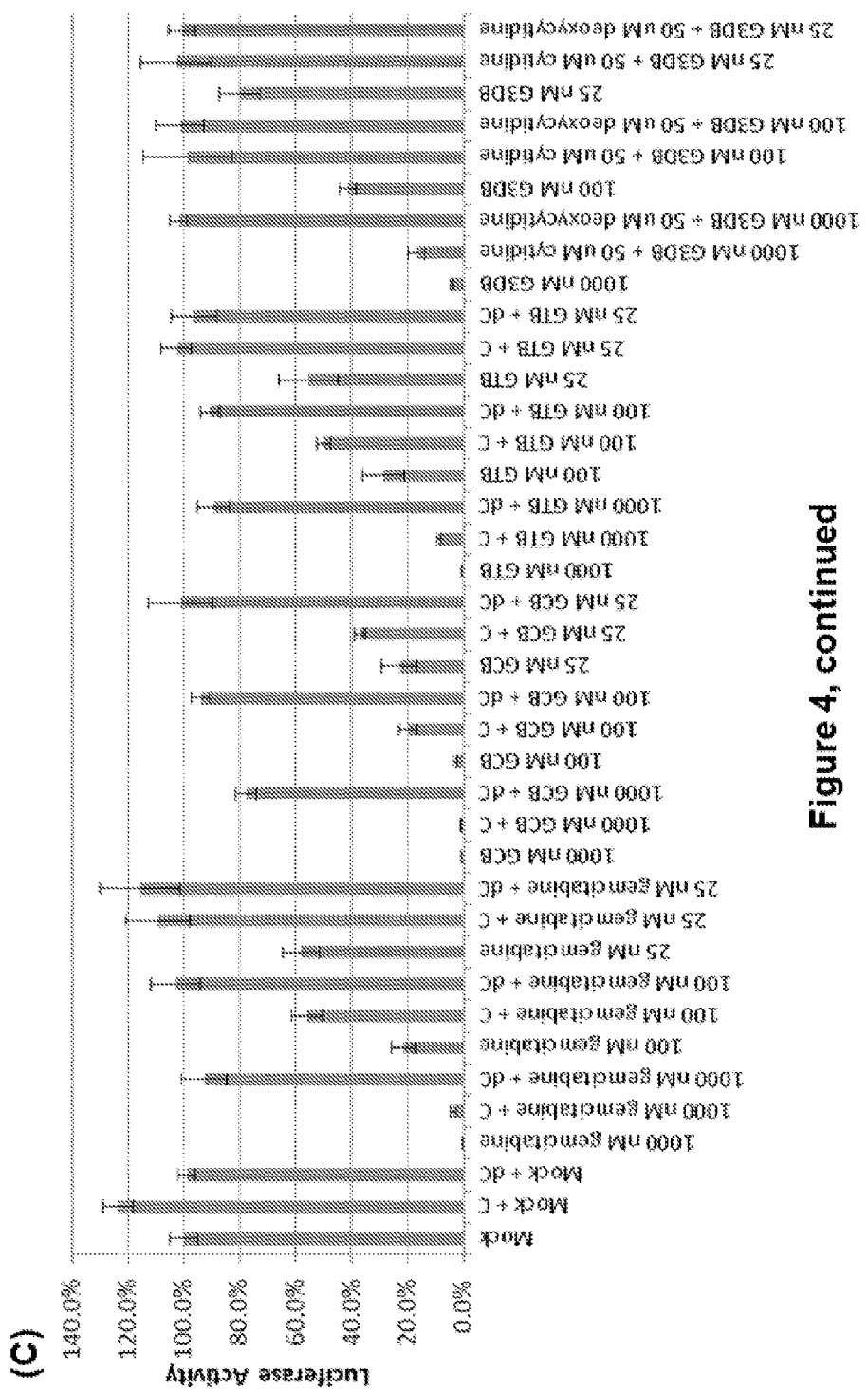
Figure 4, continued

SUBSTITUTED GEMCITABINE ARYL AMIDE ANALOGS

CROSS-REFERENCE TO RELATED APPLICATIONS

This application is the U.S. National Phase of Application No. PCT/US2013/068965 entitled "SUBSTITUTED GEMCITABINE ARYL AMIDE ANALOGS AND TREATMENT METHODS USING SAME" filed Nov. 7, 2013 and published in English on May 15, 2014 as WO2014074725 which claims the benefit of U.S. Provisional Application No. 61/723,708 filed Nov. 7, 2012 entitled "SUBSTITUTED GEMCITABINE ARYL AMIDE ANALOGS AND TREATMENT METHODS USING SAME", the contents of which are hereby incorporated by reference in their entireties.

BACKGROUND

An estimated 170 million people throughout the world are infected with the hepatitis C virus (HCV). More than 70% of these individuals remain chronically infected for life, of which 15-20% eventually develops liver cirrhosis and hepatocellular carcinoma. The current therapy for HCV infections is the combination of ribavirin, interferon-α (IFN-α), and recently approved HCV inhibitors such as Victrelis (boceprevir) and Incivek (telaprevir). Unfortunately, in addition to severe side effects, the sustained response rate of this therapy is only 50-75% and genotype-dependent.

Accordingly, more selective and potent drugs are urgently needed to combat the widespread infections of HCV, especially in the face of and the limited efficacy and severe toxicity of current anti-HCV therapy. This need and other needs are addressed by the present invention.

SUMMARY

In accordance with the purpose(s) of the invention, as embodied and broadly described herein, the invention, in one aspect, relates to substituted gemcitabine aryl amide analogs, methods of making same, pharmaceutical compositions comprising same, and methods of treating viral disorders and disorders of uncontrolled cellular proliferation using same.

Disclosed are compounds having a structure represented by a formula:

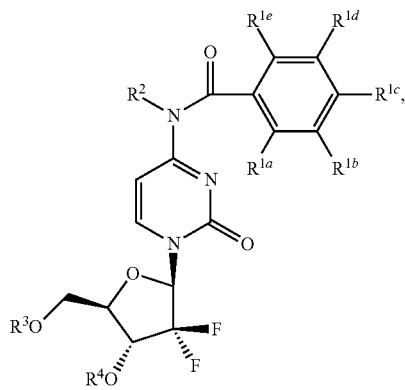

wherein at least one of $R^{1a}$, $R^{1b}$, $R^{1c}$, $R^{1d}$, and $R^{1e}$ is not hydrogen; wherein $R^{1a}$ and $R^{1e}$ are independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted benzyl, optionally substituted phenoxy, nitro, —NH$_2$, amino, monoalkylamino, and dialkylamino; wherein $R^{1b}$ and $R^{1d}$ are independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, nitro, —NH$_2$, amino, monoalkylamino, and dialkylamino; wherein $R^{1c}$ is selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, —C(O)R$^5$, —C(O)OR$^5$, —C(O)NHR$^5$, —OC(O)R$^5$, —NHC(O)R$^5$, and —NHC(O)OR$^5$, wherein R$^5$ is hydrogen, methyl, ethyl, propyl, butyl, pentyl, or hexyl; wherein R$^2$ is selected from hydrogen, C1-C4 alkyl, and amine protecting group; wherein R$^3$ is selected from hydrogen and hydroxyl protecting group; and wherein R$^4$ is selected from hydrogen, C1-C8 alkyl, and hydroxyl protecting group, or wherein R$^3$ and R$^4$ together comprise a divalent moiety having a structure represented by a formula:

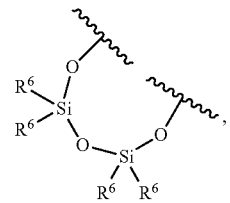

wherein each R$^6$ is independently selected from methyl, ethyl, propyl, and butyl.

Also disclosed are compounds having a structure represented by a formula:

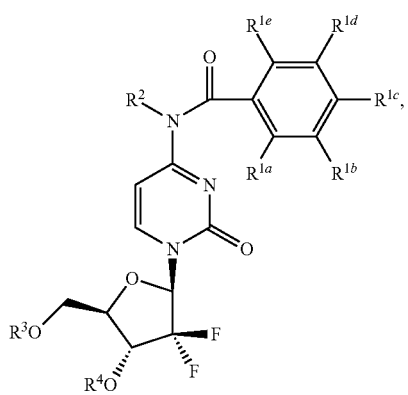

wherein at least two of $R^{1a}$, $R^{1b}$, $R^{1c}$, $R^{1d}$, and $R^{1e}$ are not hydrogen; wherein each of $R^{1a}$, $R^{1b}$, $R^{1c}$, $R^{1d}$, and $R^{1e}$ is independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, nitro, —NH$_2$, amino, monoalkylamino, dialkylamino, —C(O)R$^5$, —C(O)OR$^5$, —C(O)NHR$^5$, —OC(O)R$^5$, —NHC(O)R$^5$, and —NHC(O)OR$^5$, wherein R$^5$ is hydrogen, methyl, ethyl, propyl, butyl, pentyl, or hexyl; provided that R$^{1a}$=R$^{1b}$≠H, or R$^{1a}$=R$^{1c}$≠H, or R$^{1a}$=R$^{1d}$≠H, or R$^{1a}$=R$^{1e}$≠H, or R$^{1b}$=R$^{1c}$≠H, or R$^{1b}$=R$^{1d}$≠H, or R$^{1b}$=R$^{1e}$ H, or R$^1$=R$^{1d}$≠H, or R$^{1c}$=R$^{1e}$≠H, or R$^{1d}$=R$^{1e}$≠H; wherein R$^2$ is selected from hydrogen, C1-C4 alkyl, and amine protecting group; wherein R$^3$ is selected from hydrogen and hydroxyl protecting group; and wherein R$^4$ is selected from hydrogen, C1-C8 alkyl, and hydroxyl protecting group, or wherein R$^3$ and R$^4$ together comprise a divalent moiety having a structure represented by a formula:

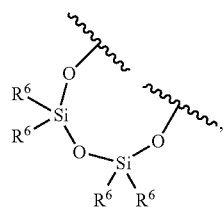

wherein each R$^6$ is independently selected from methyl, ethyl, propyl, and butyl.

Also disclosed are compounds having a structure represented by a formula:

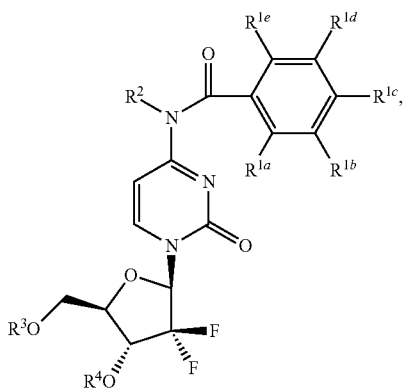

wherein at least three of R$^{1a}$, R$^{1b}$, R$^{1c}$, R$^{1d}$, and R$^{1e}$ are not hydrogen; wherein each of R$^{1a}$, R$^{1b}$, R$^{1c}$, R$^{1d}$, and R$^{1e}$ is independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, nitro, —NH$_2$, amino, monoalkylamino, dialkylamino, —C(O)R$^5$, —C(O)OR$^5$, —C(O)NHR$^5$, —OC(O)R$^5$, —NHC(O)R$^5$, and —NHC(O)OR$^5$, wherein R$^5$ is hydrogen, methyl, ethyl, propyl, butyl, pentyl, or hexyl; wherein R$^2$ is selected from hydrogen, C1-C4 alkyl, and amine protecting group; wherein R$^3$ is selected from hydrogen and hydroxyl protecting group; and wherein R$^4$ is selected from hydrogen, C1-C8 alkyl, and hydroxyl protecting group, or wherein R$^3$ and R$^4$ together comprise a divalent moiety having a structure represented by a formula:

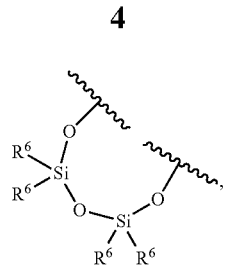

wherein each R$^6$ is independently selected from methyl, ethyl, propyl, and butyl.

Also disclosed are methods for making a compound comprising the steps of: (a) providing a first compound having a structure represented by a formula:

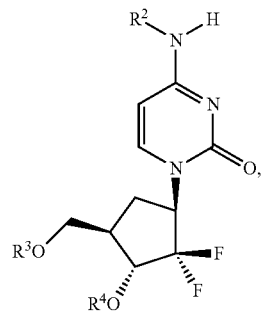

wherein R$^2$ is selected from hydrogen, C1-C4 alkyl, and amine protecting group; wherein R$^3$ is selected from hydrogen and hydroxyl protecting group; and wherein R$^4$ is selected from hydrogen, C1-C8 alkyl, and hydroxyl protecting group, or wherein R$^3$ and R$^4$ together comprise a divalent moiety having a structure represented by a formula:

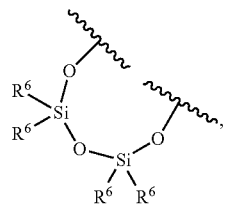

wherein each R$^6$ is independently selected from methyl, ethyl, propyl, and butyl, and (b) reacting with a second compound having a structure represented by a formula:

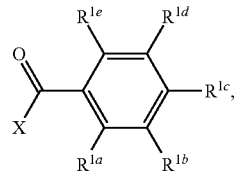

wherein X is halogen or pseudohalogen; wherein 1, 2, 3, 4, or 5 of R$^{1a}$, R$^{1b}$, R$^{1c}$, R$^{1d}$, and R$^{1e}$ are not hydrogen; and wherein each of R$^{1a}$, R$^{1b}$, R$^{1c}$, R$^{1d}$, and R$^{1e}$ is independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, nitro, —NH$_2$, amino, monoalkylamino, dialkylamino, —C(O)R$^5$, —C(O)OR$^5$, —C(O)NHR$^5$, —OC(O)R$^5$, —NHC(O)R$^5$, and —NHC(O)OR$^5$, wherein R$^5$ is hydrogen, methyl, ethyl, propyl, butyl, pentyl, or hexyl, thereby forming an amide bond.

Also disclosed are products of the disclosed methods.

Also disclosed are pharmaceutical compositions comprising a pharmaceutically acceptable carrier and an effective amount of a disclosed compound or the product of a disclosed method.

Also disclosed are kits comprising a disclosed compound or the product of a disclosed method or a disclosed pharmaceutical composition and one or more of: (a) an antiviral agent; (b) a substance known to increase risk of viral infection; (c) instructions for treating a viral infection; (d) a drug known to treat a disorder of uncontrolled cellular proliferation; (e) a substance known to increase risk of uncontrolled cellular proliferation; and (f) instructions for treating a disorder of uncontrolled cellular proliferation.

Also disclosed are methods for treating a subject for viral infection, the method comprising the step of administering to the subject an effective amount of a disclosed compound or the product of a disclosed method or a disclosed pharmaceutical composition.

Also disclosed are methods for inhibiting viral replication within at least one cell, the method comprising the step of administering to the cell an effective amount of a disclosed compound or a product of a disclosed method or a disclosed pharmaceutical composition.

Also disclosed are methods for treating a disorder of uncontrolled cellular proliferation, the method comprising administering to a subject an effective amount of a disclosed compound or a disclosed product or a disclosed pharmaceutical composition.

Also disclosed are methods for arresting tumor growth, the method comprising administering to at least one tumor cell an effective amount of a disclosed compound or a product of a disclosed method or a disclosed pharmaceutical composition.

Also disclosed are uses of a disclosed compound, a disclosed product of making, or a pharmaceutically acceptable salt, hydrate, solvate, or polymorph thereof.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
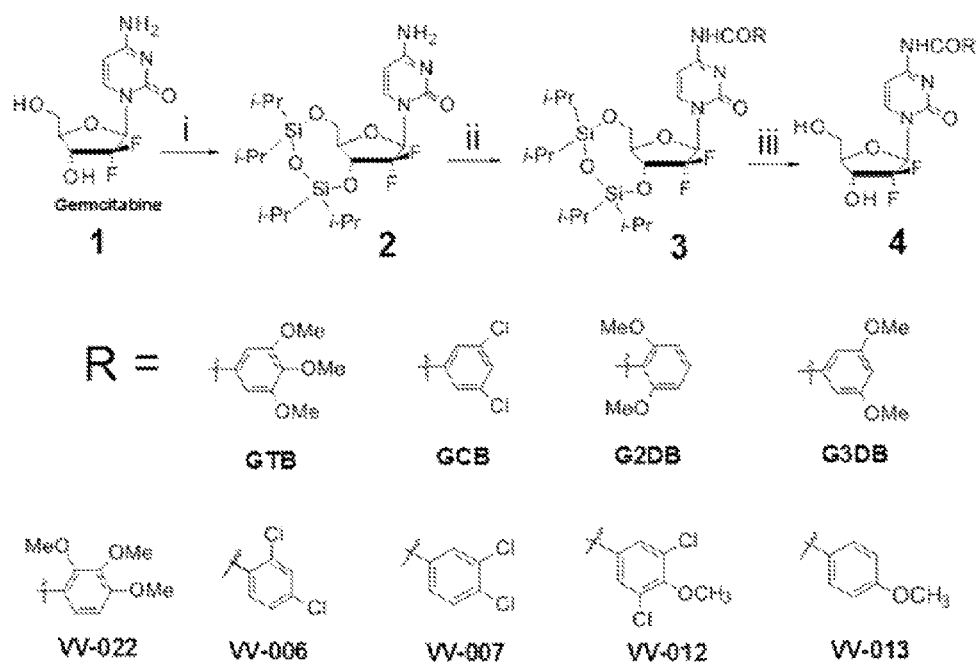
FIG. 1 shows an example synthetic scheme for gemcitabine derivatives. The reagents and conditions in each step of this example are: (i) TIPDSiCl$_2$, pyridine, room temperature; (ii) RCOCl, pyridine, room temperature; (iii) TBAF/THF, room temperature.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment prior to the administering step. In further aspects, the disclosed methods further comprise the step of identifying a subject in need of treatment for the disorder. In one aspect, a subject can be treated prophylactically with a compound or composition disclosed herein, as discussed herein elsewhere.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the phrase "identified to be in need of treatment for a disorder," or the like, refers to selection of a subject based upon need for treatment of the disorder. For example, a subject can be identified as having a need for treatment of a disorder based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, a target receptor, or other biological entity together in such a manner that the compound can affect the activity of the target, either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "$IC_{50}$," is intended to refer to the concentration of a substance (e.g., a compound or a drug) that is required for 50% inhibition of a biological process, or component of a process. For example, $IC_{50}$ refers to the half maximal (50%) inhibitory concentration (IC) of a substance as determined in a suitable assay.

As used herein, "$TC_{50}$," is intended to refer to toxic concentration of a substance (e.g., a compound or a drug) for 50% of the population. For example, $TC_{50}$ can refer to the half maximal (50%) toxicity concentration (TC) of a substance as determined in a suitable assay, for example, an assay disclosed herein.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or disubstituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

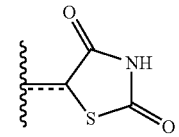

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, disubstituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units ofunsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide" as used herein can be used interchangeably and refer to F, Cl, Br, or I.

The terms "pseudohalide," "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl" as used herein can be used interchangeably and refer to single and multi-cyclic aromatic or non-aromatic ring systems in which at least one of the ring members is other than carbon. Thus, the term is inclusive of, but not limited to, "heterocycloalkyl", "heteroaryl", "bicyclic heterocycle" and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxy" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR_2$; $-C(S)SR^\circ$; $-(CH_2)_{0-4}C(O)NR_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched alkylene)$O-N(R^\circ)_2$; or $-(C_{1-4}$ straight or branched alkylene)$C(O)O-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(halo$R^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =NNR*_2, =NNHC(O)R*, =NNHC(O)OR*, =NNHS(O)_2R*, =NR*, =NOR*, $-O(C(R*_2))_{2-3}O-$, or $-S(C(R*_2))_{2-3}S-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR*_2)_{2-3}O-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, $-R^\bullet$, -(halo$R^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^†$ are independently halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, sulfur, fluorine and chlorine, such as $^2$H, $^3$H, $^{13}$C, $^{14}$C, $^{15}$N, $^{18}$O, $^{17}$O, $^{35}$S, $^{18}$F and $^{36}$Cl, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

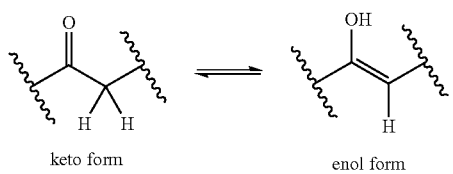

keto form          enol form

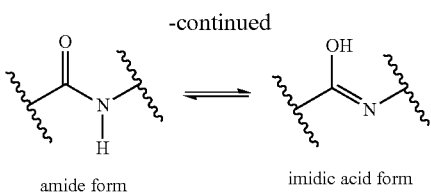

amide form      imidic acid form

Likewise, amides with an N-hydrogen can exist in an equilibrium of the amide form and the imidic acid form. As another example, pyrazoles can exist in two tautomeric forms, $N^1$-unsubstituted, $3\text{-}A^3$ and $N^1$-unsubstituted, $5\text{-}A^3$ as shown below.

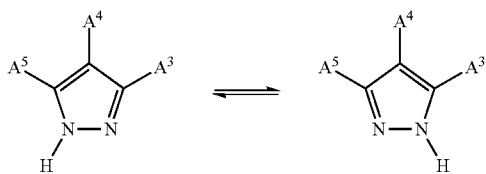

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

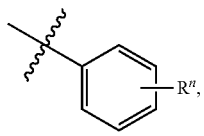

which is understood to be equivalent to a formula:

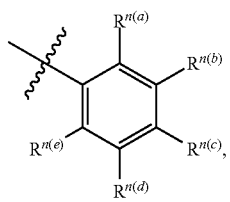

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental Volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to gemcitabine amide analog compounds. More specifically, in one aspect, the present invention relates to compounds useful for treatment of cancers or hepatitis.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Substituted Gemcitabine Amide Analogs

In one aspect, the invention relates to a compound, or pharmaceutically acceptable salt, solvate, or polymorph thereof, having a structure represented by a formula:

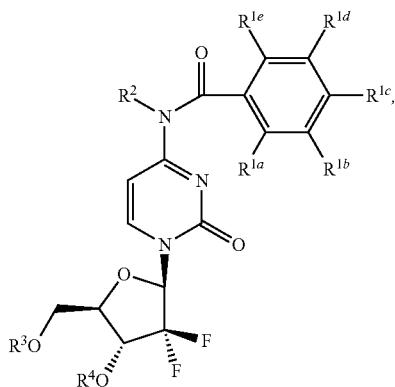

wherein at least one of $R^{1a}$, $R^{1b}$, $R^{1c}$, $R^{1d}$, and $R^{1e}$ is not hydrogen; wherein $R^{1a}$ and $R^{1e}$ are independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted benzyl, optionally substituted phenoxy, nitro, —NH$_2$, amino, monoalkylamino, and dialkylamino; wherein $R^{1b}$ and $R^{1d}$ are independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, nitro, —NH$_2$, amino, monoalkylamino, and dialkylamino; wherein $R^{1c}$ is selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, —C(O)R$^5$, —C(O)OR$^5$, —C(O)NHR$^5$, —OC(O)R$^5$, —NHC(O)R$^5$, and —NHC(O)OR$^5$, wherein R$^5$ is hydrogen, methyl, ethyl, propyl, butyl, pentyl, or hexyl; wherein $R^2$ is selected from hydrogen, C1-C4 alkyl, and amine protecting group; wherein $R^3$ is selected from hydrogen and hydroxyl protecting group; and wherein $R^4$ is selected from hydrogen, C1-C8 alkyl, and hydroxyl protecting group, or wherein $R^3$ and $R^4$ together comprise a divalent moiety having a structure represented by a formula:

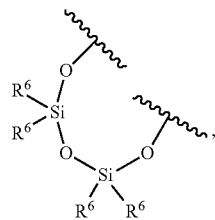

wherein each $R^6$ is independently selected from methyl, ethyl, propyl, and butyl.

In a further aspect, the compound, or pharmaceutically acceptable salt, solvate, or polymorph thereof, has a structure represented by a formula:

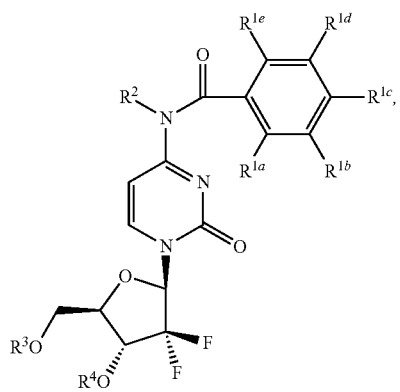

wherein at least one of $R^{1a}$, $R^{1b}$, $R^{1c}$, $R^{1d}$, and $R^{1e}$ is not hydrogen; wherein $R^{1a}$ and $R^{1e}$ are independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted benzyl, optionally substituted phenoxy, nitro, —NH$_2$, amino, monoalkylamino, and dialkylamino; wherein $R^{1b}$ and $R^{1d}$ are independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, nitro, —NH$_2$, amino, monoalkylamino, and dialkylamino; wherein $R^{1c}$ is selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, —C(O)R$^5$, —C(O)OR$^5$, —C(O)NHR$^5$, —OC(O)R$^5$, —NHC(O)R$^5$, and —NHC(O)OR$^5$, wherein R$^5$ is hydrogen, methyl, ethyl, propyl, butyl, pentyl, or hexyl; wherein $R^2$ is selected from hydrogen, C1-C4 alkyl, and amine protecting group; wherein $R^3$ is selected from hydrogen and hydroxyl protecting group; and wherein $R^4$ is selected from hydrogen, C1-C8 alkyl, and hydroxyl protecting group.

In a further aspect, $R^2$, $R^3$, and $R^4$ are hydrogen.

In a further aspect, the compound is disubstituted at the aryl ring. That is, at least two of $R^{1a}$, $R^{1b}$, $R^{1c}$, $R^{1d}$, and $R^{1e}$ are not hydrogen. In a further aspect, the compound is trisubstituted at the aryl ring. That is, at least three of $R^{1a}$, $R^{1b}$, $R^{1c}$, $R^{1d}$, and $R^{1e}$ are not hydrogen. In a further aspect, the compound is tetrasubstituted at the aryl ring. That is, at least four of $R^{1a}$, $R^{1b}$, $R^{1c}$, $R^{1d}$, and $R^{1e}$ are not hydrogen. In a further aspect, the compound is pentasubstituted at the aryl ring. That is, all of $R^{1a}$, $R^{1b}$, $R^{1c}$, $R^{1d}$, and $R^{1e}$ are not hydrogen.

In a further aspect, $R^{1a}=R^{1e}$. In a further aspect, $R^{1a}=R^{1e}$, and $R^{1b}$, $R^{1c}$, and $R^{1d}$ are hydrogen. In a further aspect, $R^{1b}=R^{1d}$. In a further aspect, $R^{1b}=R^{1d}$, and $R^{1a}$, $R^{1c}$, and $R^{1e}$ are hydrogen. In a further aspect, $R^{1b}=R^{1c}=R^{1d}$. In a further aspect, $R^{1b}=R^{1c}=R^{1d}$, and $R^{1a}$ and $R^{1e}$ are hydrogen. In a further aspect, $R^{1a}=R^{1b}\neq H$, or $R^{1a}=R^{1c}\neq H$, or $R^{1a}=R^{1d}\neq H$, or $R^{1a}=R^{1e}\neq H$, or $R^{1b}=R^{1c}\neq H$, or $R^{1b}=R^{1d}\neq H$, or $R^{1b}=R^{1e}\neq H$, or $R^{1c}=R^{1d}\neq H$, or $R^{1c}=R^{1e}\neq H$, or $R^{1d}=R^{1e}\neq H$. In a further aspect, $R^{1a}=R^{1e}\neq H$, or $R^{1b}=R^{1d}\neq H$, or $R^{1a}=R^{1c}=R^{1e}\neq H$, or $R^{1b}=R^{1c}=R^{1d}\neq H$.

2. Disubstituted Gemcitabine Amide Analogs

In one aspect, the invention relates to a compound, or pharmaceutically acceptable salt, solvate, or polymorph thereof, having a structure represented by a formula:

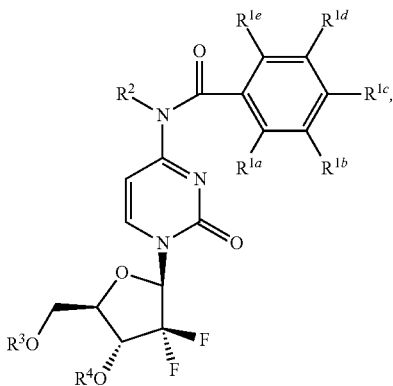

wherein at least two of $R^{1a}$, $R^{1b}$, $R^{1c}$, $R^{1d}$, and $R^{1e}$ are not hydrogen; wherein each of $R^{1a}$, $R^{1b}$, $R^{1c}$, $R^{1d}$, and $R^{1e}$ is independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, nitro, —NH$_2$, amino, monoalkylamino, dialkylamino, —C(O)R$^5$, —C(O)OR$^5$, —C(O)NHR$^5$, —OC(O)R$^5$, —NHC(O)R$^5$, and —NHC(O)OR$^5$, wherein R$^5$ is hydrogen, methyl, ethyl, propyl, butyl, pentyl, or hexyl; provided that $R^{1a}=R^{1b}\neq H$, or $R^{1a}=R^{1c}\neq H$, or $R^{1a}=R^{1d}\neq H$, or $R^{1a}=R^{1e}\neq H$, or $R^{1b}=R^{1c}\neq H$, or $R^{1b}=R^{1d}\neq H$, or $R^{1b}=R^{1e}\neq H$, or $R^{1c}=R^{1d}\neq H$, or $R^{1c}=R^{1e}\neq H$, or $R^{1d}=R^{1e}\neq H$; wherein R$^2$ is selected from hydrogen, C1-C4 alkyl, and amine protecting group; wherein R$^3$ is selected from hydrogen and hydroxyl protecting group; and wherein R$^4$ is selected from hydrogen, C1-C8 alkyl, and hydroxyl protecting group, or wherein R$^3$ and R$^4$ together comprise a divalent moiety having a structure represented by a formula:

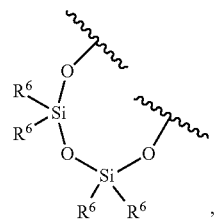

wherein each R$^6$ is independently selected from methyl, ethyl, propyl, and butyl.

In a further aspect, the compound, or pharmaceutically acceptable salt, solvate, or polymorph thereof, has a structure represented by a formula:

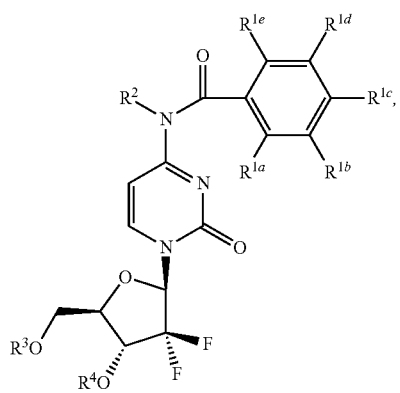

wherein at least two of $R^{1a}$, $R^{1b}$, $R^{1c}$, $R^{1d}$, and $R^{1e}$ are not hydrogen; wherein each of $R^{1a}$, $R^{1b}$, $R^{1c}$, $R^{1d}$, and $R^{1e}$ is independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, nitro, —NH$_2$, amino, monoalkylamino, dialkylamino, —C(O)R$^5$, —C(O)OR$^5$, —C(O)NHR$^5$, —OC(O)R$^5$, —NHC(O)R$^5$, and —NHC(O)OR$^5$, wherein R$^5$ is hydrogen, methyl, ethyl, propyl, butyl, pentyl, or hexyl; provided that $R^{1a}=R^{1b}\neq H$, or $R^{1a}=R^{1c}\neq H$, or $R^{1a}=R^{1d}\neq H$, or $R^{1a}=R^{1e}\neq H$, or $R^{1b}=R^{1c}\neq H$, or $R^{1b}=R^{1d}\neq H$, or $R^{1b}=R^{1e}\neq H$, or $R^{1c}=R^{1d}\neq H$, or $R^{1c}=R^{1e}\neq H$, or $R^{1d}=R^{1e}$ H; wherein R$^2$ is selected from hydrogen, C1-C4 alkyl, and amine protecting group; wherein R$^3$ is selected from hydrogen and hydroxyl protecting group; and wherein R$^4$ is selected from hydrogen, C1-C8 alkyl, and hydroxyl protecting group.

In a further aspect, $R^{1a}=R^{1e}\neq H$, or $R^{1b}=R^{1d}\neq H$, or $R^{1a}=R^{1c}=R^{1e}\neq H$, or $R^{1b}=R^{1c}=R^{1d}\neq H$. In a further aspect, R$^2$, R$^3$, and R$^4$ are hydrogen. In a further aspect, $R^{1a}=R^{1e}$. In a further aspect, $R^{1b}=R^{1d}$. In a further aspect, $R^{1b}=R^{1c}=R^{1d}$. In a further aspect, at least three of $R^{1a}$, $R^{1b}$, $R^{1c}$, $R^{1d}$, and $R^{1e}$ are not hydrogen.

In a further aspect, $R^{1a}$ and $R^{1e}$ are independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted benzyl, optionally substituted phenoxy, nitro, —NH$_2$, amino, monoalkylamino, and dialkylamino.

In a further aspect, $R^{1b}$ and $R^{1d}$ are independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, nitro, —$NH_2$, amino, monoalkylamino, and dialkylamino.

In a further aspect, $R^{1c}$ is selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, —C(O)$R^5$, —C(O)O$R^5$, —C(O)NH$R^5$, —OC(O)$R^5$, —NHC(O)$R^5$, and —NHC(O)O$R^5$, wherein $R^5$ is hydrogen, methyl, ethyl, propyl, butyl, pentyl, or hexyl.

In a further aspect, $R^{1a}$ and $R^{1e}$ are not hydrogen. In a further aspect, $R^{1b}$ and $R^{1d}$ are not hydrogen. In a further aspect, $R^{1b}$, $R^{1d}$, and $R^{1c}$ are not hydrogen.

3. Trisubstituted Gemcitabine Amide Analogs

In one aspect, the invention relates to a compound, or pharmaceutically acceptable salt, solvate, or polymorph thereof, having a structure represented by a formula:

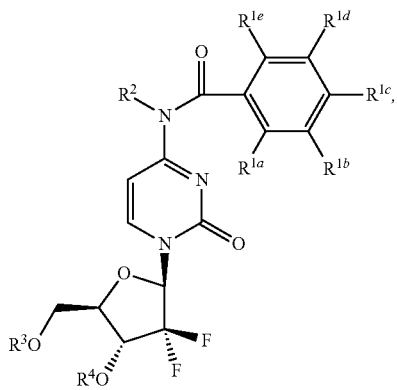

wherein at least three of $R^{1a}$, $R^{1b}$, $R^{1c}$, $R^{1d}$, and $R^{1e}$ are not hydrogen; wherein each of $R^{1a}$, $R^{1b}$, $R^{1c}$, $R^{1d}$, and $R^{1e}$ is independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, nitro, —$NH_2$, amino, monoalkylamino, dialkylamino, —C(O)$R^5$, —C(O)O$R^5$, —C(O)NH$R^5$, —OC(O)$R^5$, —NHC(O)$R^5$, and —NHC(O)O$R^5$, wherein $R^5$ is hydrogen, methyl, ethyl, propyl, butyl, pentyl, or hexyl; wherein $R^2$ is selected from hydrogen, C1-C4 alkyl, and amine protecting group; wherein $R^3$ is selected from hydrogen and hydroxyl protecting group; and wherein $R^4$ is selected from hydrogen, C1-C8 alkyl, and hydroxyl protecting group, or wherein $R^3$ and $R^4$ together comprise a divalent moiety having a structure represented by a formula:

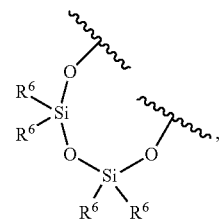

wherein each $R^6$ is independently selected from methyl, ethyl, propyl, and butyl.

In a further aspect, the compound, or pharmaceutically acceptable salt, solvate, or polymorph thereof, has a structure represented by a formula:

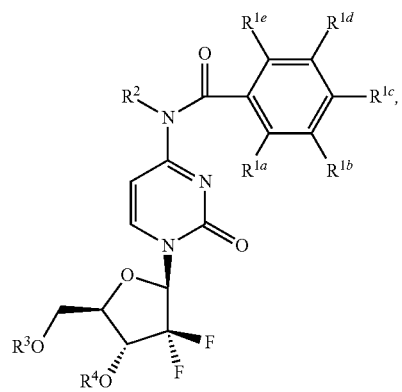

wherein at least three of $R^{1a}$, $R^{1b}$, $R^{1c}$, $R^{1d}$, and $R^{1e}$ are not hydrogen; wherein each of $R^{1a}$, $R^{1b}$, $R^{1c}$, $R^{1d}$, and $R^{1e}$ is independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, nitro, —$NH_2$, amino, monoalkylamino, dialkylamino, —C(O)$R^5$, —C(O)O$R^5$, —C(O)NH$R^5$, —OC(O)$R^5$, —NHC(O)$R^5$, and —NHC(O)O$R^5$, wherein $R^5$ is hydrogen, methyl, ethyl, propyl, butyl, pentyl, or hexyl; wherein $R^2$ is selected from hydrogen, C1-C4 alkyl, and amine protecting group; wherein $R^3$ is selected from hydrogen and hydroxyl protecting group; and wherein $R^4$ is selected from hydrogen, C1-C8 alkyl, and hydroxyl protecting group.

In a further aspect, $R^2$, $R^3$, and $R^4$ are hydrogen.

In a further aspect, $R^{1a}$ and $R^{1e}$ are independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted benzyl, optionally substituted phenoxy, nitro, —$NH_2$, amino, monoalkylamino, and dialkylamino.

In a further aspect, $R^{1b}$ and $R^{1d}$ are independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, nitro, —NH$_2$, amino, monoalkylamino, and dialkylamino.

In a further aspect, $R^{1c}$ is selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, —C(O)R$^5$, —C(O)OR$^5$, —C(O)NHR$^5$, —OC(O)R$^5$, —NHC(O)R$^5$, and —NHC(O)OR$^5$, wherein R$^5$ is hydrogen, methyl, ethyl, propyl, butyl, pentyl, or hexyl.

In a further aspect, $R^2$ is an amine protecting group selected from Fmoc, BOC, Cbz, acetyl, trifluoroacetamide, phthalimide, benzyl, triphenylmethylamine, benzylideneamine, and p-toluenesulfonamide. In a further aspect, $R^3$ is a hydroxyl protecting group selected from MOM, THP, t-butyl ether, allyl ether, benzyl, TIPDS, TBDMS, TBDPS, acetyl, pivalic acid ester, acetonide, benzoyl, and benzylidene acetal. In a further aspect, $R^4$ is a hydroxyl protecting group selected from MOM, THP, t-butyl ether, allyl ether, benzyl, TIPDS, TBDMS, TBDPS, acetyl, pivalic acid ester, acetonide, benzoyl, and benzylidene acetal.

In a further aspect, $R^{1a}$ and $R^{1e}$ are independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, and cyano. In a further aspect, $R^{1a}$ and $R^{1e}$ are independently selected from hydrogen, fluoro, chloro, bromo, and iodo. In a further aspect, $R^{1a}$ and $R^{1e}$ are independently selected from hydrogen, methyl, ethyl, propyl, and butyl. In a further aspect, $R^{1a}$ and $R^{1e}$ are independently selected from hydrogen, methoxy, ethoxy, propoxy, and butoxy. In a further aspect, $R^{1a}$ and $R^{1e}$ are independently selected from hydrogen, cyano, hydroxy, thiol, alkylthiol, optionally substituted benzyl, and optionally substituted phenoxy. In a further aspect, $R^{1a}$ and $R^{1e}$ are independently selected from hydrogen, nitro, —NH$_2$, amino, monoalkylamino, and dialkylamino. In a further aspect, $R^{1a}$ and $R^e$ are independently selected from hydrogen, fluoro, chloro, bromo, iodo, and methoxy. In a further aspect, $R^{1b}$ and $R^{1d}$ are independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, and cyano. In a further aspect, $R^{1b}$ and $R^{1d}$ are independently selected from hydrogen, fluoro, chloro, bromo, and iodo. In a further aspect, $R^{1b}$ and $R^{1d}$ are independently selected from hydrogen, methyl, ethyl, propyl, and butyl. In a further aspect, $R^{1b}$ and $R^{1d}$ are independently selected from hydrogen, methoxy, ethoxy, propoxy, and butoxy. In a further aspect, $R^{1b}$ and $R^{1d}$ are independently selected from hydrogen, cyano, hydroxy, thiol, alkylthiol, optionally substituted phenyl, optionally substituted benzyl, and optionally substituted phenoxy. In a further aspect, $R^{1b}$ and $R^{1d}$ are independently selected from hydrogen, nitro, —NH$_2$, amino, monoalkylamino, and dialkylamino. In a further aspect, $R^{1b}$ and $R^{1d}$ are independently selected from hydrogen, fluoro, chloro, bromo, iodo, and methoxy. In a further aspect, $R^{1c}$ is selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, and cyano. In a further aspect, $R^{1c}$ is selected from hydrogen, fluoro, chloro, bromo, and iodo. In a further aspect, RC is selected from hydrogen, methyl, ethyl, propyl, and butyl. In a further aspect, RC is selected from hydrogen, methoxy, ethoxy, propoxy, and butoxy. In a further aspect, $R^{1c}$ is selected from hydrogen, cyano, hydroxy, thiol, alkylthiol, optionally substituted phenyl, optionally substituted benzyl, and optionally substituted phenoxy. In a further aspect, $R^{1c}$ is selected from hydrogen, —C(O)R$^5$, —C(O)OR$^5$, —C(O)NHR$^5$, —OC(O)R$^5$, —NHC(O)R$^5$, and —NHC(O)OR$^5$, wherein R$^5$ is hydrogen, methyl, ethyl, propyl, butyl, pentyl, or hexyl. In a further aspect, $R^{1c}$ is selected from hydrogen, fluoro, chloro, bromo, iodo, and methoxy. In a further aspect, two or three of $R^{1a}$, $R^{1b}$, $R^{1c}$, $R^{1d}$, and $R^{1e}$ are not hydrogen; each of $R^{1a}$, $R^{1b}$, $R^{1c}$, $R^{1d}$, and $R^{1e}$ is independently selected from hydrogen, hydrogen, chloro, and methoxy; and $R^2$, $R^3$, and $R^4$ are hydrogen. In a further aspect, $R^{1a}$=$R^{1e}$≠H, or $R^{1b}$=$R^{1d}$≠H, or $R^{1a}$=$R^{1c}$=$R^{1}$≠H, or $R^{1b}$=$R^{1c}$=$R^{1d}$≠H.

4. Substituent Groups

In various aspects, "optionally substituted" refers to substitution with 0-3 groups independently selected from fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, butyl, cyano, hydroxy, thiol, alkylthiol, acetamide, optionally substituted aryl, optionally substituted heteroaryl, phenoxy, nitro, —NH$_2$, amino, monoalkylamino, dialkylamino, acetyl, acetoxy, carboxy, alkyl carboxy, and sulfamido; wherein valence is satisfied.

In various aspects, the invention can include the following substituent groups.

a. R$^1$ Groups

In one aspect, each R$^1$ group (i.e., $R^{1a}$, $R^{1b}$, $R^{1c}$, $R^{1d}$, and $R^{1e}$) is independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, nitro, —NH$_2$, amino, monoalkylamino, dialkylamino, —C(O)R$^5$, —C(O)OR$^5$, —C(O)NHR$^5$, —OC(O)R$^5$, —NHC(O)R$^5$, and —NHC(O)OR$^5$.

In a further aspect, $R^{1a}$ is selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted benzyl, optionally substituted phenoxy, nitro, —NH$_2$, amino, monoalkylamino, and dialkylamino.

In a further aspect, $R^{1a}$ is selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, and cyano. In a further aspect, $R^{1a}$ is selected from hydrogen, fluoro, chloro, bromo, and iodo. In a further aspect, $R^{1a}$ is selected from hydrogen, methyl, ethyl, propyl, and butyl. In a further aspect, $R^{1a}$ is selected from hydrogen, methoxy, ethoxy, propoxy, and butoxy. In a further aspect, $R^{1a}$ is selected from hydrogen, cyano, hydroxy, thiol, alkylthiol, optionally substituted benzyl, and optionally substituted phenoxy. In a further aspect, $R^{1a}$ is selected from hydrogen, nitro, —NH$_2$, amino, monoalkylamino, and dialkylamino. In a further aspect, $R^{1a}$ is selected from hydrogen, fluoro, chloro, bromo, iodo, and methoxy.

In a further aspect, $R^{1b}$ is selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, nitro, —NH$_2$, amino, monoalkylamino, and dialkylamino.

In a further aspect, $R^{1b}$ is selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, and cyano. In a further aspect, $R^{1b}$ is selected from hydrogen, fluoro, chloro, bromo, and iodo. In a further aspect, $R^{1b}$ is selected from hydrogen, methyl, ethyl, propyl, and butyl. In a further aspect, $R^{1b}$ is selected from hydrogen, methoxy, ethoxy, propoxy, and butoxy. In a further aspect, $R^{1b}$ is selected from hydrogen, cyano, hydroxy, thiol, alkylthiol, optionally substituted phenyl, optionally substituted benzyl, and optionally substituted phenoxy. In a further aspect, $R^{1b}$ is selected from hydrogen, nitro, —$NH_2$, amino, monoalkylamino, and dialkylamino. In a further aspect, $R^{1b}$ is selected from hydrogen, fluoro, chloro, bromo, iodo, and methoxy.

In a further aspect, $R^{1c}$ is selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, —C(O)$R^5$, —C(O)O$R^5$, —C(O)NH$R^5$, —OC(O)$R^5$, —NHC(O)$R^5$, and —NHC(O)O$R^5$.

In a further aspect, $R^{1d}$ is selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, and cyano. In a further aspect, $R^{1c}$ is selected from hydrogen, fluoro, chloro, bromo, and iodo. In a further aspect, $R^{1c}$ is selected from hydrogen, methyl, ethyl, propyl, and butyl. In a further aspect, $R^{1c}$ is selected from hydrogen, methoxy, ethoxy, propoxy, and butoxy. In a further aspect, $R^{1c}$ is selected from hydrogen, cyano, hydroxy, thiol, alkylthiol, optionally substituted phenyl, optionally substituted benzyl, and optionally substituted phenoxy. In a further aspect, $R^{1c}$ is selected from hydrogen, —C(O)$R^5$, —C(O)O$R^5$, —C(O)NH$R^5$, —OC(O)$R^5$, —NHC(O)$R^5$, and —NHC(O)O$R^5$, wherein $R^5$ is hydrogen, methyl, ethyl, propyl, butyl, pentyl, or hexyl. In a further aspect, $R^{1c}$ is selected from hydrogen, fluoro, chloro, bromo, iodo, and methoxy.

In a further aspect, $R^{1d}$ is selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, nitro, —$NH_2$, amino, monoalkylamino, and dialkylamino.

In a further aspect, $R^{1d}$ is selected from hydrogen, fluoro, chloro, bromo, and iodo. In a further aspect, $R^{1d}$ is selected from hydrogen, methyl, ethyl, propyl, and butyl. In a further aspect, $R^{1d}$ is selected from hydrogen, methoxy, ethoxy, propoxy, and butoxy. In a further aspect, $R^{1d}$ is selected from hydrogen, cyano, hydroxy, thiol, alkylthiol, optionally substituted phenyl, optionally substituted benzyl, and optionally substituted phenoxy. In a further aspect, $R^{1d}$ is selected from hydrogen, nitro, —$NH_2$, amino, monoalkylamino, and dialkylamino. In a further aspect, $R^{1d}$ is selected from hydrogen, fluoro, chloro, bromo, iodo, and methoxy.

In a further aspect, $R^{1e}$ is selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted benzyl, optionally substituted phenoxy, nitro, —$NH_2$, amino, monoalkylamino, and dialkylamino.

In a further aspect, $R^{1e}$ is selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, and cyano. In a further aspect, $R^{1e}$ is selected from hydrogen, fluoro, chloro, bromo, and iodo. In a further aspect, $R^{1e}$ is selected from hydrogen, methyl, ethyl, propyl, and butyl. In a further aspect, $R^{1e}$ is selected from hydrogen, methoxy, ethoxy, propoxy, and butoxy. In a further aspect, $R^{1e}$ is selected from hydrogen, cyano, hydroxy, thiol, alkylthiol, optionally substituted benzyl, and optionally substituted phenoxy. In a further aspect, $R^{1e}$ is selected from hydrogen, nitro, —$NH_2$, amino, monoalkylamino, and dialkylamino. In a further aspect, $R^{1e}$ is selected from hydrogen, fluoro, chloro, bromo, iodo, and methoxy.

b. $R^2$ Groups

In one aspect, $R^2$ is selected from hydrogen, C1-C4 alkyl (e.g., methyl, ethyl, n-propyl, s-propyl, i-propyl, cyclopropyl, n-butyl, s-butyl, i-butyl, t-butyl, and cyclobutyl), and amine protecting group. In a further aspect, $R^2$ is an amine protecting group selected from Fmoc, BOC, Cbz, acetyl, trifluoroacetamide, phthalimide, benzyl, triphenylmethylamine, benzylideneamine, and p-toluenesulfonamide.

c. $R^3$ Groups

In one aspect, $R^3$ is selected from hydrogen and hydroxyl protecting group. In a further aspect, $R^3$ is a hydroxyl protecting group selected from MOM, THP, t-butyl ether, allyl ether, benzyl, TIPDS, TBDMS, TBDPS, acetyl, pivalic acid ester, acetonide, benzoyl, and benzylidene acetal.

d. $R^4$ Groups

In one aspect, $R^4$ is selected from hydrogen, C1-C8 alkyl (e.g., methyl, ethyl, n-propyl, s-propyl, i-propyl, cyclopropyl, n-butyl, s-butyl, i-butyl, t-butyl, cyclobutyl, pentyl, hexyl, heptyl, and octyl), and hydroxyl protecting group, or wherein $R^3$ and $R^4$ together comprise a divalent moiety having a structure represented by a formula:

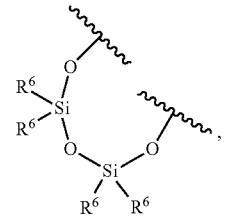

In a further aspect, $R^4$ is a hydroxyl protecting group selected from MOM, THP, t-butyl ether, allyl ether, benzyl, TIPDS, TBDMS, TBDPS, acetyl, pivalic acid ester, acetonide, benzoyl, and benzylidene acetal.

e. $R^5$ Groups

In one aspect, $R^5$ is hydrogen, methyl, ethyl, propyl (e.g., n-propyl, i-propyl, or cyclopropyl), butyl (e.g., n-butyl, s-butyl, i-butyl, t-butyl, or cyclobutyl), pentyl (e.g., n-pentyl, s-pentyl, i-pentyl, neopentyl, or cyclopentyl), or hexyl (e.g., n-hexyl, s-hexyl, i-hexyl, or cyclohexyl).

f. $R^6$ Groups

In one aspect, each $R^6$ is independently selected from methyl, ethyl, propyl (e.g., n-propyl, i-propyl, or cyclopropyl), and butyl (e.g., n-butyl, s-butyl, i-butyl, t-butyl, or cyclobutyl). In a further aspect, each $R^6$ is isopropyl.

5. Example Compounds

In one aspect, a compound can have a structure represented by a formula:

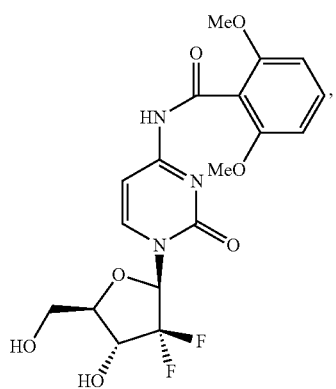
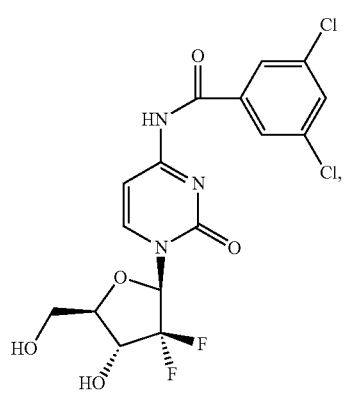
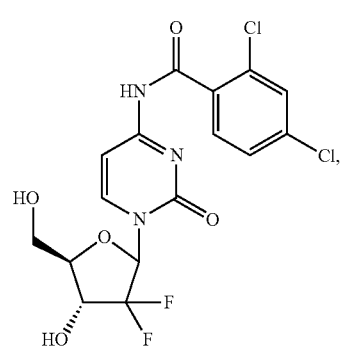
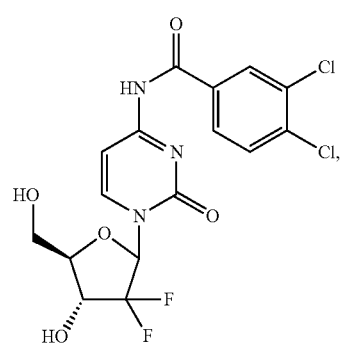
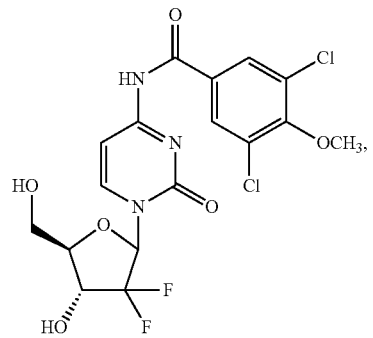
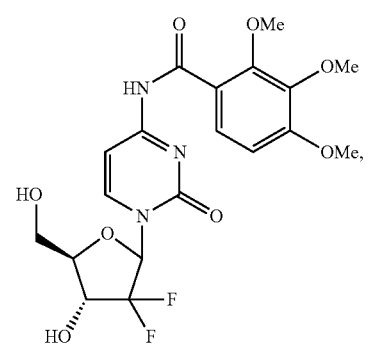
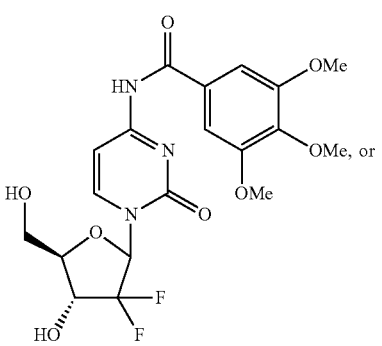
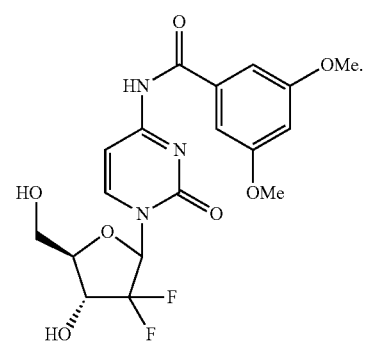
In a further aspect, a compound can have a structure represented by a formula:

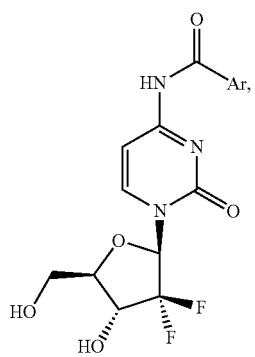
wherein Ar is selected from:
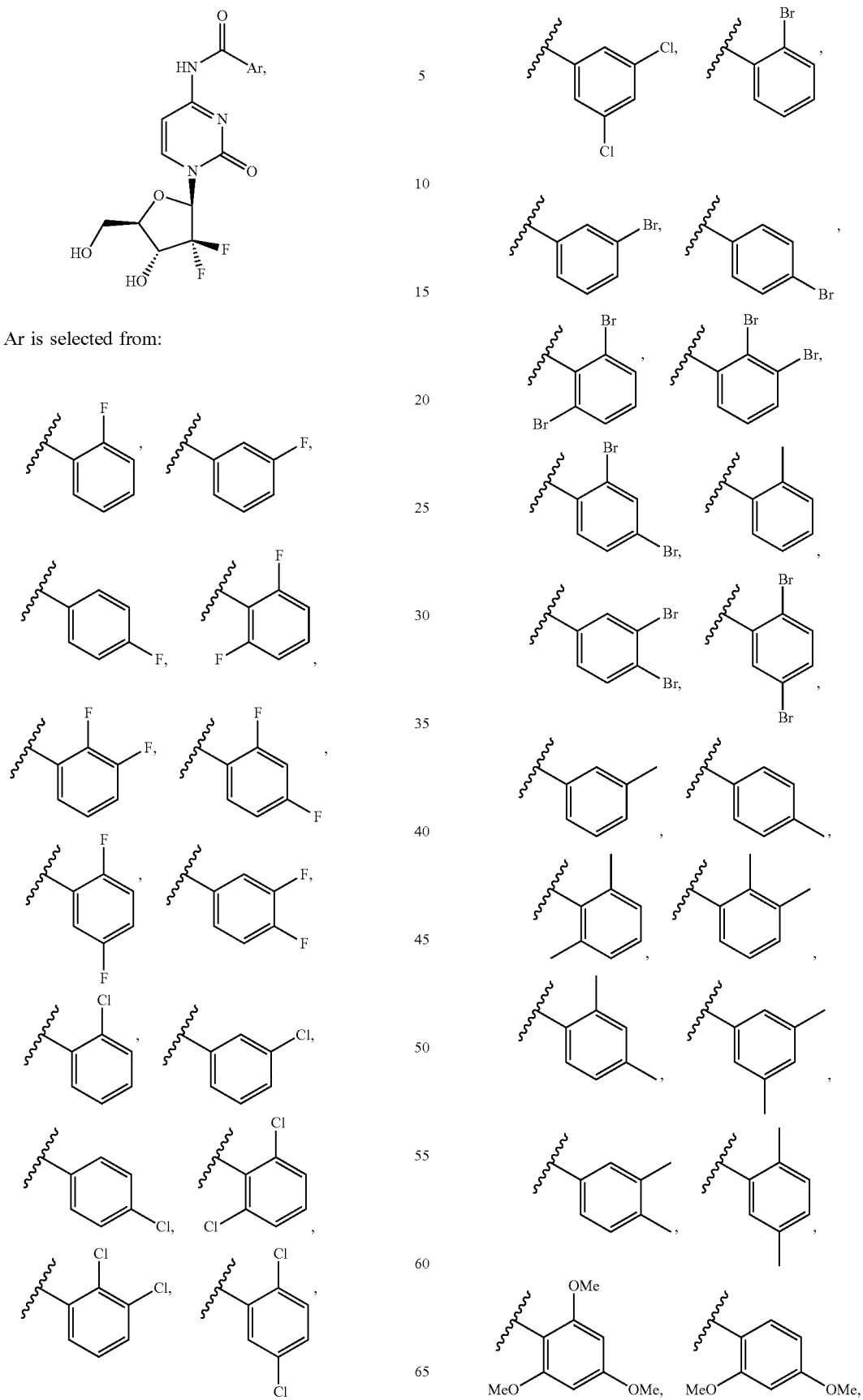

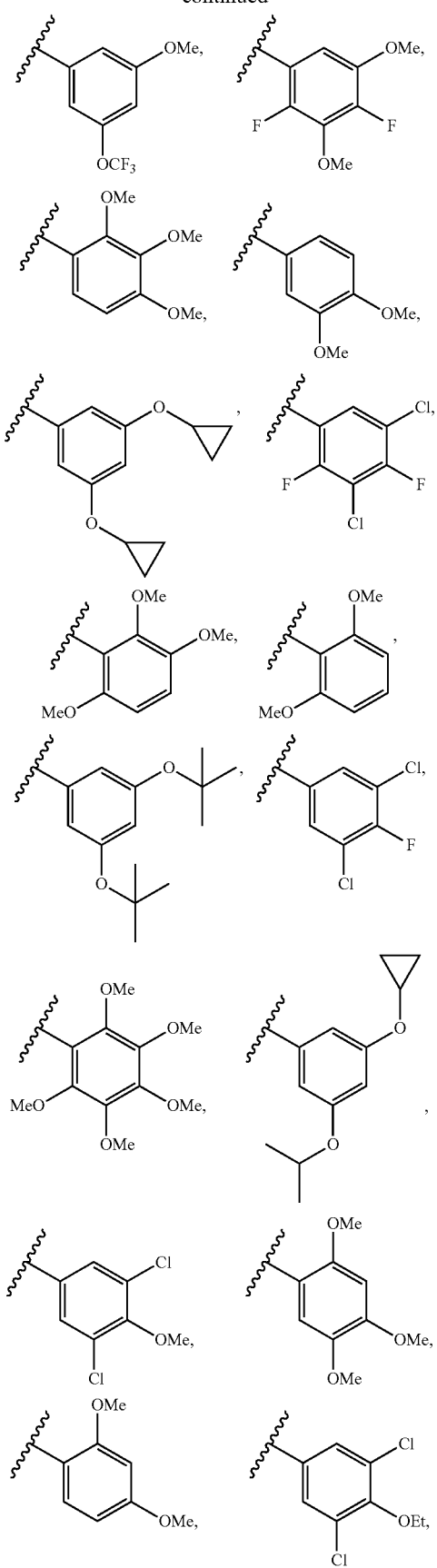
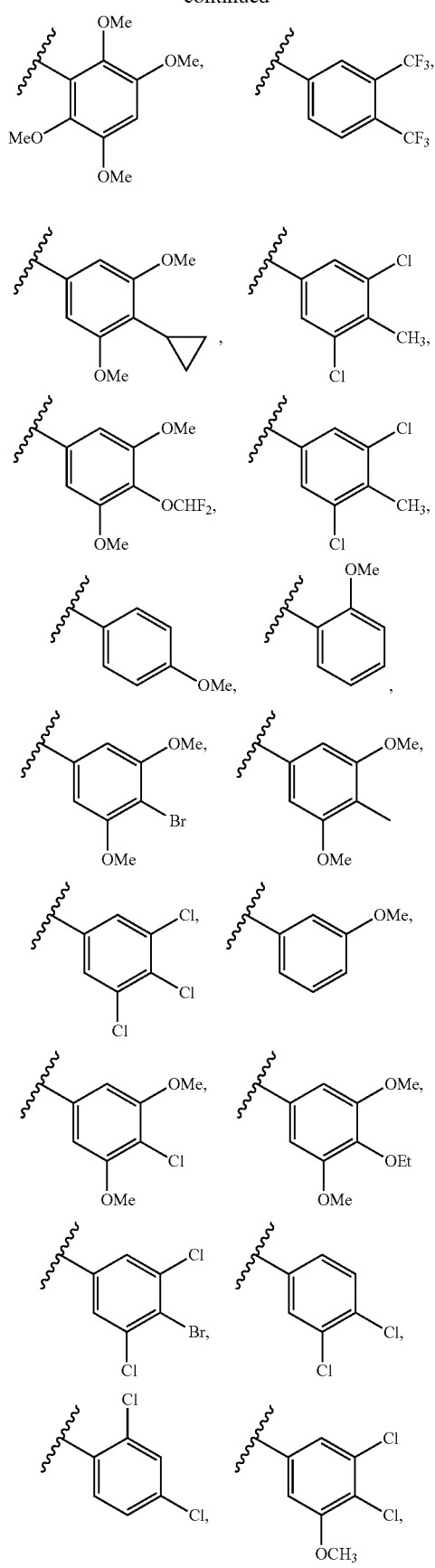

-continued

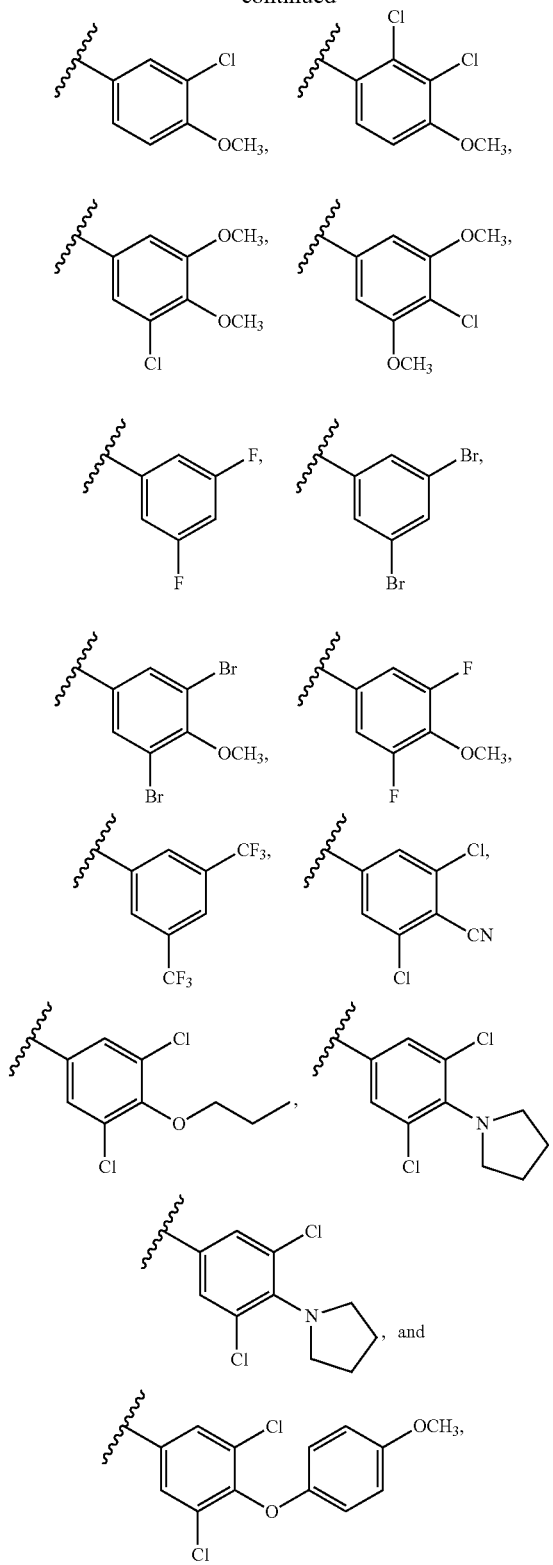

or pharmaceutically acceptable salt, solvate, or polymorph thereof.

It is understood that the disclosed compounds can be used in connection with the disclosed methods, compositions, kits, and uses.

C. Methods of Making the Compounds

In one aspect, the invention relates to methods of making gemcitabine amide analogs, which can be useful in the treatment of cancers and hepatitis. In one aspect, the invention relates to the disclosed synthetic manipulations. In a further aspect, the disclosed compounds comprise the products of the synthetic methods described herein.

1. Synthesis

The compounds of this invention can be prepared by employing reactions as shown in the disclosed schemes, in addition to other standard manipulations that are known in the literature, exemplified in the experimental sections or clear to one skilled in the art. The following examples are provided so that the invention might be more fully understood, are illustrative only, and should not be construed as limiting. For clarity, examples having a fewer substituent can be shown where multiple substituents are allowed under the definitions disclosed herein.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed compositions, kits, and uses.

Thus, in one aspect, the invention relates to a method of making a compound comprising the steps of: (a) providing a first compound having a structure represented by a formula:

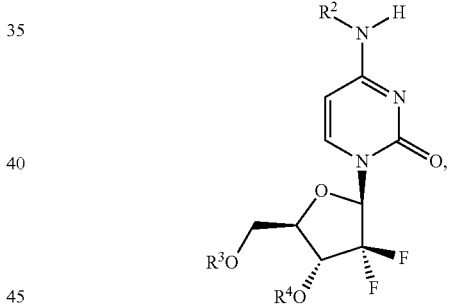

wherein $R^2$ is selected from hydrogen, C1-C4 alkyl, and amine protecting group; wherein $R^3$ is selected from hydrogen and hydroxyl protecting group; and wherein $R^4$ is selected from hydrogen, C1-C8 alkyl, and hydroxyl protecting group, or wherein $R^3$ and $R^4$ together comprise a divalent moiety having a structure represented by a formula:

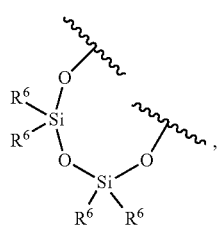

wherein each $R^6$ is independently selected from methyl, ethyl, propyl, and butyl, and (b) reacting with a second compound having a structure represented by a formula:

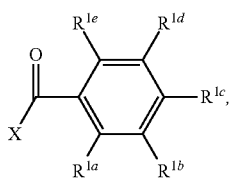

wherein X is halogen or pseudohalogen; wherein 1, 2, 3, 4, or 5 of $R^{1a}$, $R^{1b}$, $R^{1c}$, $R^{1d}$, and $R^{1e}$ are not hydrogen; and wherein each of $R^{1a}$, $R^{1b}$, $R^{1c}$, $R^{1d}$, and $R^{1e}$ is independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, nitro, —NH$_2$, amino, monoalkylamino, dialkylamino, —C(O)R$^5$, —C(O)OR$^5$, —C(O)NHR$^5$, —OC(O)R$^5$, —NHC(O)R$^5$, and —NHC(O)OR$^5$, wherein R$^5$ is hydrogen, methyl, ethyl, propyl, butyl, pentyl, or hexyl, thereby forming an amide bond.

In a further aspect, providing is conversion of R$^2$ from hydrogen to amine protecting group. In a further aspect, providing is conversion of R$^3$ from hydrogen to hydroxyl protecting group. In a further aspect, providing is conversion of R$^4$ from hydrogen to hydroxyl protecting group. In a further aspect, providing is conversion of R$^3$ and R$^4$ from hydrogen to a divalent moiety having a structure represented by a formula:

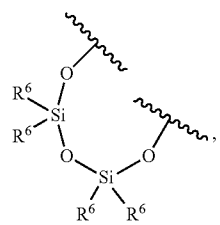

wherein each R$^6$ is independently selected from methyl, ethyl, propyl, and butyl. In a further aspect, providing is accomplished by treatment with TIPDSiCl$_2$.

In a further aspect, the method further comprises the step of deprotecting R$^2$. In a further aspect, the method further comprises the step of deprotecting R$^3$. In a further aspect, the method further comprises the step of deprotecting R$^4$.

In one aspect, Gemcitabine analogs of the present invention can be prepared generically by the synthetic scheme as shown in Scheme 1, below.

SCHEME 1

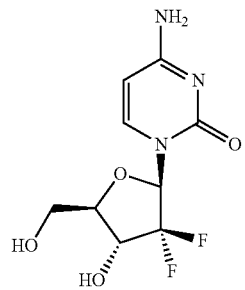

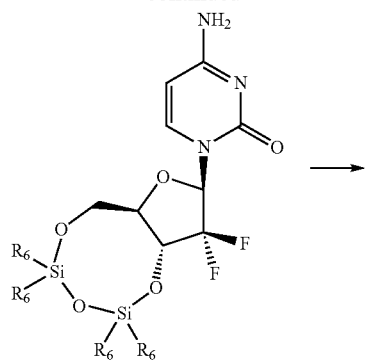

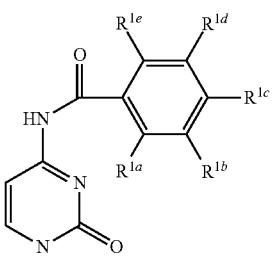

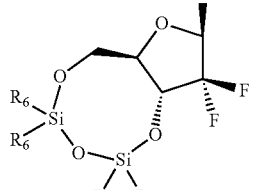

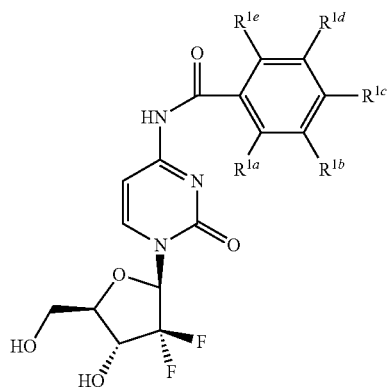

Compounds are represented in generic form, with substituents as noted in compound descriptions elsewhere herein. More specific examples are set forth in FIG. 1.

In one aspect, the first step in the synthetic sequence involves protection of the hydroxyl groups, as shown in Scheme 2a, below.

SCHEME 2A

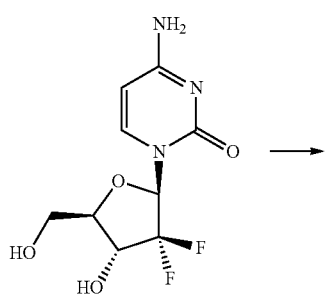

For example, a specific protected Gemcitabine can be prepared as shown in Scheme 2b, below.

SCHEME 2B

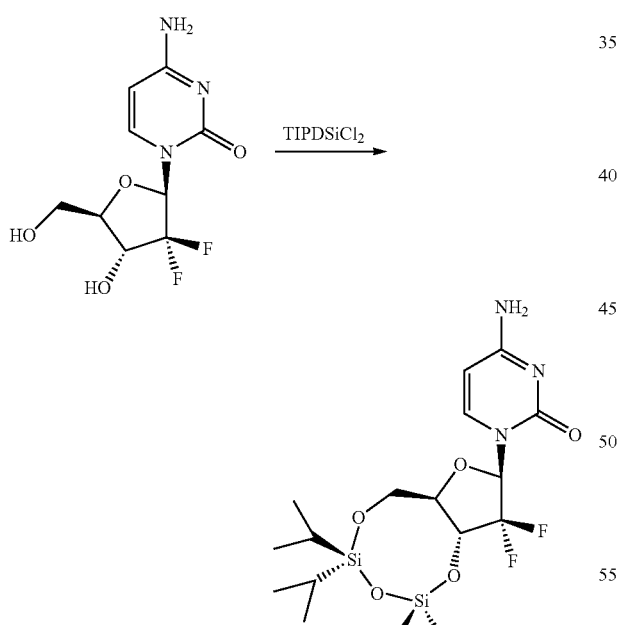

As shown above, Gemcitabine (4-amino-1-((2R,4R,5R)-3,3-difluoro-4-hydroxy-5-(hydroxymethyl)tetrahydrofuran-2-yl)pyrimidin-2(1H)-one) can be treated with 1,3-dichloro-1,1,3,3-tetraisopropyldisiloxane (TIPDSiCl$_2$) in dry pyridine to provide 4-amino-1-((6aR,8R,9aR)-9,9-difluoro-2,2,4,4-tetraisopropyltetrahydro-6H-furo[3,2-f][1,3,5,2,4]trioxadisilocin-8-yl)pyrimidin-2(1H)-one. It is contem- plated that other 1,3-dihalo-1,1,3,3-tetraalkyldisiloxanes can be used in place of TIPDSiCl$_2$. It is also contemplated that two monofunctional halosiloxane protecting groups can be used in place of the difunctional TIPDSiCl$_2$. Further, it is also contemplated that other hydroxyl protecting groups (e.g., tetrahydropyranyl (THP) or acetyl (Ac)) can be used in place of TIPDSiCl$_2$.

In a further aspect, the second step in the synthetic sequence involves formation of an amide moiety, as shown in Scheme 3a, below.

SCHEME 3A

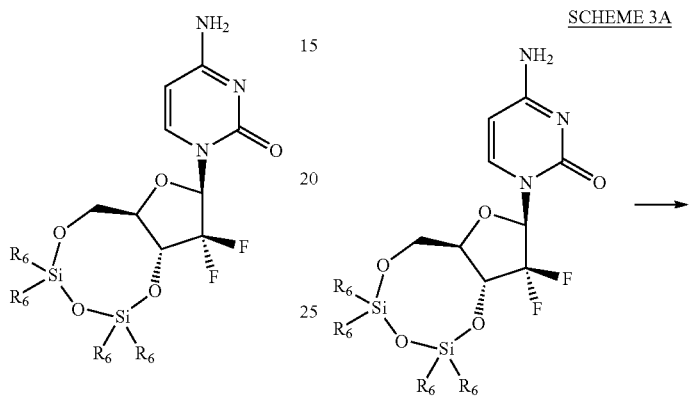

For example, a specific protected Gemcitabine amide analog can be prepared as shown in Scheme 3b, below.

SCHEME 3B

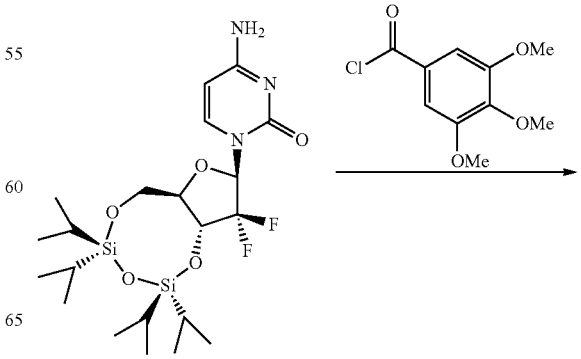

-continued

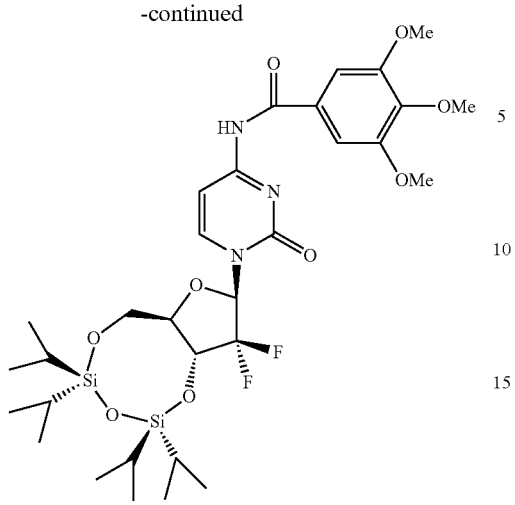

As shown above, a protected Gemcitabine (here, 4-amino-1-((6aR,8R,9aR)-9,9-difluoro-2,2,4,4-tetraisopropyltetra-hydro-6H-furo[3,2-f][1,3,5,2,4]trioxadisilocin-8-yl)pyrimidin-2(1H)-one) can be treated with an appropriate carboxyl chloride (here, 3,4,5-trimethoxybenzoyl chloride) to form an amide bond, thereby providing N-(1-((6aR,8R,9aR)-9,9-difluoro-2,2,4,4-tetraisopropyltetrahydro-6H-furo[3,2-f][1,3,5,2,4]trioxadisilocin-8-yl)-2-oxo-1,2-dihydropyrimidin-4-yl)-3,4,5-trimethoxybenzamide. It is contemplated that other activated carboxyl compounds (e.g., a benzoyl bromide or anhydride) can be used in place of the benzoyl chloride. It is also contemplated that the corresponding carboxyl acid can be used to firm the amide directly with appropriate peptide coupling reagents. Further, it is also contemplated that the product of this transformation can, if desired, be carried into the next step without isolation and/or with minimal or no purification.

In a further aspect, the third step in the synthetic sequence involves deprotection of the hydroxyl groups, as shown in Scheme 4a, below.

SCHEME 4A

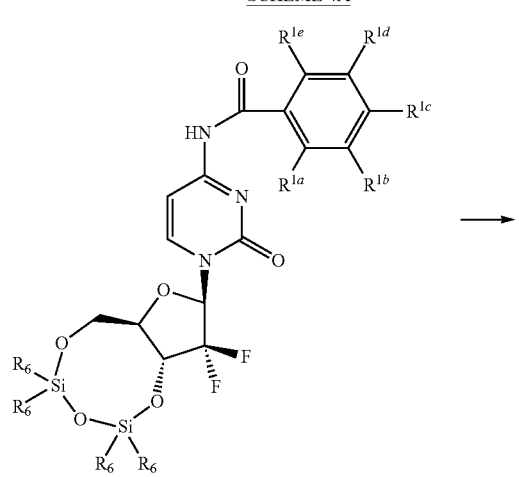

-continued

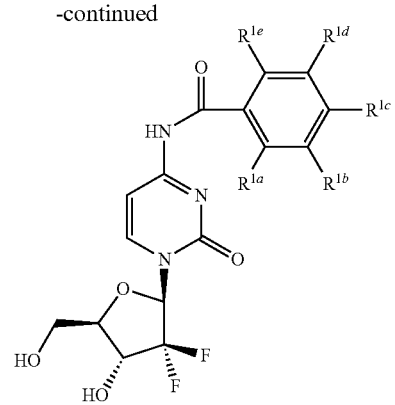

For example, a specific deprotected Gemcitabine amide analog can be prepared as shown in Scheme 4b, below.

SCHEME 4B

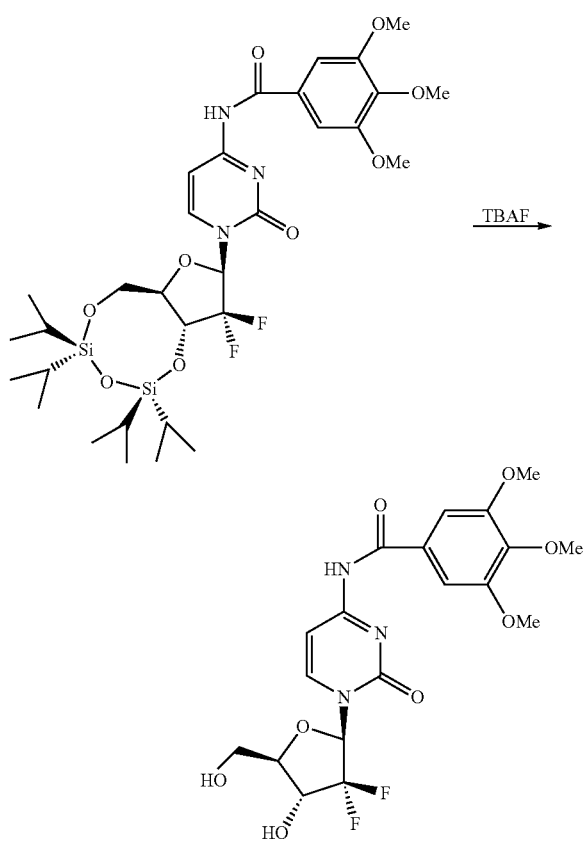

As shown above, a protected Gemcitabine amide analog (here, N-(1-((6aR,8R,9aR)-9,9-difluoro-2,2,4,4-tetraisopropyltetrahydro-6H-furo[3,2-f][1,3,5,2,4]trioxadisilocin-8-yl)-2-oxo-1,2-dihydropyrimidin-4-yl)-3,4,5-trimethoxybenzamide) can be treated with tetrabutylammonium fluoride (TBAF) to liberate the hydroxyl groups. Deprotection provides the corresponding deprotected Gemcitabine amide analog (here, N-(1-((2R,4R,5R)-3,3-difluoro-4-hydroxy-5-(hydroxymethyl)tetrahydrofuran-2-yl)-2-oxo-1,2-dihydropyrimidin-4-yl)-3,4,5-trimethoxybenzamide). It is contemplated that other sources of fluoride ion can be used in place of the TBAF. It is also contemplated that deprotection of the silyl groups can be accomplished with acid. Further, it is also contemplated that other reagents (e.g., acid or base) can be used to liberate the hydroxyl groups when other protecting groups (e.g., tetrahydropyranyl (THP) or acetyl (Ac)) have been employed.

2. Chiral Resolution

The disclosed methods of making can provide compounds that can contain one or more asymmetric centers and, thus, potentially give rise to enantiomers and diastereomers. Unless stated to the contrary, the compounds prepared by the disclosed methods include all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included.

In one aspect, the disclosed methods of making can provide racemic or scalemic mixtures that can be resolved to pure or substantially pure enantiomers using chiral phase chromatography or other suitable methods known to one skilled in the art. As known to one skilled in the art, a variety specific columns and/or mobile phases can affect the desired resolution of enantiomers, and the specific choice can be determined by one skilled in the art. As known to one skilled in the art, chiral chromatography can be carried out in a variety of formats (e.g. SFC, HPLC, and SMB), and other formats can be used to obtain similar results. Moreover, other suitable methods known to one skilled in the art for the separation and isolation of individual enantiomers from a racemic or scalemic mixture can be used to isolate specific enantiomers as needed.

D. Pharmaceutical Compositions

In one aspect, the invention relates to pharmaceutical compositions comprising the disclosed compounds and products of disclosed methods. That is, a pharmaceutical composition can be provided comprising an effective amount of at least one disclosed compound, at least one product of a disclosed method, or a pharmaceutically acceptable salt, solvate, hydrate, or polymorph thereof, and a pharmaceutically acceptable carrier. In a further aspect, the effective amount is a therapeutically effective amount. In a still further aspect, the effective amount is a prophylactically effective amount. In a still further aspect, the pharmaceutical composition comprises a compound that is a product of a disclosed method of making.

In one aspect, the pharmaceutical composition is used to treat a mammal. In a yet further aspect, the mammal is a human. In a further aspect, the mammal has been diagnosed with a need for treatment of the disorder prior to the administering step. In a further aspect, the mammal has been identified to be in need of treatment of the disorder. In a further aspect, the pharmaceutical composition is used to treat a neurological and/or psychiatric disorder. In a yet further aspect, the disorder is a cancer. In a yet further aspect, the disorder is a hepatitis.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, *acacia*, magnesium stearate, and stearic acid. Examples of liquid carriers are sugar syrup, peanut oil, olive oil, and water. Examples of gaseous carriers include carbon dioxide and nitrogen.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

It is understood that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

Thus, in one aspect, the invention relates to a pharmaceutical composition comprising a pharmaceutically acceptable carrier and an effective amount of a disclosed compound or the product of a disclosed method. In a further aspect, the composition further comprises one or more of: (a) a drug known to treat a disorder of uncontrolled cellular proliferation; (b) a substance known to increase risk of uncontrolled cellular proliferation; (c) an antiviral agent; and (d) a substance known to increase risk of viral infection. In a further aspect, the composition further comprises carboplatin.

It is understood that the disclosed compositions can be prepared from the disclosed compounds. It is also understood that the disclosed compositions can be employed in the disclosed methods of using.

E. Methods Of Using The Compounds And Compositions

Also provided is a method of use of a disclosed compound, composition, or medicament. In one aspect, the method of use is directed to the treatment of a disorder. In a further aspect, the disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

The pharmaceutical compositions and methods of the present invention can further comprise other therapeutically active compounds as noted herein which are usually applied in the treatment of the above mentioned pathological conditions.

1. Treatment Methods

The compounds disclosed herein are useful for treating, preventing, ameliorating, controlling or reducing the risk of a variety of disorders, including, for example, viral disorders (e.g., hepatitis) and disorders of uncontrolled cellular proliferation (e.g., cancers).

In one aspect, the disclosed compounds can be used in combination with one or more other drugs in the treatment, prevention, control, amelioration, or reduction of risk of diseases or conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly.

a. Treating a Subject for Viral Infection

In one aspect, the invention relates to a method for treating a subject for viral infection, the method comprising the step of administering to the subject an effective amount of a disclosed compound or the product of a disclosed method or a disclosed pharmaceutical composition. In one aspect, the amount is therapeutically effective. In a further aspect, the amount is prophylactically effective.

In one aspect, the subject is a mammal. In a further aspect, the mammal is a human. In a further aspect, the mammal has been diagnosed with a need for treatment of the infection prior to the administering step. In a further aspect, the method further comprises the step of identifying a mammal in need of treatment of the infection.

In a further aspect, the viral infection is viral hepatitis. In a further aspect, the viral infection is Hepatitis A, Hepatitis B, or Hepatitis C. In a further aspect, the viral infection is dengue virus, Human immunodeficiency virus, Herpes simplex, Cytomegalovirus, Epstein-Barr virus, or Yellow fever.

b. Inhibiting Viral Replication

In one aspect, the invention relates to a method for inhibiting viral replication within at least one cell, the method comprising the step of administering to the cell an effective amount of a disclosed compound or the product of a disclosed method or a disclosed pharmaceutical composition. In one aspect, the cell is a mammalian. In a further aspect, the cell is a human. In a further aspect, administration to the cell is performed in vitro. In a further aspect, administration to the cell is performed in vivo.

In a further aspect, the viral infection is viral hepatitis. In a further aspect, the viral infection is Hepatitis A, Hepatitis B, or Hepatitis C. In a further aspect, the viral infection is dengue virus, Human immunodeficiency virus, Herpes simplex, Cytomegalovirus, Epstein-Barr virus, or Yellow fever.

c. Treating a Disorder of Uncontrolled Cellular Proliferation

In one aspect, the invention relates to a method for treating a disorder of uncontrolled cellular proliferation, the method comprising administering to a subject an effective amount of a disclosed compound or the product of a disclosed method or a disclosed pharmaceutical composition. In one aspect, the amount is therapeutically effective. In a further aspect, the amount is prophylactically effective.

In one aspect, the subject is a mammal. In a further aspect, the mammal is a human. In a further aspect, the mammal has been diagnosed with a need for treatment of the disorder prior to the administering step. In a further aspect, the method further comprises the step of identifying a mammal in need of treatment of the disorder.

In a further aspect, the disorder is cancer. In a further aspect, the disorder is carcinoma. In a further aspect, the disorder is selected from non-small cell lung cancer, pancreatic cancer, bladder cancer, and breast cancer. In a further aspect, the disorder is esophageal cancer. In a further aspect, the disorder is lymphoma.

d. Arresting Tumor Growth

In one aspect, the invention relates to a method for arresting tumor growth, the method comprising administering to at least one tumor cell an effective amount of a disclosed compound or the product of a disclosed method or a disclosed pharmaceutical composition. In one aspect, the cell is a mammalian. In a further aspect, the cell is a human. In a further aspect, administration to the cell is performed in vitro. In a further aspect, administration to the cell is performed in vivo.

In a further aspect, the disorder is cancer. In a further aspect, the disorder is carcinoma. In a further aspect, the disorder is selected from non-small cell lung cancer, pancreatic cancer, bladder cancer, and breast cancer. In a further aspect, the disorder is esophageal cancer. In a further aspect, the disorder is lymphoma.

2. Manufacture of a Medicament

In one aspect, the invention relates to a medicament comprising one or more disclosed compounds; or a pharmaceutically acceptable salt, hydrate, solvate, or polymorph thereof. In a further aspect, the one or more compounds is a product of a disclosed method of making.

Thus, in a further aspect, the invention relates to a method for manufacturing a medicament, the method comprising combining a pharmaceutically acceptable carrier with a disclosed compound or the product of a disclosed method or a disclosed pharmaceutical composition.

It is understood that the disclosed methods can be performed with the disclosed compounds, products, and pharmaceutical compositions. It is also understood that the disclosed methods can be employed in connection with the disclosed methods of using.

3. Use of Compounds

Also provided are the uses of the disclosed compounds and products. In one aspect, the invention relates to use of at least one disclosed compound; or a pharmaceutically acceptable salt, hydrate, solvate, or polymorph thereof. In a further aspect, the compound used is a product of a disclosed method of making.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In a further aspect, the use is associated with the treatment of viral infection (e.g., hepatitis) or disorder of uncontrolled cellular proliferation (e.g., cancer).

It is understood that the disclosed uses can be employed in connection with the disclosed compounds, products of disclosed methods of making, methods, compositions, and kits.

4. Kits

In one aspect, the invention relates to kits comprising at least one disclosed compound; or a pharmaceutically acceptable salt, hydrate, solvate, or polymorph thereof, at least one product of a disclosed method, or at least one disclosed pharmaceutical composition and one or more of:

(a) an antiviral agent;
(b) a substance known to increase risk of viral infection;
(c) instructions for treating a viral infection;
(d) a drug known to treat a disorder of uncontrolled cellular proliferation;
(e) a substance known to increase risk of uncontrolled cellular proliferation; and
(f) instructions for treating a disorder of uncontrolled cellular proliferation.

In a further aspect, the at least one compound and the at least one agent are co-formulated. In a still further aspect, the at least one compound and the at least one agent are co-packaged. The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

In a further aspect, the drug known to treat a disorder of uncontrolled cellular proliferation is carboplatin.

It is understood that the disclosed kits can be prepared from the disclosed compounds, products, and pharmaceutical compositions. It is also understood that the disclosed kits can be employed in connection with the disclosed methods of using.

F. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Synthetic Procedures

Several methods for preparing the compounds of this invention are illustrated in the following Examples. Starting materials and the requisite intermediates are in some cases commercially available, or can be prepared according to literature procedures or as illustrated herein. The Examples are provided herein to illustrate the invention, and should not be construed as limiting the invention in any way. The Examples are typically depicted in free base form, according to the IUPAC naming convention. Examples are provided herein to illustrate the invention, and should not be construed as limiting the invention in any way.

All solvents were dried with solvent-purification system (Innovative Technology, Inc). Analytical TLC was carried out on E. Merck silica gel 60 F254 aluminum-backed plates. The preparation TLC was carried out on silica gel 60 F254 plates (20×20 cm, 1 mm) from EMD Chemicals, Inc. The 230-400 mesh size of the absorbent was utilized for all chromatographic purifications. $^1$H NMR and high-resolution mass spectra were obtained at The Ohio State University Campus Chemical Instrumentation Center.

a. Preparation of 3',5'-O-(1,1,3,3-Tetraisopropyldisiloxane-1,3-dily)gemcitabine (Compound 2 in FIG. 1)

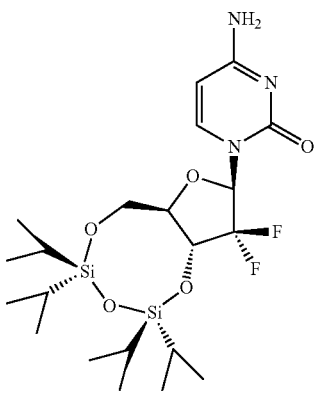

To the solution of gemcitabine (Compound 1 in FIG. 1) (136.6 mg, 0.52 mmol) in dry pyridine (40 mL), 1,3-dichloro-1,1,3,3-tetraisopropyldisiloxane (TIPDSiCl$_2$) (0.17 mL) was added slowly with stirring. The mixture was stirred at room temperature for 48 h. Pyridine was then removed under reduced pressure and the residue was subjected to a silica gel column chromatography, with a gradient of methanol (1-2.5%) in CH$_2$Cl$_2$ to give Compound 2 as a white foam (189.7 mg, 72%).

b. General Procedures for Synthesis of Gemcitabine Derivatives

To the solution of Compound 2 (0.054 mmol, FIG. 1) in dry pyridine (7 mL), the appropriate carboxyl chloride (1.5 eq.) was added slowly with stirring. The mixture was stirred at room temperature for overnight. The solvent was removed and the residue was used to the next reaction without further purification. TBAF (1 M in THF, 0.3 mL) was then added to the solution of the residue and the resulted solution was stirred at room temperature for 1.5 h. After the removal of the solvent, the residue was subjected to silica gel column chromatography, with a stepwise gradient of methanol (1-3%) in CH$_2$Cl$_2$ to give the raw product. The raw product was further purified by semi-preparative HPLC (a gradient of water/methanol for GCB, G2DB, and G3DB or water/acetonitrile for GTB). HPLC fractions containing pure a gemcitabine derivative were lyophilized overnight to yield a dried product with a purity of >99%.

c. N$^4$-(3,4,5-Trimethoxybenzoyl)gemcitabine (GTB)

This compound was prepared according to the above procedure (2 steps from 2), with 3,4,5-trimethoxybenzoyl chloride as the carboxyl chloride, in 62% yield.

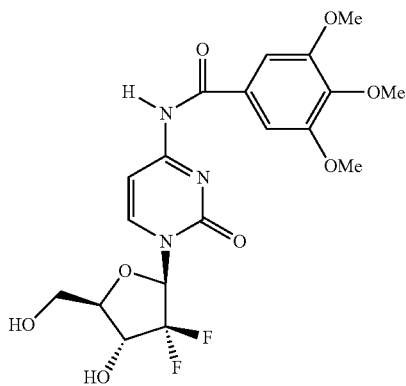

$^1$H NMR (300 MHz, DMSO-d$_6$) 10.79 (s, 1H, NH), 8.34 (br, 1H, H-6), 7.41 (s, 3H, H-5, H—Ar), 6.36 (brs, 1H, OH-3'), 6.12-6.28 (m, 1H, H-1'), 5.35 (s, 1H, OH-5'), 4.31-4.08 (m, 1H, H-3'), 3.86-3.36 (m, 12H, OCH$_3$, H-5', H-4').

d. N$^4$-(3,5-Dichlorobenzoyl)gemcitabine (GCB)

This compound was prepared according to the above procedure (2 steps from 2), with 3,5-dichlorobenzoyl chloride as the carboxyl chloride, in 90% yield.

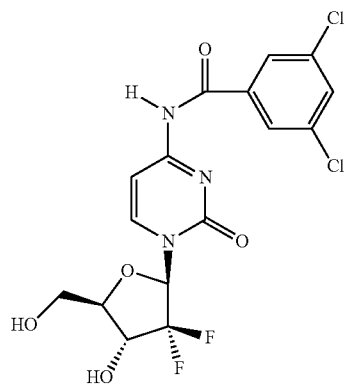

$^1$H NMR (300 MHz, DMSO-$d_6$) 11.05 (s, 1H, NH), 8.33 (d, J=7.3 Hz, 1H, H-6), 8.10-7.78 (m, 3H, H—Ar), 7.42-7.22 (m, 1H, H-5), 6.36 (d, 1H, OH-3'), 6.26-6.10 (m, 1H, H-1'), 5.41-5.30 (m, 1H, OH-5'), 4.30-4.00 (m, 1H, H-3'), 3.72-3.92 (m, 1H, H-4'), 3.80-3.68 (m, 2H, H-5').

e. N$^4$-(2,6-Dimethoxybenzoyl)gemcitabine (G2DB)

This compound was prepared according to the above procedure (2 steps from 2), with 2,6-dimethoxybenzoyl chloride as the carboxyl chloride, in 89% yield.

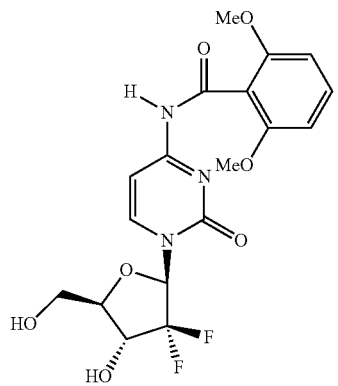

$^1$H NMR (300 MHz, DMSO-$d_6$) 11.21 (s, 1H, NH), 8.30 (d, J=7.3 Hz, 1H, H-6), 7.32-7.10 (m, 2H, H—Ar), 6.85-6.55 (m, 2H, H-5, H—Ar), 6.38 (d, J=6.1 Hz, 1H, OH-3'), 6.20-6.00 (m, 1H, H-1'), 5.41-5.20 (m, 1H, OH-5'), 4.32-4.00 (m, 1H, H-3'), 3.30-3.12 (m, 9H, OCH$_3$, H-5', H-4').

f. N$^4$-(3,5-Dimethoxybenzoyl)gemcitabine (G3Db)

This compound was prepared according to the above procedure (2 steps from 2), with 3,5-dimethoxybenzoyl chloride as the carboxyl chloride, in 88% yield.

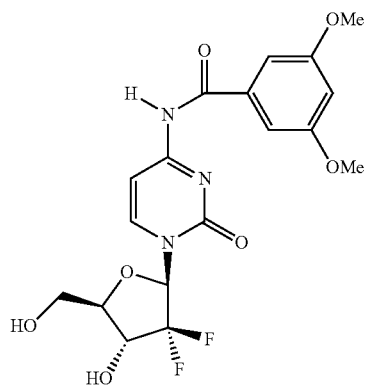

$^1$H NMR (300 MHz, DMSO-$d_6$) 11.22 (s, 1H, NH), 8.31 (d, J=7.3 Hz, 1H, H-6), 7.45-7.22 (m, 2H, H—Ar), 6.81-6.60 (m, 2H, H-5, H—Ar), 6.36 (d, J=6.1 Hz, 1H, OH-3'), 6.24-6.08 (m, 1H, H-1'), 5.41-5.39 (m, 1H, OH-5'), 4.30-4.00 (m, 1H, H-3'), 3.90-3.12 (m, 9H, OCH$_3$, H-5', H-4').

2. Assay Procedures

The following procedures were used to determine various aspects of the disclosed compounds and compositions.

a. Experimental Procedures for IC$_{50}$ Assay

Plating Cells: The Luciferase replicon cell line was passaged when it was at about 70% confluency. The cells were counted by using a hemocytometer and diluted to 1×10$^5$ cells per mL in DMEM+10% FBS+0.25 μg/mL G415. The cells were plated as follows: 100 μL of the cells (10,000 cells) per well in a white-walled 96-well plate. The cells were allowed to attach for 24 hours at 37° C.

Treating the cells: Media (DMEM+2% FBS) was pre-warmed to 37° C.

Stock solutions (100 mM) of HPLC purified gemcitabine analogs (test drug) were diluted to 0.5 mM in DMEM+2% FBS, and this working solution was serially diluted in DMEM+2% FBS+0.5% DMSO, thus keeping the concentration of DMSO in each condition identical. The 96-well plate was removed from the 37° C. incubator, and the media replaced on the plate with the serial dilutions of the test drug. The plate was then returned to 37° C. for 48 h.

The compound solubility in media was as follows: ribavirin, soluble >500 μM; gemcitabine, soluble >500 μM; VV-006, precipitate at 500 μM; VV-007, soluble >500 M; VV-012, soluble >500 μM; VV-013, soluble >500 μM; VV-022, soluble >500 μM; G3DB, soluble >500 μM; GCB, precipitate at 500 μM; GTB, soluble >500 μM; and G3DB, soluble >500 μM.

Luciferase Assay: The Bright-Glo reagent (Promega Corporation, Madison, Wis.) was removed from the −80° C. freezer and allowed to thaw it at 4° C. in the dark. The amount of reagent necessary for the experiment (3.65 mL) was removed, and the remaining reagent was returned to −80° C. The Glo Lysis Buffer and the Bright Glow reagent were allowed to warm to room temperature for 30 min in the dark. The 96 well plate was removed from the incubator and the cells to allowed cool to room temperature for 30 min. The media was removed from the cells, and each well was gently washed in 100 μL of phosphate buffered saline (PBS). The PBS was removed and then 50 μL of the Glo Lysis Buffer was added to each well, followed by gently rocking the plate for 15 min at room temperature in the dark to ensure complete cell lysis. To each well of the 96-well plate was added 50 μL of the Bright Glo reagent and it was mixed well with the lysate. The plate was inserted into a GloMax 96 plate reader and allowed to sit for 5 min in the dark for the luciferase reaction to reach a steady state. The luminescence on the plate was read by using the pre-installed "Bright Glo" Promega program (Synergy Software) and the data were collected and saved. The data were fit to a 4 parameter logistic curve using Kaleidagraph using the following equation: $100/(1+(x/m3)^{\wedge}m4)$.

Representative data for dose response curves and calculated IC$_{50}$ values using the above methods for inhibition of the HCV luciferase replicon in Huh7 cells are shown in FIGS. 5, 6, 7, and 8 for interferon, gemcitabine, GCB, and GTB, respectively.

b. Experimental Procedures for TC$_{50}$ Assay

Plating Cells: The Huh7 cell line was passaged when it was at about 70% confluency. The cells were counted using a hemocytometer, followed by dilution of the cells to 0.5× 10$^5$ cells per mL in DMEM+10% FBS. The cells were plated at 100 μL (5,000 cells) per well in a clear 96-well plate. The cells were allowed to attach for 24 hours at 37° C.

Treating the cells: The media (DMEM media without phenol red+2% FBS media) was pre-warmed to 37° C. The 100 mM stock solutions of the gemcitabine analogs (test drugs) were diluted to an initial working concentration of 0.5 mM in DMEM without phenol red+2% FBS. This provided a final DMSO concentration of 0.5%. The 100 mM stock of 3,5-dichlorobenzoic acid was diluted in DMEM without phenol red+2% FBS to a concentration of 0.5 mM. The working 0.5 mM diluted test drugs were serially diluted in DMEM without phenol red+2% FBS+0.5% DMSO in order to maintain a constant concentration of DMSO in each condition. The 96-well plate was removed from the 37° C. incubator, and the media on the plate was replaced with media containing diluted test drug.

MTS Assay: The reagents from CellTiter 96 kit (Promega Corporation, Madison, Wis.) were thawed at room temperature in the dark for 1 h. The 96-well plate was removed from the 37° C. incubator at 48 h after drug treatment. 20 μL of the combined MTS/PMS reagent to each well of the plate, mixed, and the plate returned to 37° C. The absorbance of each well at 490 nm and 650 nm was determined using the Flexstation 3 microplate reader in endpoint mode every hour for 3 h. The solutions in the wells were mixed prior to each reading. The data were fit to the Emax model: y=(Emax*x)/(TC50+x), where Emax is the maximum inhibition and $TC_{50}$ is the inhibitory dose 50%. Alternatively, the data can be fit to the Emax sigmoidal model: y=(Emax*x^slope)/(TC50^slope+x^slope), where slope is the Hill Slope.

Figure 9:
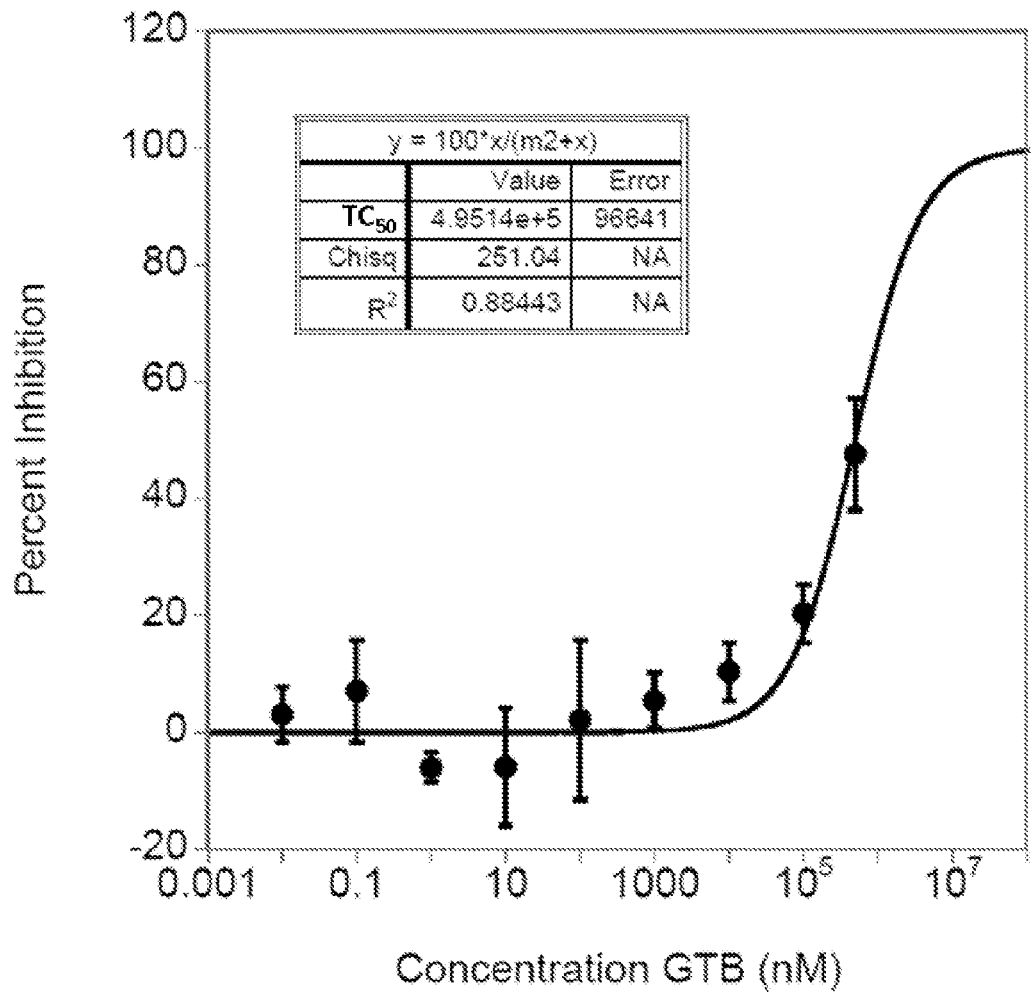
FIG. 9 shows dose-dependent cytotoxicity of a gemcitabine analog GTB. Control Huh7 cells lacking HCV replicon were treated with GTB at concentrations from 0.5 mM to 0.01 nM in triplicate. After 48 hours, the cells were incubated with MTS/PMS. After through mixing, the UV absorbance at 490 nm and 650 nm were recorded by using Flexstation 3 in endpoint. The data were fit to the Emax model: y=(Emax*x)/(TC50+x), where Emax is the maximum inhibition and $TC_{50}$ is the inhibitory dose 50%. The TC50 for GTB is 495±97 μM.
Figure 10:
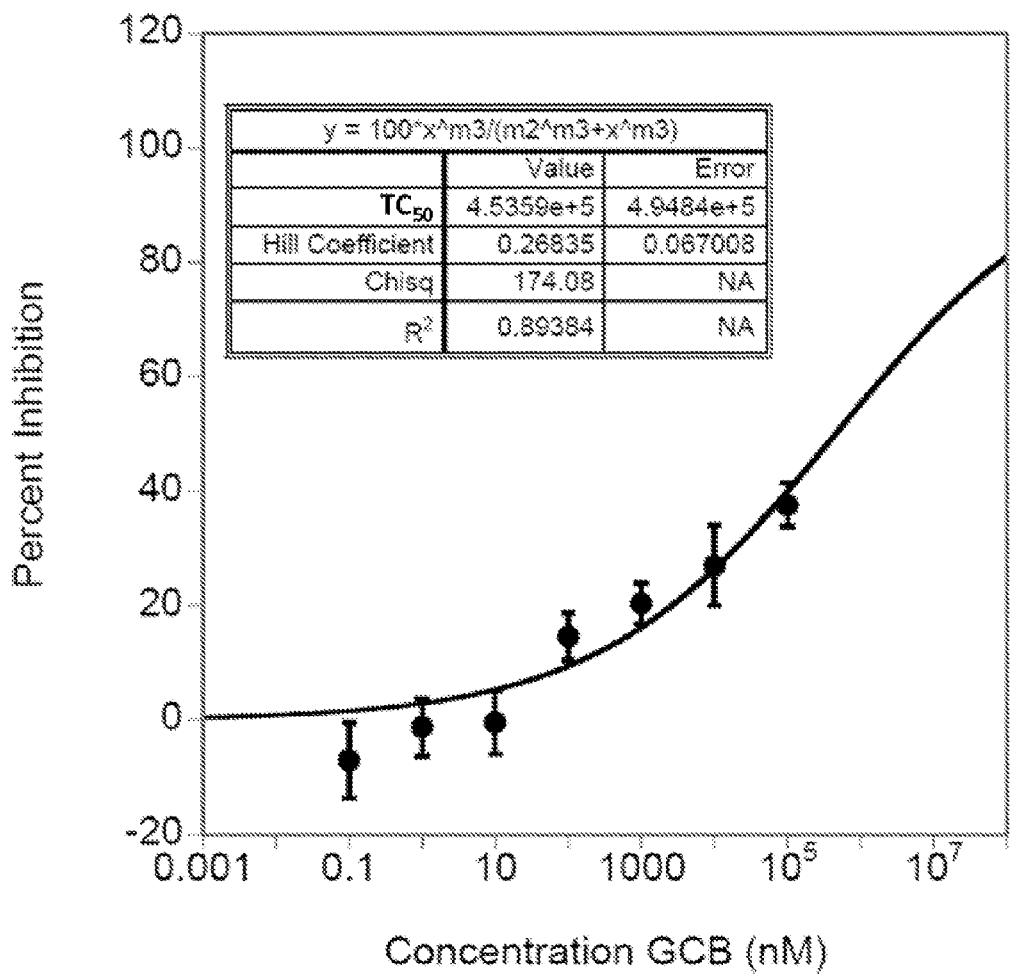
FIG. 10 shows dose-dependent cytotoxicity of a gemcitabine analog GCB. Control Huh7 cells lacking HCV replicon were treated with GCB at concentrations from 0.1 mM to 0.01 nM in triplicate. After 48 hours, the cells were incubated with MTS/PMS. After through mixing, the UV absorbance at 490 nm and 650 nm were recorded by using Flexstation 3 in endpoint mode every hour for 3 hours. The data were fit to the Emax sigmoidal model: y=(Emax*x^α)/(TC50^α+x^α), where Emax is the maximum inhibition, a is the Hill coefficient and TC50 is the inhibitory dose 50%. The $TC_{50}$ for GCB is >100 μM.

Representative dose response data and calculated TC50 values using the above described methods are shown in FIGS. 9 and 10 for GTB and GCB, respectively.

c. $IC_{50}$ and $TC_{50}$ Data for Representative Disclosed Compounds

The $IC_{50}$ and $TC_{50}$ data obtained using the methods described herein above for representative disclosed compounds of the present invention are summarized in Table 1 below. The data in Table 1 were determined for cells exposed to drug for 48 h. The $IC_{50}$ is the concentration of each compound necessary to inhibit the replication of the HCV luciferase replicon to 50%. All gemcitabine analogs were purified by HPLC to provide a purity of $>^{99}$%. Ribavirin and gemcitabine are at least 95% pure and were purchased from ICN and Sigma, respectively.

TABLE 1

ANTIVIRAL ACTIVITY OF RIBAVIRIN, GEMCITABINE AND GEMCITABINE ANALOGS.

| Compound | Structure | $IC_{50}$ (nM) | $TC_{50}$ (μM) | Therapeutic Index ($TC_{50}/IC_{50}$) |
|---|---|---|---|---|
| ribavirin | 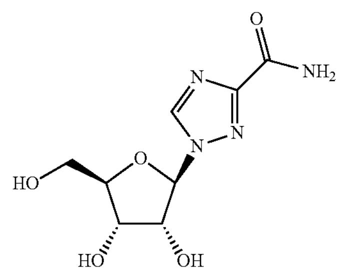 [SMILES: NC(=O)c1ncn([C@@H]2O[C@H](CO)[C@@H](O)[C@H]2O)n1] | 51600 ± 2080 | 527 ± 68.2 | 10.2 |
| gemcitabine | 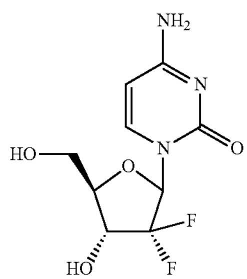 | 58 ± 6 | 35 ± 12 | 597 |
| VV-006 | 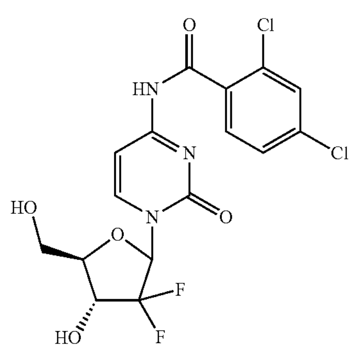 [SMILES: O=C(Nc1ccn(C2O[C@H](CO)[C@@H](O)C2(F)F)c(=O)n1)c1ccc(Cl)cc1Cl] | 77.5 ± 7.0 | >100 | >1290 |

TABLE 1-continued

ANTIVIRAL ACTIVITY OF RIBAVIRIN, GEMCITABINE AND GEMCITABINE ANALOGS.

| Compound | Structure | IC$_{50}$ (nM) | TC$_{50}$ (μM) | Therapeutic Index (TC$_{50}$/IC$_{50}$) |
|---|---|---|---|---|
| VV-007 | 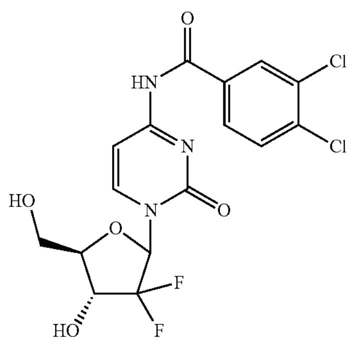 [SMILES: O=C(Nc1ccn(C2O[C@H](CO)[C@@H](O)C2(F)F)c(=O)n1)c1ccc(Cl)c(Cl)c1] | 17.4 ± 1.8 | >100 | >5750 |
| VV-012 | 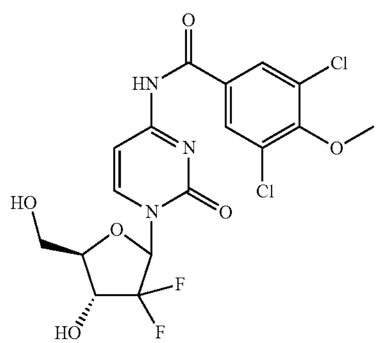 [SMILES: COc1c(Cl)cc(C(=O)Nc2ccn(C3O[C@H](CO)[C@@H](O)C3(F)F)c(=O)n2)cc1Cl] | 19.3 ± 1.6 | >100 | >5180 |
| VV-013 | 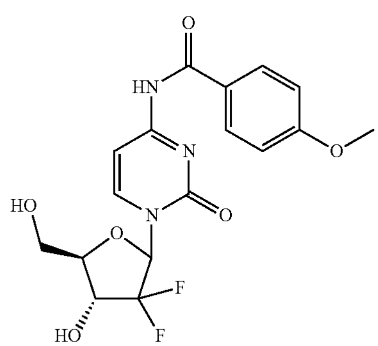 [SMILES: COc1ccc(C(=O)Nc2ccn(C3O[C@H](CO)[C@@H](O)C3(F)F)c(=O)n2)cc1] | 60.0 ± 8.2 | 572 ± 73 | 9530 |
| VV-022 | 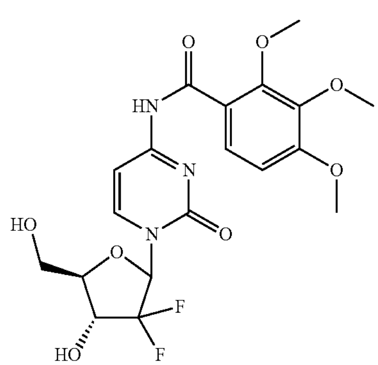 [SMILES: COc1ccc(C(=O)Nc2ccn(C3O[C@H](CO)[C@@H](O)C3(F)F)c(=O)n2)c(OC)c1OC] | 34.6 ± 3.5 | 300 ± 39 | 8670 |

TABLE 1-continued

ANTIVIRAL ACTIVITY OF RIBAVIRIN, GEMCITABINE AND GEMCITABINE ANALOGS.

| Compound | Structure | IC$_{50}$ (nM) | TC$_{50}$ (μM) | Therapeutic Index (TC$_{50}$/IC$_{50}$) |
|---|---|---|---|---|
| VV-033H | 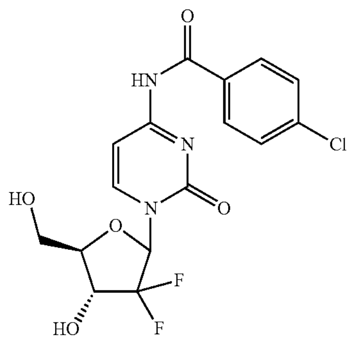 [SMILES: O=C(Nc1ccn(C2O[C@H](CO)[C@@H](O)C2(F)F)c(=O)n1)c1ccc(Cl)cc1] | 37.6 ± 5.4 | 138 ± 28 | 3670 |
| VV-036 | 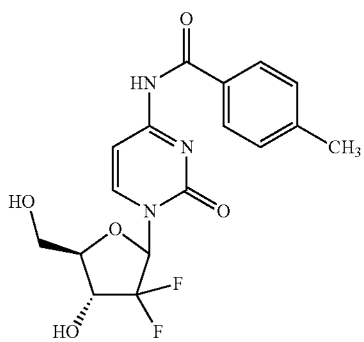 [SMILES: Cc1ccc(C(=O)Nc2ccn(C3O[C@H](CO)[C@@H](O)C3(F)F)c(=O)n2)cc1] | 43.1 ± 4.4 | 329 ± 57 | 7650 |
| VV-038 | 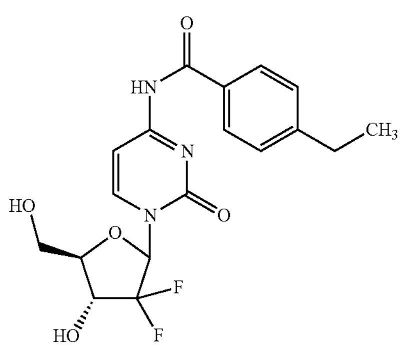 [SMILES: CCc1ccc(C(=O)Nc2ccn(C3O[C@H](CO)[C@@H](O)C3(F)F)c(=O)n2)cc1] | 58.4 ± 9.9 | 492 ± 58 | 8430 |
| G2DB | 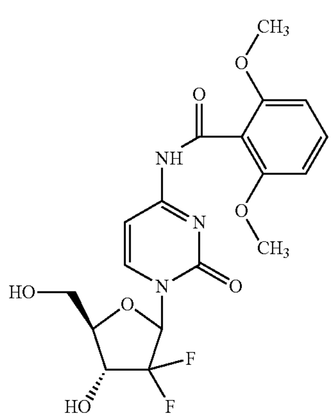 [SMILES: COc1cccc(OC)c1C(=O)Nc1ccn(C2O[C@H](CO)[C@@H](O)C2(F)F)c(=O)n1] | 451 ± 37 | 4580 ± 1100 | 10155 |

TABLE 1-continued

ANTIVIRAL ACTIVITY OF RIBAVIRIN, GEMCITABINE AND GEMCITABINE ANALOGS.

| Compound | Structure | $IC_{50}$ (nM) | $TC_{50}$ (µM) | Therapeutic Index ($TC_{50}/IC_{50}$) |
|---|---|---|---|---|
| G3DB | (structure) | 73.4 ± 12.0 | 962 ± 110 | 13100 |
| GCB | (structure) | 25.5 ± 2.2 | 110 ± 36 | 4310 |
| GTB | (structure) | 49.3 ± 8.8 | 495 ± 97 | 10040 | d. Experimental Procedures for TC50 Assays with Human Cancer Cell Lines

Plating Cells: The Huh7, HEPG2, HEK293, MCF-7, PK9, RPK9, or BxPC3 cells were passaged when they were about 70% confluent. The cells were counted using a hemocytometer, and then diluted cells to $0.5 \times 10^5$ cells per mL in DMEM+10% FBS. 100 µL of the cells (5,000 cells) were plated per well in a clear 96-well plate. The cells were allowed to attach for 24 hours at 37° C.

Treating the cells: Pre-warm the DMEM media without phenol red+2% FBS media to 37° C. Dilute the 100 mM stocks of the gemcitabine analogs to 0.5 mM in DMEM without phenol red+2% FBS. This will bring the final DMSO concentration to 0.5%. Use these 0.5 mM dilutions to further serially the drugs in DMEM without phenol red+2% FBS+0.5% DMSO. This will keep the concentration of DMSO in each condition identical. Remove the 96-well plate from the 37° C. incubator. Replace the media on the plate with the dilutions of the drugs. Stagger these treatments by 1 h and write the treatment time on each set of plates. Return to 37° C. for 48 h or 96 h as indicated.

MTS Assay: The reagents from CellTiter 96 kit (Promega Corporation, Madison, Wis.) were thawed at room temperature in the dark for 1 h. The 96-well plate was removed from the 37° C. incubator at 48 h after drug treatment. 20 µL of the combined MTS/PMS reagent to each well of the plate, mixed, and the plate returned to 37° C. The absorbance of each well at 490 nm and 650 nm was determined using the Flexstation 3 microplate reader in endpoint mode every hour for 3 h. The solutions in the wells were mixed prior to each reading. Fit Data to the Emax model: y=(Emax*x)/(TC50+x), where Emax is the maximum inhibition and TC50 is the inhibitory dose 50%. Alternatively, fit the data to the Emax sigmoidal model: y=(Emax*x^slope)/(TC50^slope+x^slope), where slope is the Hill Slope.

Figure 2:
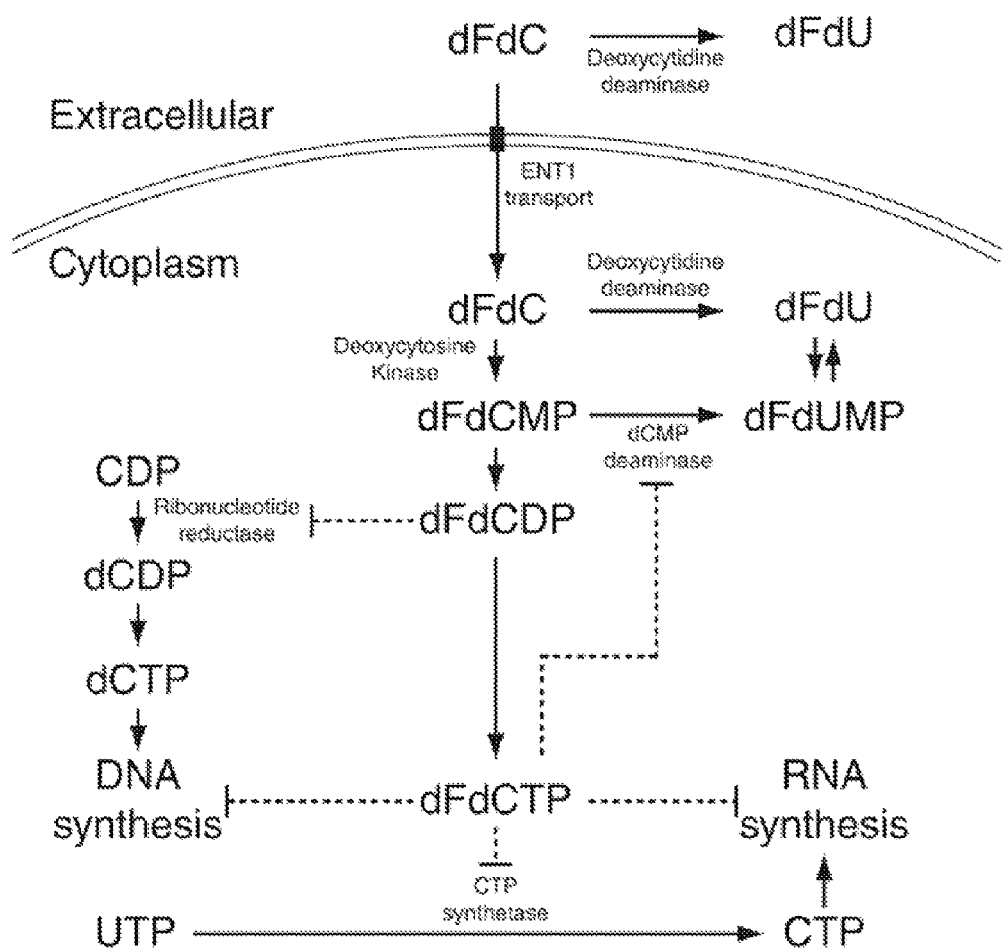
FIG. 2 shows cellular gemcitabine activation and self-potentiation pathways. Dashed lines lead to enzyme inhibition. Gemcitabine is denoted as dFdC.

The data obtained by methods described herein above are summarized in Tables 2, 3, and 4 below. It should be noted that data in Table 2 were obtained after 96 h of test drug treatment, whereas the data in Tables 3 and 4 were obtained after 48 h of test drug treatment. Each $TC_{50}$ was the average value of three measurements as described herein. The data in Table 3 compare the $TC_{50}$ in PK9 versus RPK9 cells. The RPK9 cells are deficient in deoxycytidine kinase ("dCK") activity, an enzyme required for the initial phosphorylation of dFdC to dFdCMP (see FIG. 2). Without wishing to be bound by a particular theory, once gemcitabine or one of the disclosed compounds is converted to dFdC, the presence of active dCK is required for activation of the compound. The data in Table 4 were obtained in the presence and absence of 10 µM S-(4-nitrobenzyl)-6-thioinosine (indicated as "NBTI" in the table), an hENT1 inhibitor. hENT1 is human equilibrative nucleoside transporter 1, a member of the equilibrative nucleoside transporter family. The data show that inhibition of this membrane transporter significantly increases the $TC_{50}$ for gemcitabine, but does not appreciably change the $TC_{50}$ value of either VV-036 or VV-038, which are two representative disclosed gemcitabine analogs. Without wishing to be bound by a particular theory, these data suggest that gemcitabine principally enters cells via the hENT1 transporter, whereas the two representative disclosed gemcitabine analogs enter cells via a different pathway.

TABLE 4

TOXICITY OF GEMCITABINE AND ITS ANALOGS IN HUH7 CELL LINES IN THE PRESENCE OR ABSENCE OF NBTI.*

| Test Compound | $TC_{50}$ (µM) in Huh7 cells | |
| --- | --- | --- |
| | Control** | NBTI*** |
| Gemcitabine | 35 ± 12 | >500 |
| VV-036 | 329 ± 57 | 240 ± 40 |
| VV-038 | 492 ± 58 | 360 ± 80 |

*48 h drug treatment.
**"Control" indicates that no hENT1 inhibitor was added with the test compound.
***"NBTI" indicates that 10 µM of S-(4-nitrobenzyl)-6-thioinosine was added at the same time as the test compound.

e. Time Courses of HCV Luciferase Replicon Inhibition by 500 nM Gemcitabine, GCB and GTB Plating Cells: The luciferase replicon cell line was passaged when it was at about 70% confluency. The cells were counted using a hemocytometer, and then diluted to $1\times10^5$ cells/mL in DMEM with 10% FBS and 0.25 µg/mL G415. 100 µL of the cells (10,000 cells) were plated per well in a white-walled 96-well plate according to the template on the following page. The cells were allowed to attach for 24 hours at 37° C.

Treating the cells: Media (DMEM with 2% FBS) was pre-warmed to 37° C. Stock solutions (0.5 mM) of gemcitabine and HPLC purified GCB or GTB were diluted in DMEM with 2% FBS to 500 nM. The 96-well plate with cells plated as above was removed from the 37° C. incubator, and the media on the plate was replaced with the media containing 500 nM of each drug, or media alone (DMEM+2% FBS+0.5% DMSO). Immediately harvest cells for the first time point by washing the cells in 100 µL of PBS. Cells were lysed by addition of 50 µL of the Glo Lysis Buffer. The cells with Glo-Lysis Buffer were gently rocked for exactly 10 min to allow for complete cell lysis. Using a pipette, the lysis buffer was pipetted in and out three times to mix, and then transferred to separate microfuge tubes. The tubes were snap frozen in liquid nitrogen and store at −80° C. The plate

TABLE 2

TOXICITY OF GEMCITABINE AND ITS ANALOGS IN HUMAN CANCER CELL LINES.*

| Compound | Huh7 (µM) | HEPG2 (µM) | HEK293 (µM) | MCF-7 (µM) | BxPC3 (µM) |
| --- | --- | --- | --- | --- | --- |
| Gemcitabine | 3.41 ± 1.36 | 0.311 ± 0.055 | 0.56 ± 0.13 | 0.067 ± 0.014 | 0.0029 ± 0.0003 |
| GCB | 4.17 ± 1.06 | 0.633 ± 0.207 | 1.19 ± 0.18 | 0.326 ± 0.088 | n.d.** |
| GTB | 5.05 ± 1.22 | 1.67 ± 0.42 | 1.28 ± 0.26 | 0.566 ± 0.118 | n.d. |
| G3DB | 18.5 ± 5.32 | 3.86 ± 1.42 | 4.02 ± 0.79 | 1.57 ± 0.338 | n.d. |

*96 h drug treatment.
**"n.d." indicates that the parameter was not determined.

TABLE 3

TOXICITY OF GEMCITABINE AND ITS ANALOGS IN PK9 AND RPK9 CELL LINES.*

| Test Compound | $TC_{50}$ (µM) PK9 cells | $TC_{50}$ (µM) RPK9 cells |
| --- | --- | --- |
| gemcitabine | 0.095 ± 0.035 | >500 |
| GTB | 1.69 ± 0.10 | >500 |

*48 h drug treatment.

was returned to the 37° C. incubator, and removed to harvest cells as described in the preceding at the following time points: 3 h, 6 h, 9 h, 12 h, 24 h, 48 h, 72 h, 96 h and 120 h, or as otherwise indicated in the figures.

Luciferase Assay: The tubes of cell lysates were removed from the −80° C. freezer, thawed on ice, mixed gently after thawing, and briefly centrifuged. 40 µL of each sample was transferred to a white-walled 96 well plate, followed by addition of 40 µL Bright Glo reagent to each well of the 96-well plate. The lysate and Bright Glo reagent were then mixed well. The plate was inserted into a GloMax 96 plate reader and allowed it to sit for 5 min in the dark for the luciferase reaction to reach a steady state. The luminescence on the plate was then read using the pre-installed "Bright Glo" Promega program.

Figure 3:
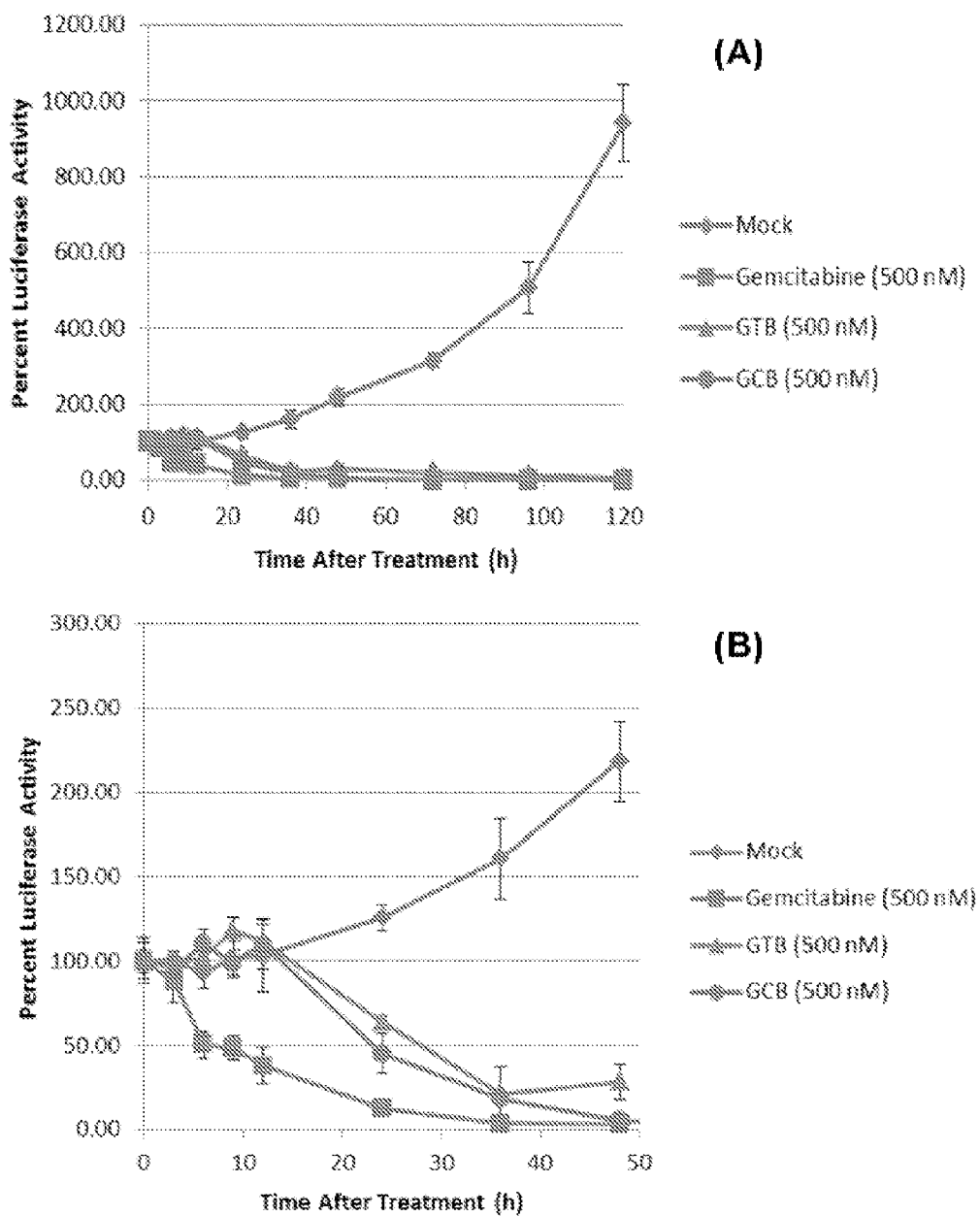
FIG. 3 shows time courses of HCV luciferase replicon inhibition by 500 nM Gemcitabine, GTB, or GCB. Huh7 cells containing the HCV luciferase replicon were treated with media alone (indicated in the figure as "mock"), GCB (500 nM), GTB (500 nM), or gemcitabine (500 nM). After various hours, the cells were lysed, and the total luciferase activity was determined. Panel A shows the full time course, whereas Panel B shows an inset of the top figure for the time range 0-50 h after treatment.
Figure 11:
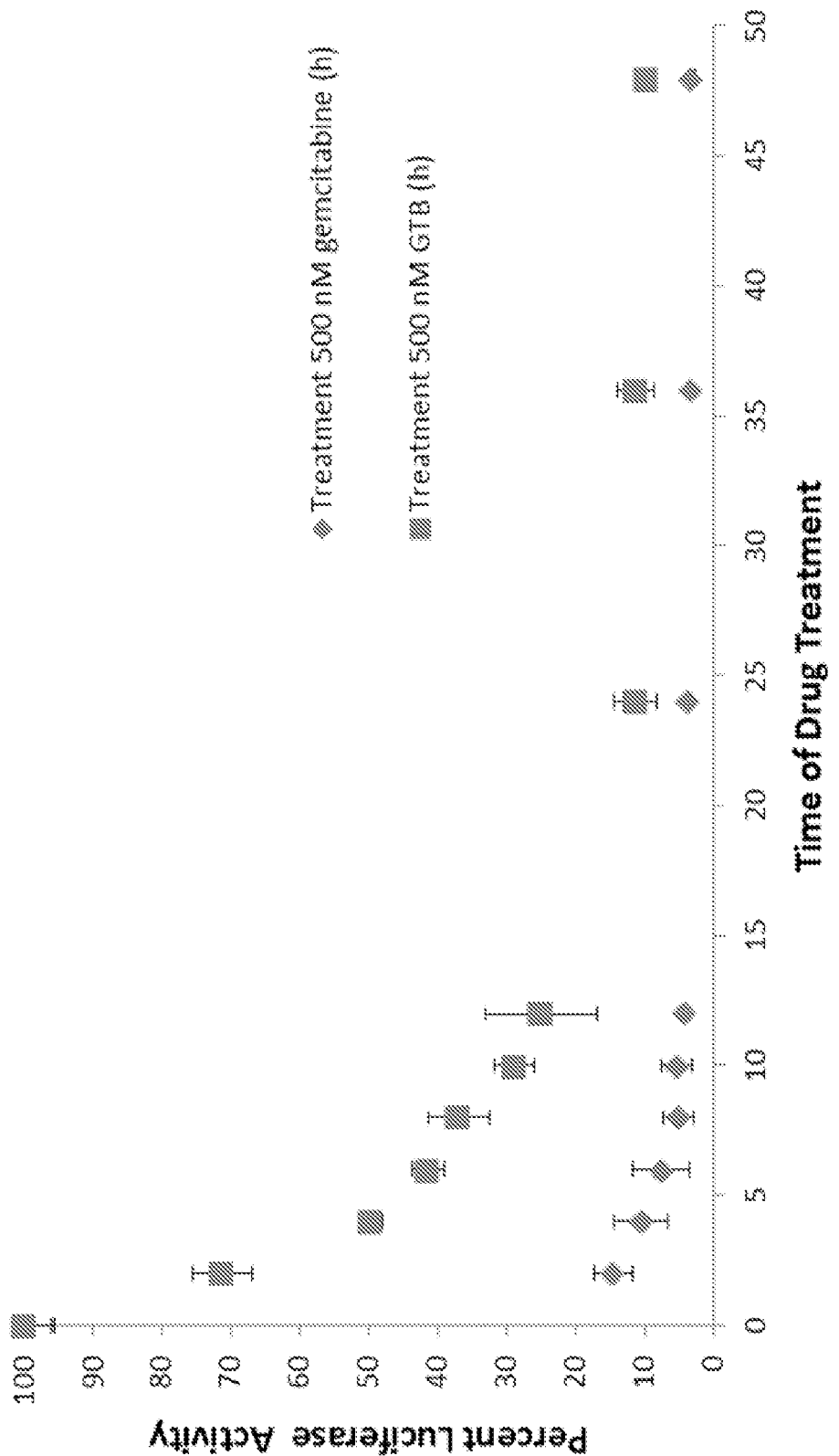
FIG. 11 shows a representative time course of HCV luciferase replicon inhibition by gemcitabine or GTB. Huh7 cells containing the HCV luciferase replicon were mock treated, or treated with gemcitabine (500 nM) or GTB (500 nM). At various times as indicated (i.e. each time point, or t), the media containing the drug was removed, the cells were washed once with PBS and fresh media without drug was applied to the cells. The cells were incubated for a total time of 48 h, thus the amount of time grown in the presence of drug is as the indicated time on the figure (t) and the time grown in absence of drug after drug exposure was 48−t. The cells were then simultaneously lysed and assayed for luciferase activity. The relative luciferase activity in each condition is plotted as a percentage of the mock treated control.
Figure 12:
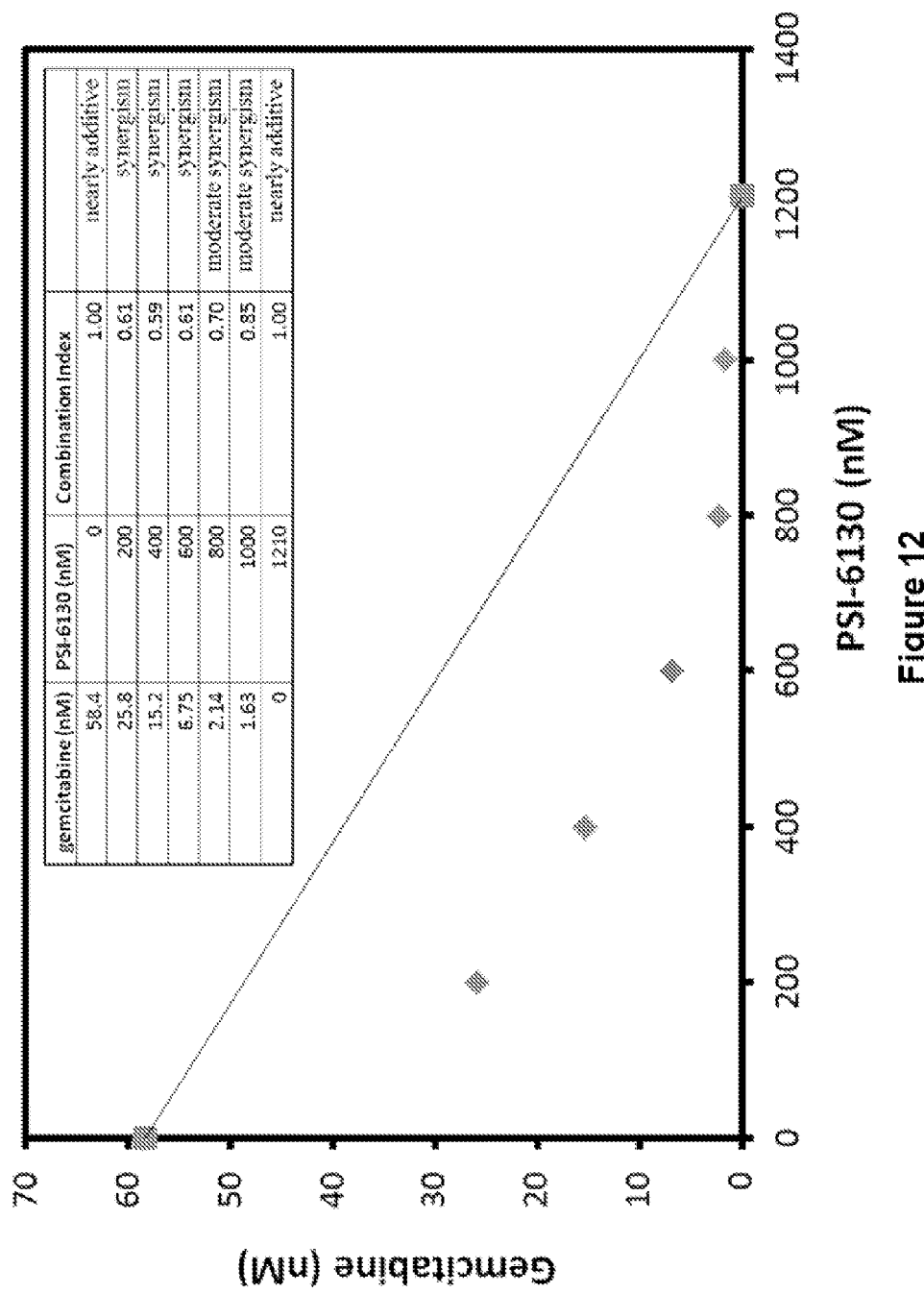
FIG. 12 shows representative data for $IC_{50}$ isobologram analysis of gemcitabine and PSI-6130. The table inset shows the combination index (with associated level of synergism) for the indicated concentrations of gemcitabine and PSI-6130.
Figure 13:
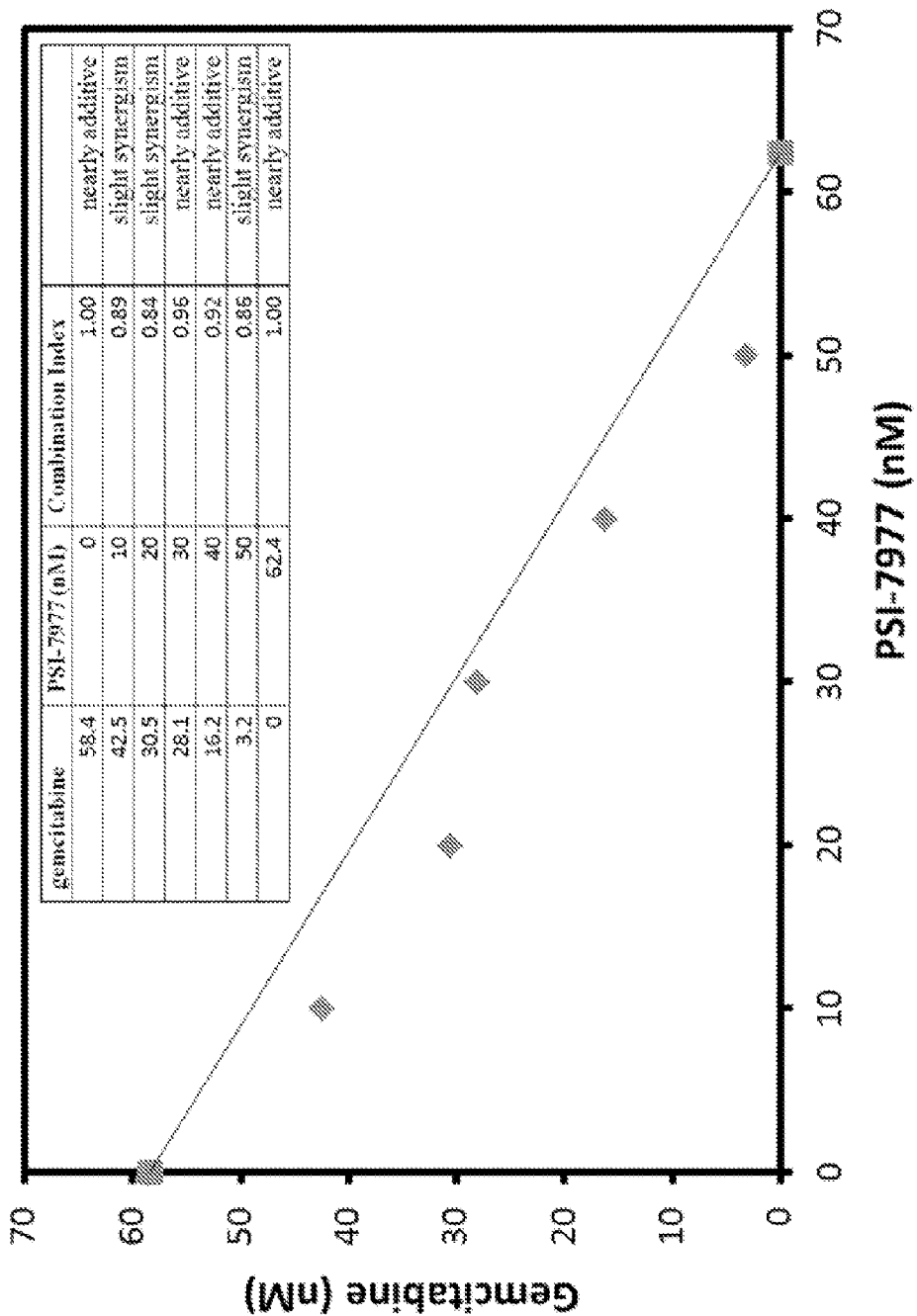
FIG. 13 shows representative data for $IC_{50}$ isobologram analysis of gemcitabine and PSI-7977. The table inset shows the combination index (with associated level of synergism) for the indicated concentrations of gemcitabine and PSI-7977.
Figure 14:
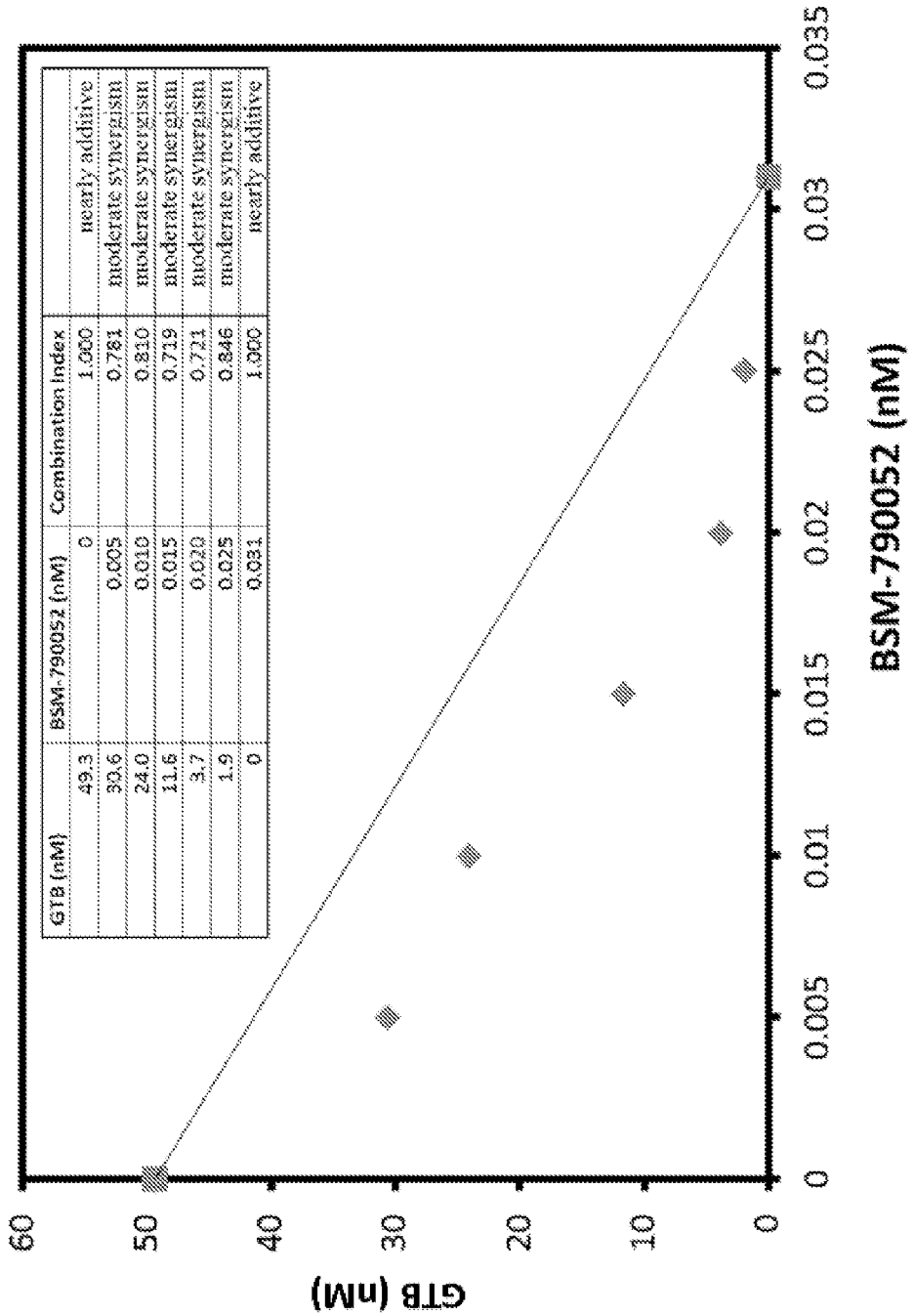
FIG. 14 shows representative data for $IC_{50}$ isobologram analysis of GTB and BSM-790052. The table inset shows the combination index (with associated level of synergism) for the indicated concentrations of gemcitabine and BSM-790052.
Figure 15:
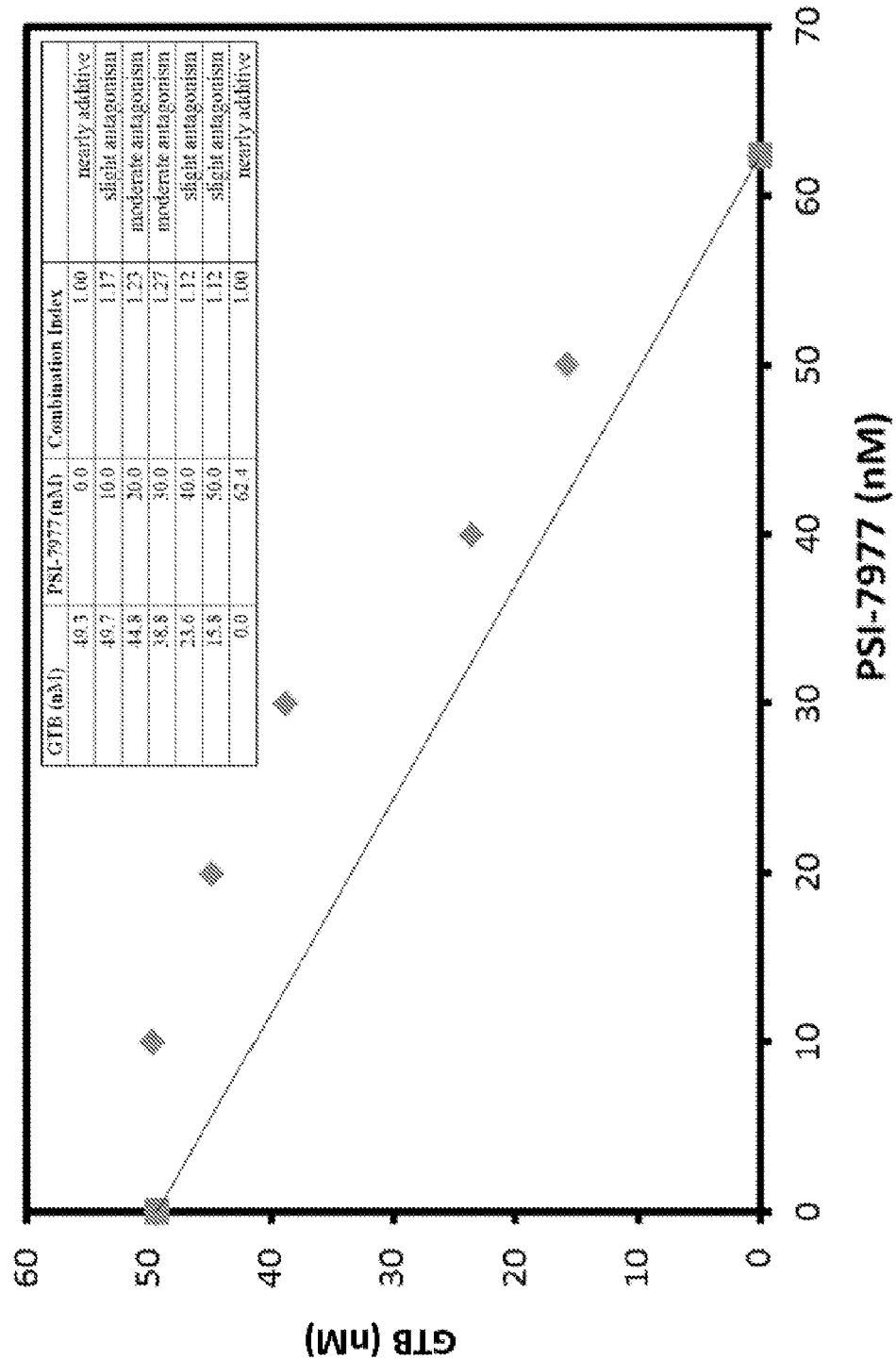
FIG. 15 shows representative data for $IC_{50}$ isobologram analysis of GTB and PSI-7977. The table inset shows the combination index (with associated level of synergism) for the indicated concentrations of gemcitabine and PSI-7977.

The data obtained are shown in FIG. 3. Data shown in FIG. 11 were obtained using similar methods, except that Huh7 cells containing the HCV luciferase replicon were mock treated, or treated with gemcitabine (500 nM) or GTB (500 nM). At various times (t hours), the media containing the drug was removed and the cells were then processed differently in the two figures. In FIG. 3, the cells were stored at −80° C. for lysis. In FIG. 11, the cells were washed once with PBS and fresh media without drug was applied to the cells for the remaining growth hours (48−t). Finally, the cells from both figures were simultaneously lysed and assayed for luciferase activity. The relative luciferase activity in each condition is plotted as a percentage of the mock treated control.

Using the methods described herein above, a comparison of the potency of gemcitabine and GTB was assessed by incubation of cells with test drug for 2 h versus 48 h. That is, the cells were exposed to drug for 2 h at 37° C., followed by 46 h at 37° C. or incubated in the presence of drug for 48 h at 37° C. The data are shown in Table 5 below. The data show that gemcitabine had a modestly enhanced $IC_{50}$, whereas GTB had a significantly enhanced $IC_{50}$, when incubated for 48 h continuously compared to exposure to test drug for only 2 h.

TABLE 5

Comparison of the potency of test compounds-48 h vs. 2 h treatment.

| Compound | $IC_{50}$ (nM)* | $IC_{50}$ (nM)** | Ratio 2 h treatment/48 h treatment |
|---|---|---|---|
| Gemcitabine | 58.4 ± 6.1 | 170.0 ± 33 | 2.9 |
| GTB | 49.3 ± 8.8 | 2770 ± 265 | 56 |

*Cells incubated with drug continuously for 48 h.
**Cells incubated with drug for 2 h, followed by 46 h without drug.

f. Testing HPLC Purified GTB for the Inhibition of the HCV Luciferase Replicon in the Presence of Carboxylesterase Inhibitors (100 mM Benzil or BNPP).

Plating Cells: The luciferase replicon cell line was passaged when it was at about 70% confluency. The cells were counted using a hemocytometer, and then diluted to $1 \times 10^5$ cells/mL in DMEM with 10% FBS and 0.25 µg/mL G415. 100 µL of the cells (10,000 cells) were plated per well in a white-walled 96-well plate according to the template on the following page. The cells were allowed to attach for 24 hours at 37° C.

Treating the cells: Media (DMEM with 2% FBS) was pre-warmed to 37° C. Stock solutions (100 mM) of Benzil and BNPP were diluted in DMEM with 2% FBS to 100 M. The 96-well plate with cells plated as above was removed from the 37° C. incubator, and the media on the plate was replaced with 50 µL of media containing 100 µM of the diluted carboxylesterase inhibitors, or media alone (DMEM+2% FBS). The cells were returned to 37° C. for 1 h. As the cells were incubating with 100 µM of the diluted carboxylesterase inhibitors, stock solutions (100 mM) of gemcitabine and HPLC purified GCB or GTB were diluted in DMEM with 2% FBS to 1.0 mM. The 1.0 mM dilution of GCB or GTB in DMEM+2% FBS+100 µM Benzil or BNPP was serially diluted in DMEM with 2% FBS, 0.5% DMSO, 100 µM benzil or BNPP. At the end of the 1 h incubation, the 96-well plate with cells plated as above was removed from the 37° C. incubator, and 50 µL media diluted test drug and 100 µM of benzil or BNPP was added to each well. The plates were gently rocked to mix the media. Also included were conditions with inhibitors alone (DMEM+2% FBS+ 0.5% DMSO+100 µM benzil or BNPP) and media alone (DMEM+2% FBS+0.5% DMSO) in triplicate. The plates were returned to 37° C. for 48 h.

Luciferase Assay: The Bright-Glo reagent (Promega) was removed from the −80° C. freezer and allowed to thaw it at 4° C. in the dark. The amount to reagent necessary for the experiment (3.65 mL) was removed, and the remaining reagent returned to the stock container to −80° C. The Glo Lysis Buffer and the Bright Glow reagent were allowed to warm to room temperature for 30 min in the dark. The 96 well plate was removed from the incubator and the cells to allowed cool to room temperature for 30 min. The media was removed from the cells, and each well was gently washed in 100 µL of phosphate buffered saline (PBS). The PBS was removed and then 50 µL of the Glo Lysis Buffer was added to each well, followed by gently rocking the plate for 15 min at room temperature in the dark to ensure complete cell lysis. To each well of the 96-well plate was added 50 µL of the Bright Glo reagent and it was mixed well with the lysate. The plate was inserted into a GloMax 96 plate reader and allowed to sit for 5 min in the dark for the luciferase reaction to reach a steady state. The luminescence on the plate was read by using the pre-installed "Bright Glo" Promega program (Synergy Software) and the data were collected and saved. The data were fit to a 4 parameter logistic curve using Kaleidagraph using the following equation: $100/(1+(x/m3)^4)$.

The data obtained are summarized in Table 6 below. The data consistently show that the antiviral effects of a representative compound, GTB, were reduced by the addition of the carboxylesterase inhibitors such as benzil, a specific human carboxylesterase 1 and 2 inhibitor, and bis-p-nitrophenyl phosphate (BNPP), a non-specific esterase inhibitor. The $IC_{50}$ of GTB was increased by the addition of 100 µM Benzyl or BNPP by 2.5-fold and 1.6-fold, respectively. Without wishing to be bound by a particular theory, the disclosed gemcitabine analogs of the present invention upon entering liver cells can be converted to their parent compound gemcitabine by carboxylesterase.

TABLE 6

ATTENUATION OF GTB ANTI-HCV ACTIVITY BY BENZIL*, AND BNPP.**

| | $IC_{50}$ (nM) | | | Fold-change in $IC_{50}$ | |
|---|---|---|---|---|---|
| | −Benzil | | | | |
| Compound | −BNPP | +Benzil | +BNPP | +Benzil | +BNPP |
| GTB | 49 +/− 9 | 125 +/− 10 | 81 +/− 6 | 2.5 | 1.6 |

*Benzil is a specific human carboxylesterase inhibitor; used at 100 µM.
**BNPP is a non-specific esterase inhibitor; used at 100 µM.

g. Experimental Procedures of Stability Test of Each HPLC-Purified Gemcitabine Analog at Different pH Conditions A stock each gemcitabine analog (1 mM in ddH$_2$O) was used to prepare a 200 µM solution of the analog in a specific buffer (see Table 7 below). The solution was then incubated for 4 hours at 40° C.

TABLE 7

COMPONENTS OF THE INCUBATED SOLUTIONS

| pH Condition | Reaction Conditions |
|---|---|
| pH 8 | 40 µl Gemcitabine Analog stock (1 mM)<br>40 µl 100 mM HEPES buffer pH 8.0 at 40° C.<br>120 µl ddH$_2$O |
| pH 6 | 40 µl Gemcitabine Analog stock (1 mM)<br>40 µl 100 mM MES buffer pH 8.0 at 40° C.<br>120 µl ddH$_2$O |
| pH 4 | 40 µl Gemcitabine Analog stock (1 mM)<br>40 µl 100 mM Citrate buffer pH 8.0 at 40° C.<br>120 µl ddH$_2$O |
| pH 2 | 40 µl Gemcitabine Analog stock (1 mM)<br>40 µl 0.05 M HCl<br>120 µl ddH$_2$O |
| pH 1 | 40 µl Gemcitabine Analog stock (1 mM)<br>40 µl 0.5 M HCl<br>120 µl ddH$_2$O |

HPLC analysis: 100 µl of the incubated solution was loaded onto the Vydac C18 analytical column 4.6/250 at 1 ml/min water with the following procedures: a. Inject 100 µl the incubated solution; b. Water for 5 minutes at 1 ml/min; c. 0-100% methanol over 30 minutes; d. Back to 20% methanol.

Analysis: The standard HPLC analysis software was used to quantitate the area under each peak. Degradation peaks are quantitated as a percentage of the peak of the same amount of control sample (no heat treatment).

The data obtained are summarized in Table 8 below. The data show GCB, which comprises a phenyl ring that is dichloro substituted, is both acid and base labile, whereas GTB, which comprises a phenyl ring that is trimethoxy substituted, is quite stable over a broad pH range.

TABLE 8

STABILITY OF GEMCITABINE ANALOGS (200 µM EACH) IN AQUEOUS BUFFERS AFTER 4 HOURS AT 40° C.

Figure 4:
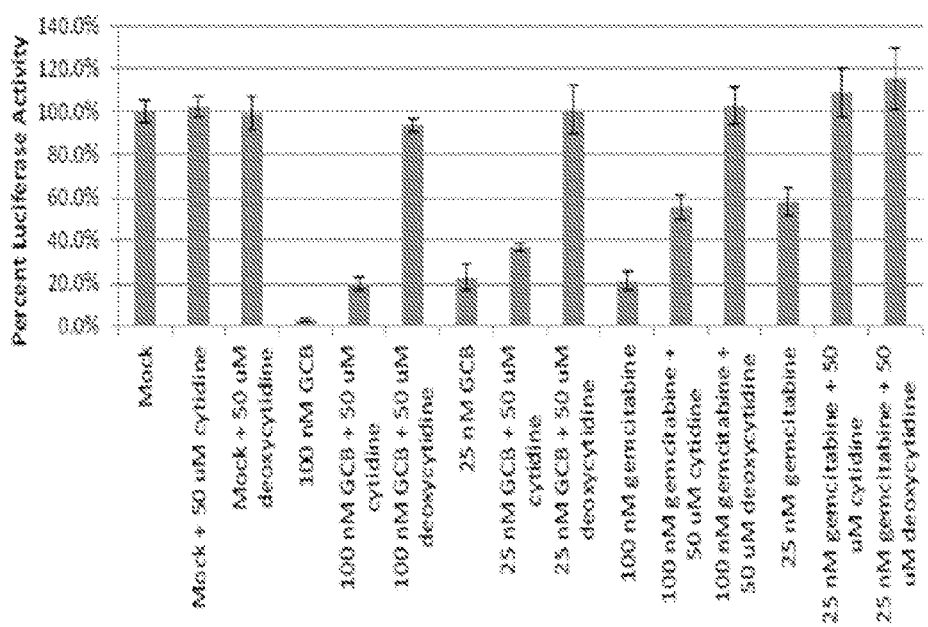
FIG. 4 shows the anti-HCV effects of gemcitabine and the gemcitabine analogs can be reversed by exogenous nucleosides. (Panels A and B) Huh7 cells containing the HCV luciferase replicon were treated with media alone (Mock), GCB (1000, 100 or 25 nM) or gemcitabine (1000, 100 or 25 nM) either alone or with 50 µM cytidine or 2'-deoxycitidine as a competitor. After 48 hours, the cells were lysed, and the total luciferase activity was determined. The data show that up to 500 µM of 3,5-dichlorobenzoic acid, the byproduct of GCB after activation by carboxylesterase has little effect on HCV replicon. (Panel C) Huh7 cells containing the HCV luciferase replicon were treated with media alone or media containing gemcitabine, GCB, GTB or G3DB at concentrations of 1000, 100 or 25 nM. Where indicated, either 50 µM cytidine (C) or 50 µM 2'-deoxycitidine (dC) was also included.
Figure 4:
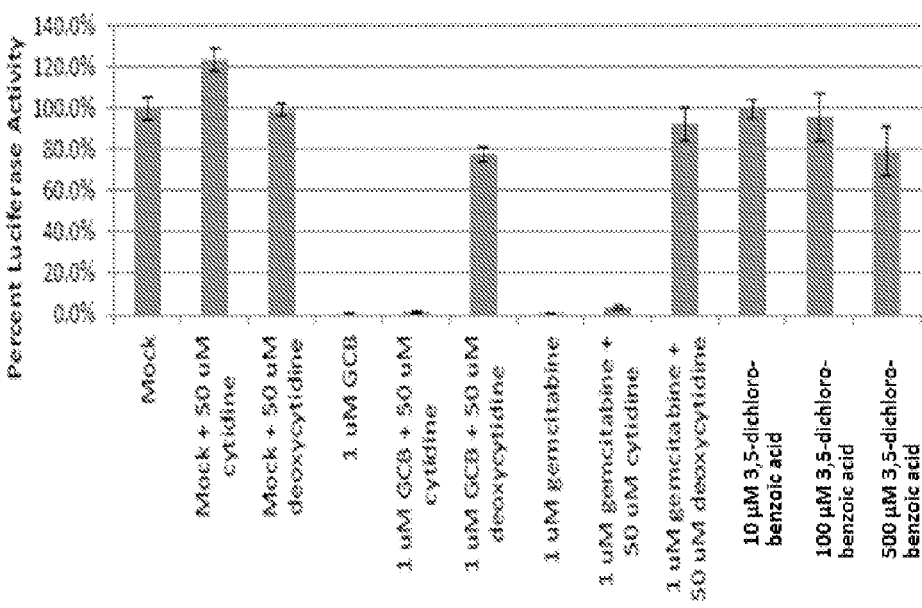
Figure 5:
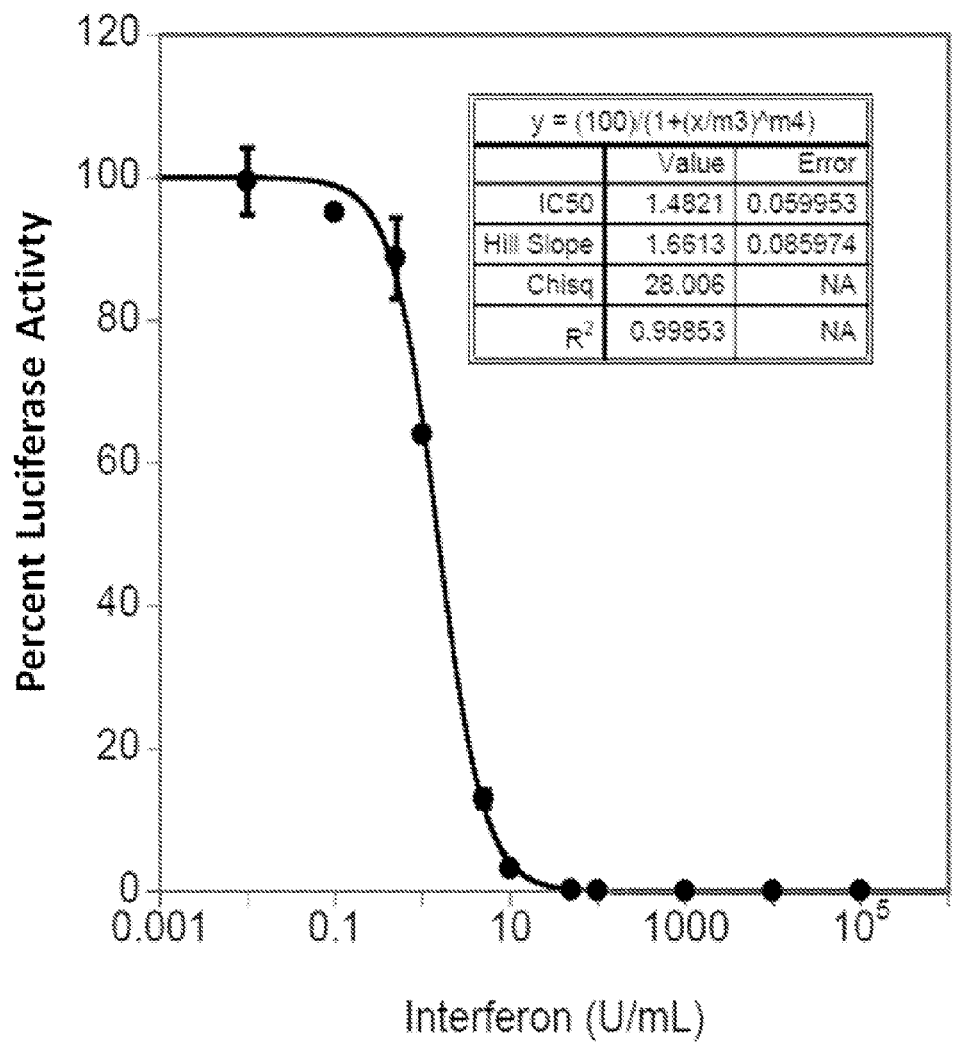
FIG. 5 shows dose-dependent inhibition of the HCV replicon by Interferon alpha 2A (IFN-α2A). Huh7 cells containing the HCV luciferase replicon were treated with IFN-α2A at concentrations from $10^5$ U/mL to 0.01 U/mL in triplicate. After 48 hours, the cells were lysed, and the total luciferase activity was determined. The data were then fit to a 4-parameter logistic curve to obtain the IC$_{50}$ value.
Figure 6:
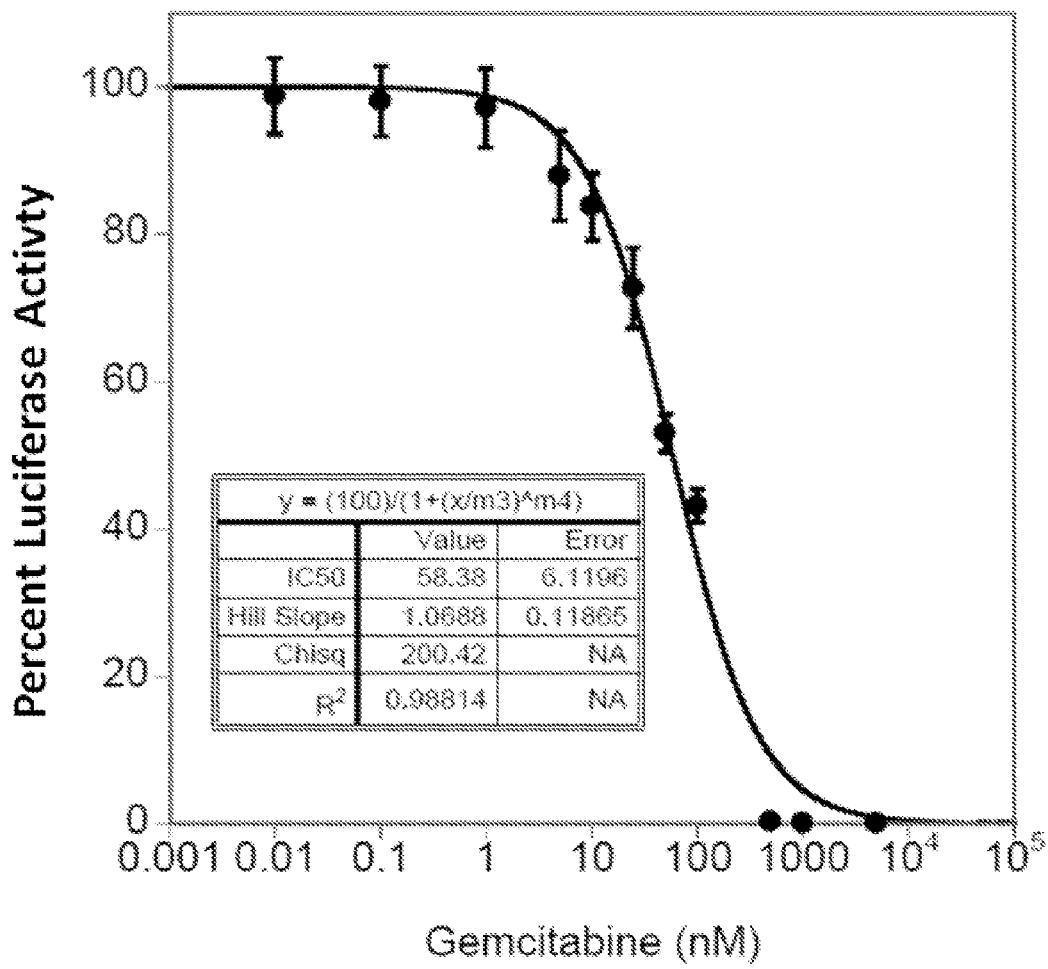
FIG. 6 shows dose-dependent inhibition of the HCV replicon by gemcitabine. Huh7 cells containing the HCV luciferase replicon were treated with gemcitabine at concentrations from 0.5 mM to 0.01 nM in triplicate. After 48 hours, the cells were lysed, the total luciferase activity was determined. The data were then fit to a 4-parameter logistic curve to obtain the IC$_{50}$ value.
Figure 7:
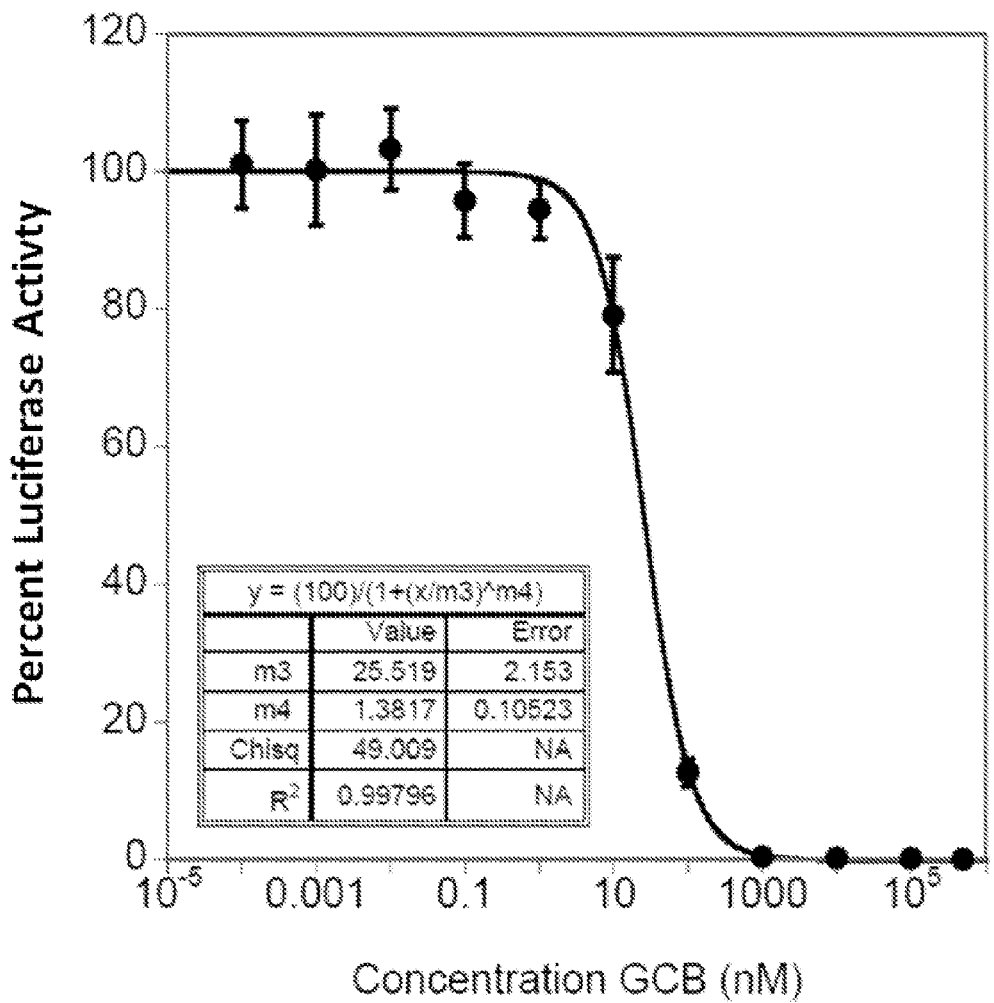
FIG. 7 shows dose-dependent inhibition of the HCV replicon by HPLC-purified GCB. Huh7 cells containing the HCV luciferase replicon were treated with GCB at concentrations from 0.5 mM to 0.01 nM in triplicate. After 48 hours, the cells were lysed, the total luciferase activity was determined. The data were then fit to a 4-parameter logistic curve to obtain the IC50 value.
Figure 8:
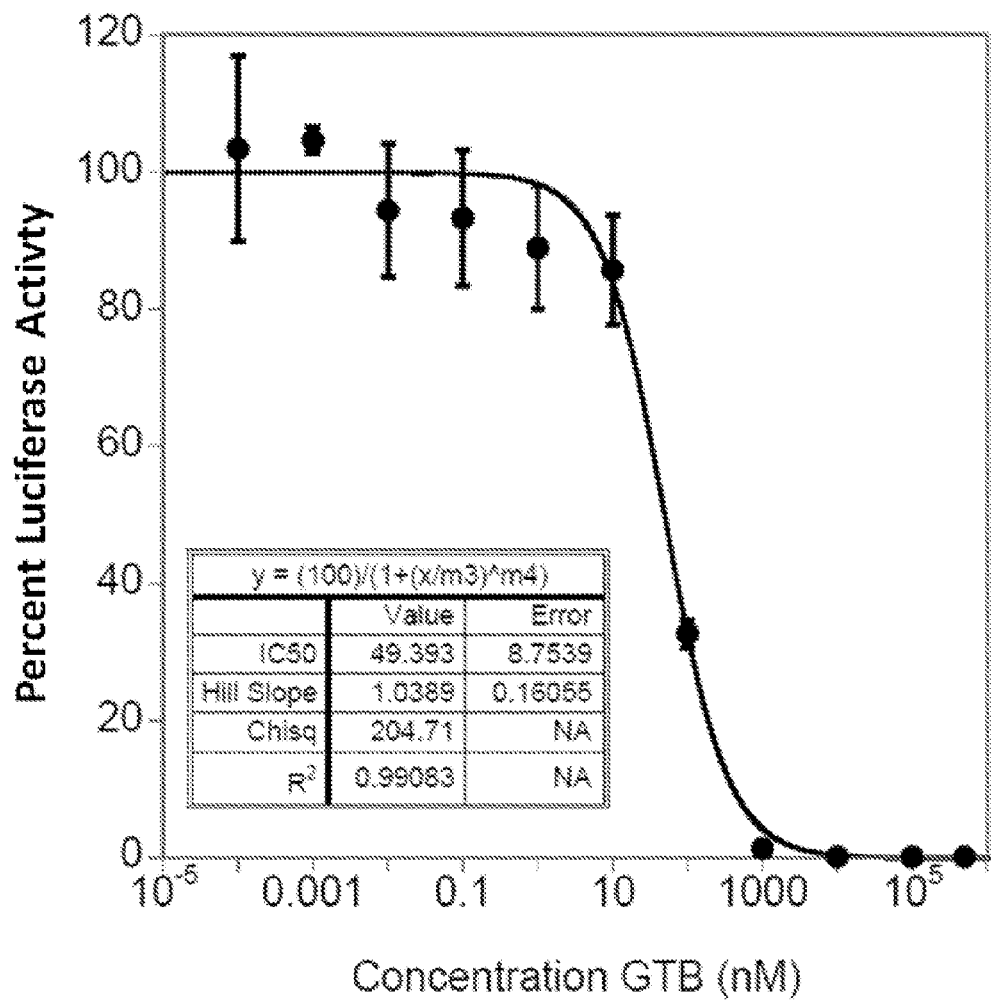
FIG. 8 shows dose-dependent inhibition of the HCV replicon by HPLC-purified GTB. Huh7 cells containing the HCV luciferase replicon were treated with GTB at concentrations from 0.5 mM to 0.01 nM in triplicate. After 48 hours, the cells were lysed, the total luciferase activity was determined. The data were then fit to a 4-parameter logistic curve to obtain the IC$_{50}$ value.

| Condition | % of GCB remaining | % of GTB remaining |
|---|---|---|
| Pretreatment | 100 | 100 |
| pH 1 | 35 | 86 |
| pH 2 | 82 | 87 |
| pH 4 | 98.4 | 98.6 |
| pH 6 | 99.6 | 99.5 |
| pH 8 | 35.4 | 82.7 | h. Experimental Procedures of Reversal of Anti-HCV Activity by Exogenous Nucleosides The cells were plated, incubated with drug, and luciferase activity assayed essentially as described herein above. The incubation with drug was for 48 h. The data obtained are shown in FIG. 4. The data show reversal of the inhibition of the HCV luciferase replicon by gemcitabine, GTB, GCB, and G3DB by deoxycytidine and cytidine. However, the reversal by cytidine was observed to be attenuated compared to deoxycytidine in some cases. The presence of 3,5-dichlorobenzoic acid, a predicted product of GCB after activation by carboxylesterases, has little effect on the HCV luciferase replicon.

i. Synergism of Disclosed Compounds with Other Anti-Viral Compounds

Isobologram analysis was carried to assess the potential synergistic interaction of representative disclosed compounds with representative antiviral compounds. The isobolgram analysis was conducted as previously described by Chou and Talalay (see Chou T. C. and Talalay P. "Analysis of combined drug effects: a new look at a very old problem." Trends Pharmacol Sci 1983; 4:450-4; and Chou T. C. and Talalay P. "Quantitative analysis of dose-effect relationships: the combined effects of multiple drugs or enzyme inhibitors." Adv Enzyme Regul 1984; 22:27-55). The definitions of synergism are those described by Chou (see Chou, T. C. (2006) Theoretical basis, experimental design, and computerized simulation of synergism and antagonism in drug combination studies. Pharmacol Rev. 58(3):621-81).

In the synergism studies described herein, the antiviral compounds shown in Table 9 were assessed in combination with the representative disclosed compound, GTB, and compared to gemcitabine.

TABLE 9

Anti-viral compounds.

| Compound ID | Description |
|---|---|
| PSI-6130 | Other names: 4-Amino-1-((2R,3R,4R,5R)-3-fluoro-4-hydroxy-5-(hydroxymethyl)-3-methyltetrahydrofuran-2-yl)pyrimidin-2(1H)-one<br>Structure:<br>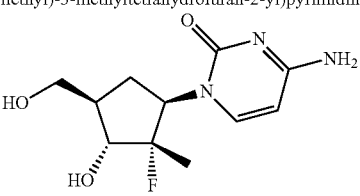 |

TABLE 9-continued

PSI-7977  Other names: sofosbuvir; isopropyl (2S)-2-[[[(2R,3R,4R,5R)-5-(2,4-dioxopyrimidin-1-yl)-4-fluoro-3-hydroxy-4-methyl-tetrahydrofuran-2-yl]methoxy-phenoxy-phosphoryl]amino]propanoate
Structure:

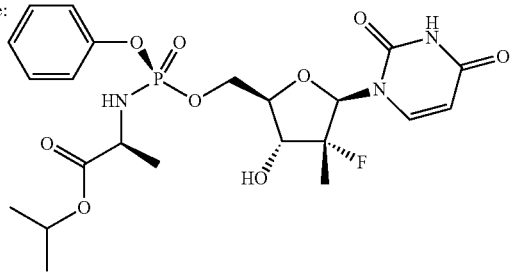

BMS-790052  Other names: daclatasvir; carbamic acid, N,N'-[[1,1'-biphenyl]-4,4'-diylbis[1H-imidazole-5,2-diyl-(2S)-2,1-pyrrolidinediyl[(1S)-1-(1-methylethyl)-2-oxo-2,1-ethanediyl]]]bis-,C,C'-dimethyl ester
Structure:

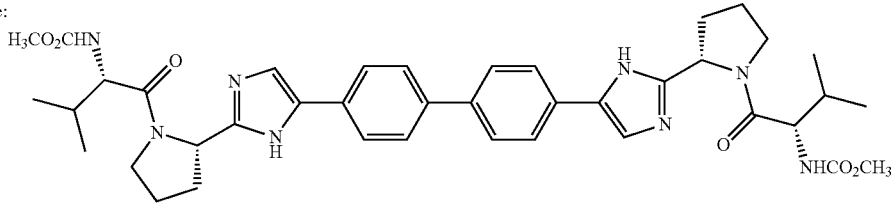

Data for the isobologram analysis are shown in FIGS. 12-15, and shown in each figure are the test compound concentrations and corresponding combination index. The results regarding synergism are summarized in Table 10 below. The data show that gemcitabine may potentiate the actions of PSI-6130. Without wishing to be bound by a particular theory, the potentiation could result from lowering dCTP and CTP pools (see scheme shown in FIG. 2). In contrast, the interaction of GTB and PSI-7977 can be antagonistic or possibly nearly additive. Without wishing to be bound by a particular theory, it is possible that GTB and PSI-7977 are both activated by CES2 cleavage, and if GTB cleavage by CES1 is a rate-limiting step of GTB activation, then the presence of both GTB and PSI-7977 can result in competition resulting in slight antagonism. Alternatively, the data, based on the observed IC$_{50}$ determined for GTB, could be interpreted as showing an additive effect. The data show that BMS-790052, an NS5A inhibitor, appears to potentiate the activity of GTB. Without wishing to be bound by a particular theory, potentiation of the activity of a disclosed gemcitabine analog can result from co-treatment with a compound that inhibits a different HCV protein, e.g. NS5A, than the target of the disclosed gemcitabine analogs, i.e. the HCV RNA-dependent RNA polymerase.

TABLE 10

DRUG INTERACTIONS DETERMINED BY ISOBOLOGRAM ANALYSIS.

| Compound 1 | Compound 2 | Interaction Type |
| --- | --- | --- |
| gemcitabine | PSI-6130 | synergism |
| gemcitabine | PSI-7977 | slight synergism |
| GTB | BMS-790052 | moderate synergism |
| GTB | PSI-7977 | moderate antagonism |

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound, or pharmaceutically acceptable salt, solvate, or polymorph thereof, having a structure represented by a formula:

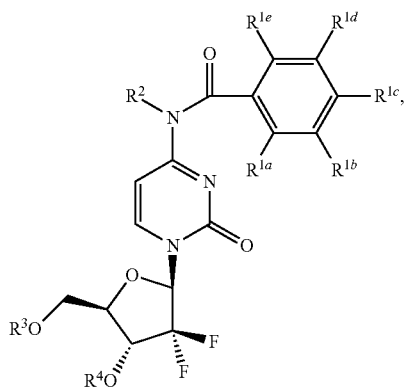

wherein:
R$^{1a}$ and R$^{1e}$ are independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted benzyl, optionally substituted phenoxy, nitro, amino, monoalkylamino, and dialkylamino;
R$^{1b}$ and R$^{1d}$ are independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, nitro, —NH$_2$, amino, monoalkylamino, and dialkylamino;

R$^{1c}$ is selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, —C(O)R$^5$, —C(O)OR$^5$, —C(O)NHR$^5$, —OC(O)R$^5$, —NHC(O)R$^5$, and —NHC(O)OR$^5$;

at least one of R$^{1a}$, R$^{1b}$, R$^{1c}$, R$^{1d}$, and R$^{1e}$ is not hydrogen;

R$^5$ is hydrogen, methyl, ethyl, propyl, butyl, pentyl, or hexyl;

R$^2$ is selected from hydrogen, C1-C4 alkyl, and amine protecting group;

R$^3$ is selected from hydrogen and hydroxyl protecting group;

R$^4$ is selected from hydrogen, C1-C8 alkyl, and hydroxyl protecting group;

or R$^3$ and R$^4$ together comprise a divalent moiety having a structure represented by a formula:

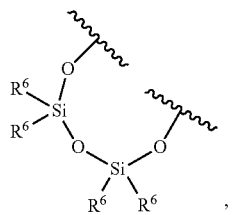

and each R$^6$ is independently selected from methyl, ethyl, propyl, and butyl.

2. The compound of claim 1, wherein at least two of R$^{1a}$, R$^{1b}$, R$^{1c}$, R$^{1d}$, and R$^{1e}$ are not hydrogen.

3. The compound of claim 1, wherein at least three of R$^{1a}$, R$^{1b}$, R$^{1c}$, R$^{1d}$, and R$^{1e}$ are not hydrogen.

4. The compound of claim 1, wherein R$^{1a}$=R$^{1e}$.

5. The compound of claim 1, wherein R$^{1a}$=R$^{1e}$ and wherein R$^{1b}$, R$^{1c}$, and R$^{1d}$ are hydrogen.

6. The compound of claim 1, wherein R$^{1b}$=R$^{1d}$.

7. The compound of claim 1, wherein R$^{1b}$=R$^{1d}$, and wherein R$^{1a}$, R$^{1c}$, and R$^{1e}$ are hydrogen.

8. The compound of claim 1, wherein R$^{1b}$=R$^{1c}$=R$^{1d}$.

9. The compound of claim 1, wherein R$^{1b}$=R$^{1c}$=R$^{1d}$, and wherein R$^{1a}$ and R$^{1e}$ are hydrogen.

10. The compound of claim 1, wherein R$^2$ is an amine protecting group selected from the group consisting of Fmoc, BOC, Cbz, acetyl, trifluoroacetamide, phthalimide, benzyl, triphenylmethylamine, benzylideneamine, and p-toluenesulfonamide.

11. The compound of claim 1, wherein R$^3$ and R$^4$ are independently a hydroxyl protecting group, wherein the hydroxyl protecting group is selected from the group consisting of MOM, THP, t-butyl ether, allyl ether, benzyl, TIPDS, TBDMS, TBDPS, acetyl, pivalic acid ester, acetonide, benzoyl, and benzylidene acetal.

12. The compound of claim 1, wherein R$^2$, R$^3$, and R$^4$ are hydrogen.

13. The compound of claim 1, wherein either R$^{1a}$ and R$^{1e}$, or R$^{1b}$ and R$^{1d}$ are independently selected from fluoromethyl, fluoromethoxy, difluoromethyl, difluoromethoxy, trifluoromethyl, and trifluoromethoxy.

14. The compound of claim 1, wherein either R$^{1a}$ and R$^{1e}$, or R$^{1b}$ and R$^{1d}$ are selected from fluoro, chloro, bromo, and iodo.

15. The compound of claim 1, wherein either R$^{1a}$ and R$^{1e}$, or R$^{1b}$ and R$^{1d}$ are selected from methyl, ethyl, propyl, and butyl.

16. The compound of claim 1, wherein either R$^{1a}$ and R$^{1e}$, or R$^{1b}$ and R$^{1d}$ are selected from methoxy, ethoxy, propoxy, and butoxy.

17. The compound of claim 1, wherein either R$^{1a}$ and R$^{1e}$, or R$^{1b}$ and R$^{1d}$ are selected from cyano, hydroxy, thiol, alkylthiol, optionally substituted benzyl, and optionally substituted phenoxy.

18. The compound of claim 1, wherein either R$^{1a}$ and R$^{1e}$, or R$^{1b}$ and R$^{1d}$ are selected from nitro, —NH$_2$, amino, monoalkylamino, and dialkylamino.

19. The compound of claim 1, wherein either R$^{1a}$ and R$^{1e}$, or R$^{1b}$ and R$^{1d}$ are selected from fluoro, chloro, bromo, iodo, and methoxy.

20. The compound of claim 1, wherein R$^{1c}$ is selected from fluoromethyl, fluoromethoxy, difluoromethyl, difluoromethoxy, trifluoromethyl, and trifluoromethoxy.

21. The compound of claim 1, wherein R$^{1c}$ is selected from methyl, ethyl, propyl, and butyl.

22. The compound of claim 1, wherein R$^{1c}$ is selected from methoxy, ethoxy, propoxy, and butoxy.

23. The compound of claim 1, wherein R$^{1c}$ is selected from cyano, hydroxy, thiol, alkylthiol, optionally substituted phenyl, optionally substituted benzyl, and optionally substituted phenoxy.

24. The compound of claim 1, wherein R$^{1c}$ is selected from —C(O)R$^5$, —C(O)OR$^5$, —C(O)NHR$^5$, —OC(O)R$^5$, —NHC(O)R$^5$, and —NHC(O)OR$^5$.

25. The compound of claim 1, wherein R$^{1c}$ is selected from fluoro, chloro, bromo, iodo, and methoxy.

26. The compound of claim 1,
wherein two or three of R$^{1a}$, R$^{1b}$, R$^{1c}$, R$^{1d}$, and R$^{1e}$ are not hydrogen;
each of R$^{1a}$, R$^{1b}$, R$^{1c}$, R$^{1d}$, and R$^{1e}$ is independently selected from hydrogen, chloro, and methoxy; and
R$^2$, R$^3$, and R$^4$ are hydrogen.

27. The compound of claim 26, wherein R$^{1a}$=R$^{1e}$≠H, or R$^{1b}$=R$^{1d}$≠H, or R$^{1a}$=R$^{1c}$=R$^{1e}$≠H, or R$^{1b}$=R$^{1c}$=R$^{1d}$≠H.

28. The compound of claim 1 having a structure represented by a formula:

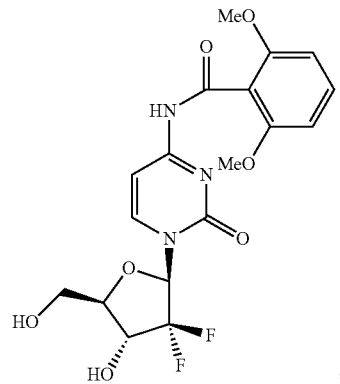

-continued

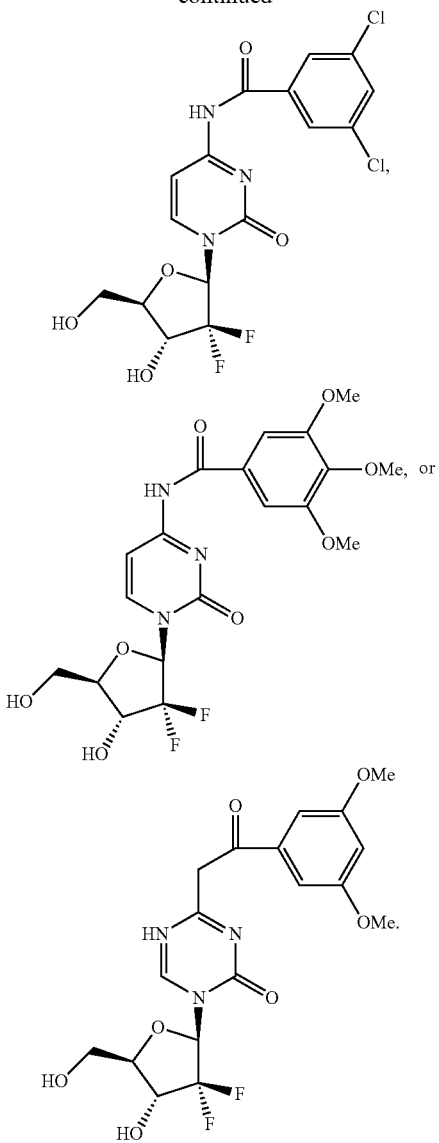

29. A compound, or pharmaceutically acceptable salt, solvate, or polymorph thereof, having a structure represented by a formula:

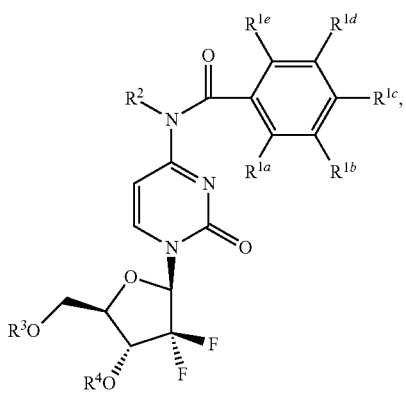

wherein:

each of $R^{1a}$, $R^{1b}$, $R^{1c}$, $R^{1d}$, and $R^{1e}$ is independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, nitro, —NH$_2$, amino, monoalkylamino, dialkylamino, —C(O)R$^5$, —C(O)OR$^5$, —C(O)NHR$^5$, —OC(O)R$^5$, —NHC(O)R$^5$, and —NHC(O)OR$^5$;

at least two of $R^{1a}$, $R^{1b}$, $R^{1c}$, $R^{1d}$ and $R^{1e}$, are not hydrogen and are the same;

$R^5$ is hydrogen, methyl, ethyl, propyl, butyl, pentyl, or hexyl;

$R^2$ is selected from hydrogen, C1-C4 alkyl, and amine protecting group;

$R^3$ is selected from hydrogen and hydroxyl protecting group;

$R^4$ is selected from hydrogen, C1-C8 alkyl, and hydroxyl protecting group;

or $R^3$ and $R^4$ together comprise a divalent moiety having a structure represented by a formula:

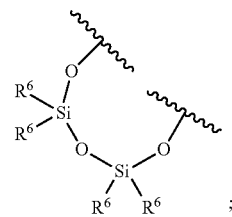

each $R^6$ is independently selected from methyl, ethyl, propyl, and butyl.

30. The compound of claim 29, wherein at least three of $R^{1a}$, $R^{1b}$, $R^{1c}$, $R^{1d}$, and $R^{1e}$ are not hydrogen.

31. The compound of claim 29, wherein $R^{1a}$=$R^{1e}$≠H, or $R^{1b}$=$R^{1d}$≠H, or $R^{1a}$=$R^{1c}$=$R^{1e}$≠H, or $R^{1b}$=$R^{1c}$=$R^{1d}$≠H.

32. The compound of claim 29, wherein $R^2$, $R^3$, and $R^4$ are hydrogen.

33. The compound of claim 29, wherein $R^{1a}$=$R^{1e}$.

34. The compound of claim 29, wherein $R^{1b}$=$R^{1d}$.

35. The compound of claim 29, wherein $R^{1b}$=$R^{1c}$=$R^{1d}$.

36. The compound of claim 29, wherein either $R^{1a}$ and $R^{1e}$, or $R^{1b}$ and $R^{1d}$ are independently selected from fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted benzyl, optionally substituted phenoxy, nitro, —NH$_2$, amino, monoalkylamino, and dialkylamino.

37. A method of making a compound as defined in claim 1 comprising the steps of:

(a) providing a first compound having a structure represented by a formula:

81

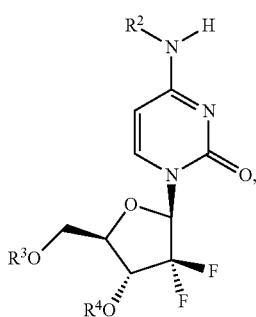

wherein R² is selected from hydrogen, C1-C4 alkyl, and amine protecting group;
R³ is selected from hydrogen and hydroxyl protecting group; and
R⁴ is selected from hydrogen, C1-C8 alkyl, and hydroxyl protecting group;
or R³ and R⁴ together comprise a divalent moiety having a structure represented by a formula:

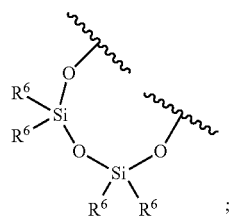

each R⁶ is independently selected from methyl, ethyl, propyl, and butyl, and (b) reacting with a second compound having a structure represented by a formula:

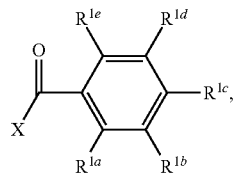

82 wherein X is halogen or pseudohalogen;
wherein 1, 2, 3, 4, or 5 of $R^{1a}$, $R^{1b}$, $R^{1c}$, $R^{1d}$, and $R^{1e}$ are not hydrogen; and
each of $R^{1a}$, $R^{1b}$, $R^{1c}$, $R^{1d}$, and $R^{1e}$ is independently selected from hydrogen, fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, propoxy, butyl, butoxy, cyano, hydroxy, thiol, alkylthiol, optionally substituted phenyl, optionally substituted benzyl, optionally substituted phenoxy, nitro, —NH₂, amino, monoalkylamino, dialkylamino, —C(O)R⁵, —C(O)OR⁵, —C(O)NHR⁵, —OC(O)R⁵, —NHC(O)R⁵, and —NHC(O)OR⁵, wherein R⁵ is hydrogen, methyl, ethyl, propyl, butyl, pentyl, or hexyl,
thereby forming an amide bond.

38. A pharmaceutical composition comprising the compound of claim 1 and a pharmaceutically acceptable carrier.

39. A method for treating a subject having a disorder selected from a the group consisting of a viral infection selected from the group consisting of dengue virus, human immunodeficiency virus, hepatitis A, hepatitis B, hepatitis C, herpes simplex, cytomegalovirus, Epstein-Barr virus, and yellow fever virus and cancer, the method comprising administering to the subject in need thereof an effective amount of the compound of claim 1.

40. The method of claim 39, wherein the cancer is selected from the group consisting of non-small cell lung cancer, pancreatic cancer, bladder cancer, esophageal cancer, lymphoma, and breast cancer.

41. A method for inhibiting viral replication in a cell, wherein the virus is selected from the group consisting of dengue virus, human immunodeficiency virus, hepatitis A, hepatitis B, hepatitis C, herpes simplex, cytomegalovirus, Epstein-Barr virus, and yellow fever virus or inhibiting growth of a neoplastic cell, the method comprising contacting the cell with the compound of claim 1.

42. The method of claim 41, wherein the neoplastic cell is selected from the group consisting of a non-small cell lung cancer cell, a pancreatic cancer cell, a bladder cancer cell, an esophageal cancer cell, a lymphoma cell, and a breast cancer cell.

* * * * *

UNITED STATES PATENT AND TRADEMARK OFFICE
CERTIFICATE OF CORRECTION

PATENT NO. : 9,447,137 B2  Page 1 of 3
APPLICATION NO. : 14/440811
DATED : September 20, 2016
INVENTOR(S) : Zucai Suo It is certified that error appears in the above-identified patent and that said Letters Patent is hereby corrected as shown below:

In the Drawings

Sheet 6 of 16 (Figure 5) Line 1 (Y-axis), Change "Activty" to --Activity--.

Sheet 7 of 16 (Figure 6) Line 1 (Y-axis), Change "Activty" to --Activity--.

Sheet 8 of 16 (Figure 7) Line 1 (Y-axis), Change "Activty" to --Activity--.

Sheet 9 of 16 (Figure 8) Line 1 (Y-axis), Change "Activty" to --Activity--.

In the Specification

Column 3 Line 9, Change "$R^{1b}=R^{1e}$ H, or $R^1=R^{1d}\neq H$," to --$R^{1b}=R^{1e}\neq H$, or $R^{1c}=R^{1d}\neq H$,--.

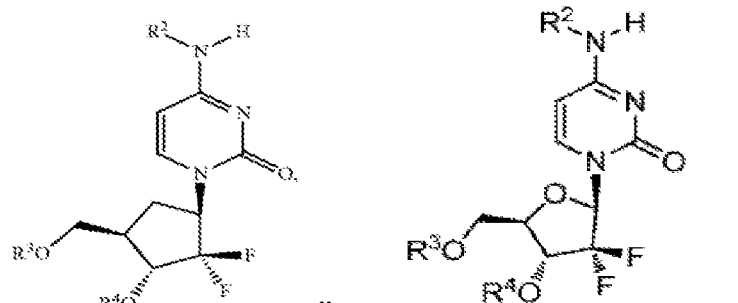

Column 4 Lines 16-30, Change "            " to --            --.

Column 6 Line 23, Change "2'-deoxycitidine" to --2'-deoxycytidine--.

Column 6 Line 32, Change "2'-deoxycitidine" to --2'-deoxycytidine--.

Signed and Sealed this
Eighteenth Day of July, 2017

Joseph Matal
*Performing the Functions and Duties of the
Under Secretary of Commerce for Intellectual Property and
Director of the United States Patent and Trademark Office*

Column 11 Lines 64-65, Change "antiarrythmics)," to --antiarrhythmics),--.

Column 14 Lines 19-20, Change "disubstituted" to --di-substituted--.

Column 14 Line 65, Change "disubstituted" to --di-substituted--.

Column 15 Line 43, Change "ofunsaturation," to --of unsaturation,--.

Column 21 Lines 52-53, Change "—(CH$_2$)$_{0-4}$N(R)$_2$;" to -- —(CH$_2$)$_{0-4}$N(R°)$_2$;--.

Column 21 Line 60, Change "—C(S)NR$_2$;" to -- —C(S)NR°$_2$;--.

Column 21 Line 61, Change "—(CH$_2$)$_{0-4}$OC(O)NR$_2$;" to -- —(CH$_2$)$_{0-4}$OC(O)NR°$_2$;--.

Column 23 Line 65, Change "Cahn-Inglod-Prelog" to --Cahn-Ingold-Prelog--.

Column 24 Line 51, Change "Medicines"" to --Medicines?"--.

Column 30 Line 49, Change "$R^{1d}$=$R^{1e}$H;" to --$R^{1d}$=$R^{1e}$≠H--.

Column 33 Line 64, Change "RC" to --$R^{1c}$--.

Column 33 Line 66, Change "RC" to --$R^{1c}$--.

Column 34 Line 13, Change "$R^{1a}$=$R^{1c}$=$R^{1}$≠H" to --$R^{1a}$=$R^{1c}$=$R^{1e}$≠H--.

Column 35 Line 25, Change "$R^{1d}$" to --$R^{1c}$--.

Column 36 Lines 40-48, Change " 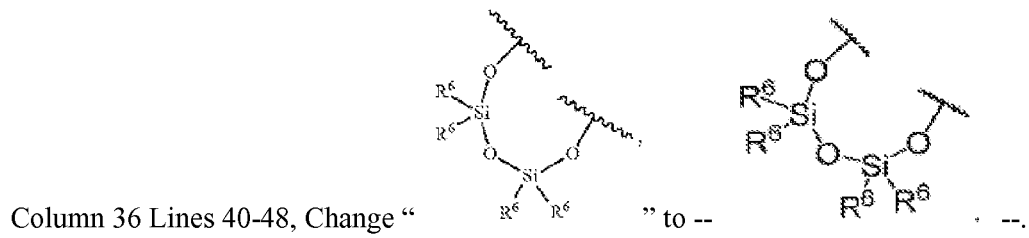 --.

Column 53 Line 29, Change "syringability." to --syringeability.--.

Column 57 Line 40, Change "dily)" to --diyl)--.

Column 62 Line 14, Change ">$^{99}$%." to -->99%.--.

Column 71 Line 54, Change "100 M." to --100 μM.--.

CERTIFICATE OF CORRECTION (continued)
U.S. Pat. No. 9,447,137 B2

Column 72 Line 33, Change "100/(1+(x/m3)^4)." to --100/(1+(x/m3)^m4).--.

Columns 73-74 Line 57, Change " 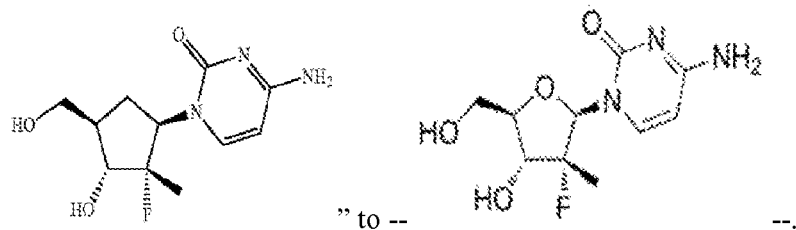 " to -- --.

Column 74 Lines 33-34, Change "isobolgram" to --isobologram--.

In the Claims

Column 77 Lines 30-40, Claim 1, change " 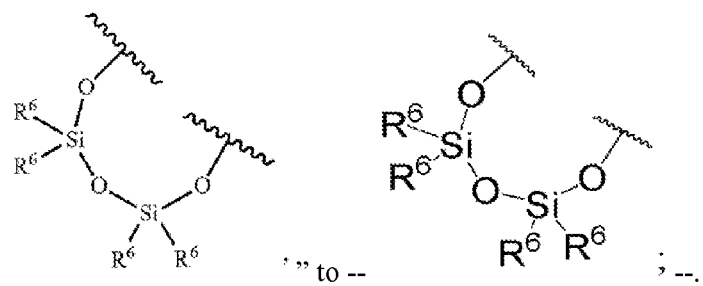 " to -- ; --.

Column 79 Lines 30-40, Claim 28, change " 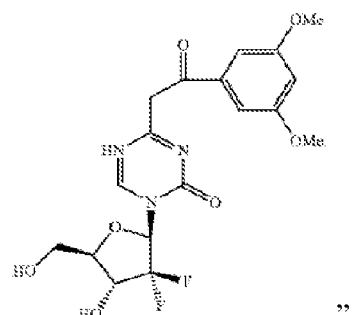 " to -- 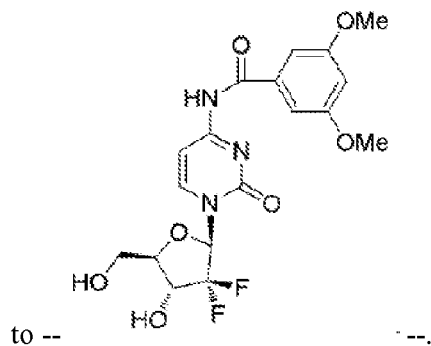 --.

Column 80 Line 15, Claim 29, change "$R^{1e}$," to --$R^{1e}$--.

Column 82 Line 22 Claim 39, change "a the" to --the--.